US 10,809,519 B2

(12) United States Patent
McDowall

(10) Patent No.: US 10,809,519 B2
(45) Date of Patent: Oct. 20, 2020

(54) INCREASED RESOLUTION AND DYNAMIC RANGE IMAGE CAPTURE UNIT IN A SURGICAL INSTRUMENT AND METHOD

(71) Applicant: Intuitive Surgical Operations, Inc., Sunnyvale, CA (US)

(72) Inventor: Ian E. McDowall, Woodside, CA (US)

(73) Assignee: KITAGAWA INDUSTRIES CO., LTD., Aichi (JP)

( * ) Notice: Subject to any disclaimer, the term of this patent is extended or adjusted under 35 U.S.C. 154(b) by 79 days.

(21) Appl. No.: 16/139,288

(22) Filed: Sep. 24, 2018

(65) Prior Publication Data

US 2019/0025569 A1 Jan. 24, 2019

Related U.S. Application Data

(60) Continuation of application No. 14/258,275, filed on Apr. 22, 2014, now Pat. No. 10,254,533, which is a
(Continued)

(51) Int. Cl.
*A61B 1/00* (2006.01)
*A61B 1/05* (2006.01)
(Continued)

(52) U.S. Cl.
CPC ...... *G02B 23/2415* (2013.01); *A61B 1/00193* (2013.01); *G02B 5/04* (2013.01);
(Continued)

(58) Field of Classification Search
CPC ............ A61B 1/00004; A61B 1/00009; A61B 1/00096; A61B 1/00163; A61B 1/00186;
(Continued)

(56) References Cited

U.S. PATENT DOCUMENTS

| 4,074,306 A | 2/1978 | Kakinuma et al. |
| 4,473,841 A | 9/1984 | Murakoshi et al. |

(Continued)

FOREIGN PATENT DOCUMENTS

| CN | 101433458 A | 5/2009 |
| CN | 101495834 A | 7/2009 |

(Continued)

OTHER PUBLICATIONS

Cossairt, Oliver and Shree Nayar, "Spectral Focal Sweep: Extended Depth of Field from Chromatic Aberrations," 2010 International Conference on Computational Photography (ICCP), MIT, Cambridge, Massachusetts, Mar. 28-30, 2010, 8 pages.

(Continued)

*Primary Examiner* — Timothy J Neal
*Assistant Examiner* — William B Chou
(74) *Attorney, Agent, or Firm* — Meunier Carlin & Curfman LLC

(57) ABSTRACT

In a minimally invasive surgical system, an image capture unit includes a prism assembly and sensor assembly. The prism assembly includes a beam splitter, while the sensor assembly includes coplanar image capture sensors. Each of the coplanar image capture sensors has a common front end optical structure, e.g., the optical structure distal to the image capture unit is the same for each of the sensors. A controller enhances images acquired by the coplanar image capture sensors. The enhanced images may include (a) visible images with enhanced feature definition, in which a particular feature in the scene is emphasized to the operator of minimally invasive surgical system; (b) images having increased image apparent resolution; (c) images having increased dynamic range; (d) images displayed in a way based on a pixel color component vector having three or (Continued)

more color components; and (e) images having extended depth of field.

11 Claims, 15 Drawing Sheets

Related U.S. Application Data division of application No. 13/209,084, filed on Aug. 12, 2011, now Pat. No. 8,734,328.

(51) Int. Cl.

| | |
|---|---|
| *G02B 23/24* | (2006.01) |
| *G02B 5/04* | (2006.01) |
| *G02B 27/10* | (2006.01) |
| *F21V 8/00* | (2006.01) |
| *G01N 21/64* | (2006.01) |

(52) U.S. Cl.
CPC ......... *G02B 6/001* (2013.01); *G02B 27/1066* (2013.01); *A61B 1/00186* (2013.01); *A61B 1/05* (2013.01); *G01N 21/6456* (2013.01); *G02B 2207/113* (2013.01)

(58) Field of Classification Search
CPC ....... A61B 1/00193; A61B 1/045; A61B 1/05; G02B 23/2415; G02B 5/04; G02B 6/001; G02B 27/1066; G02B 2207/113; G01N 21/6456
See application file for complete search history.

(56) References Cited

U.S. PATENT DOCUMENTS

| | | | |
|---|---|---|---|
| 4,873,572 | A | 10/1989 | Miyazaki et al. |
| 5,647,368 | A | 7/1997 | Zeng et al. |
| 5,743,846 | A | 4/1998 | Takahashi et al. |
| 5,784,162 | A | 7/1998 | Cabib et al. |
| 5,986,271 | A | 11/1999 | Lazarev et al. |
| 6,057,909 | A | 5/2000 | Yahav et al. |
| 6,320,979 | B1 | 11/2001 | Melen |
| 6,331,181 | B1 | 12/2001 | Tierney et al. |
| RE37,752 | E | 6/2002 | Wolff |
| 6,486,974 | B1 | 11/2002 | Nakai et al. |
| 6,772,003 | B2 | 8/2004 | Kaneko et al. |
| 6,837,883 | B2 | 1/2005 | Moll et al. |
| 7,404,929 | B2 | 7/2008 | Fulghum, Jr. |
| 7,722,534 | B2 | 5/2010 | Cline et al. |
| 8,672,838 | B2 | 3/2014 | McDowall |
| 8,684,914 | B2 | 4/2014 | McDowall et al. |
| 8,734,328 | B2 | 5/2014 | McDowall |
| 8,764,633 | B2 | 7/2014 | McDowall |
| 8,784,301 | B2 | 7/2014 | McDowall |
| 9,254,076 | B2 | 2/2016 | McDowall |
| 9,254,078 | B2 | 2/2016 | McDowall |
| 9,675,236 | B2 | 6/2017 | McDowall et al. |
| 9,782,056 | B2 | 10/2017 | McDowall et al. |
| 10,254,533 | B2 | 4/2019 | McDowall |
| 2002/0007110 | A1 | 1/2002 | Irion |
| 2002/0111546 | A1 | 8/2002 | Cook et al. |
| 2003/0083551 | A1 | 5/2003 | Takahashi |
| 2003/0135092 | A1 | 7/2003 | Cline et al. |
| 2004/0125228 | A1 | 7/2004 | Dougherty |
| 2005/0159641 | A1 | 7/2005 | Kanai |
| 2005/0182295 | A1 | 8/2005 | Soper et al. |
| 2006/0173358 | A1 | 8/2006 | Xie |
| 2006/0238614 | A1 | 10/2006 | Konno |
| 2006/0241495 | A1 | 10/2006 | Kurtz |
| 2007/0274577 | A1 | 11/2007 | De Font-Reaulx-Rojas |
| 2008/0013941 | A1 | 1/2008 | Daley |
| 2008/0065105 | A1 | 3/2008 | Larkin et al. |
| 2008/0151041 | A1 | 6/2008 | Shafer et al. |
| 2009/0131800 | A1 | 5/2009 | Liang |
| 2009/0259098 | A1 | 10/2009 | Krattiger |
| 2009/0259101 | A1 | 10/2009 | Unsai |
| 2009/0303318 | A1 | 12/2009 | Hasegawa |
| 2010/0079587 | A1 | 4/2010 | Yoshida |
| 2010/0165080 | A1 | 7/2010 | Yamaguchi et al. |
| 2010/0245550 | A1 | 9/2010 | Ishihara |
| 2011/0063427 | A1 | 3/2011 | Fengler et al. |
| 2011/0292258 | A1 | 12/2011 | Adler et al. |
| 2012/0004508 | A1 | 1/2012 | McDowall et al. |
| 2014/0225992 | A1 | 8/2014 | McDowall |
| 2017/0245744 | A1 | 8/2017 | McDowall |

FOREIGN PATENT DOCUMENTS

| | | |
|---|---|---|
| JP | S62174715 A | 7/1987 |
| JP | S63210813 A | 9/1988 |
| JP | H05341205 A | 12/1993 |
| JP | H07261099 A | 10/1995 |
| JP | H10118004 A | 5/1998 |
| JP | 2000221411 A | 8/2000 |
| JP | 2003047588 A | 2/2003 |
| JP | 2004313523 A | 11/2004 |
| JP | 2005176940 A | 7/2005 |
| JP | 2007135951 A | 6/2007 |
| JP | 2010082040 A | 4/2010 |
| JP | 2011062378 A | 3/2011 |
| JP | 2011120916 A | 6/2011 |
| WO | WO-0176452 A2 | 10/2001 |
| WO | WO-2006101736 A1 | 9/2006 |
| WO | WO-200879578 A3 | 7/2008 |
| WO | WO-2008079578 A2 | 7/2008 |

OTHER PUBLICATIONS

Debevec, Paul E. and Jitendra Malik, "Recovering High Dynamic Range Radiance Maps from Photographs," Proceedings of the Annual Conference on Computer Graphics and Interactive Techniques (SIGGRAPH '97), Aug. 1997, pp. 369-378.

Debevec, Paul E. et al., "Acquiring the reflectance field of a human face," Proceedings of the 27th Annual Conference on Computer Graphics and Interactive Techniques (SIGGRAPH '00), Jul. 23-28, 2000, New Orleans, LA, pp. 145-156, ACM Press/Addison-Wesley Publishing Co.

Extended European Search Report for Application No. 12824330.0, dated Jan. 25, 2016, 14 pages.

International Search Report and Written Opinion for Application No. PCT/US2012/050394, dated Jan. 22, 2013, 9 pages.

Jacques, Steven L. et al., "Imaging Skin Pathology with Polarized Light," Journal of Biomedical Optics, Jul. 2002, vol. 7, Issue 3, pp. 329-340.

Moxtek, "Polarizers: Wire-Grid Polarizing Beamsplitter," Datasheet, last accessed Mar. 27, 2011, 2 pages, Internet: http://www.moxtek.com/templates/moxtek/pdf/datasheets/pbs-pbf%20series.pdf.

Partial Supplementary European Search Report for Application No. 12824330.0, dated Oct. 7, 2015, 6 pages.

The Indian Fusion, "Salt Grain Sized Disposable Camera," 2011, last accessed Apr. 11, 2011, 12 pages, Internet: http://indianfusion.aglasem.com/"s=salt+grain+sized+disposable+camera&x=7&y=9.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

Yi, Hyoungjune, "Detecting semi-specular reflection component from a sequence of images," Scholarly Paper, Department of Computer Science, University of Maryland at College Park, 2007, 18 pages.

Zhao, Y. et al., "Object separation by polarimetric and spectral imagery fusion," Computer Vision and Image Understanding, Aug. 2009, vol. 113, pp. 855-866, Elsevier.

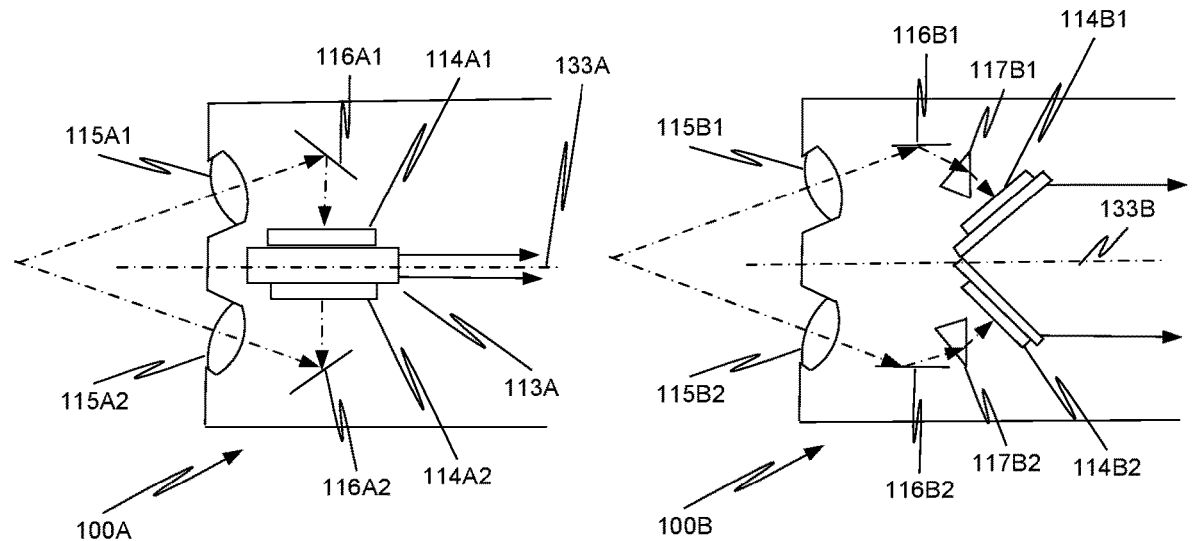
Prior Art
Fig. 1A
Prior Art
Fig. 1B
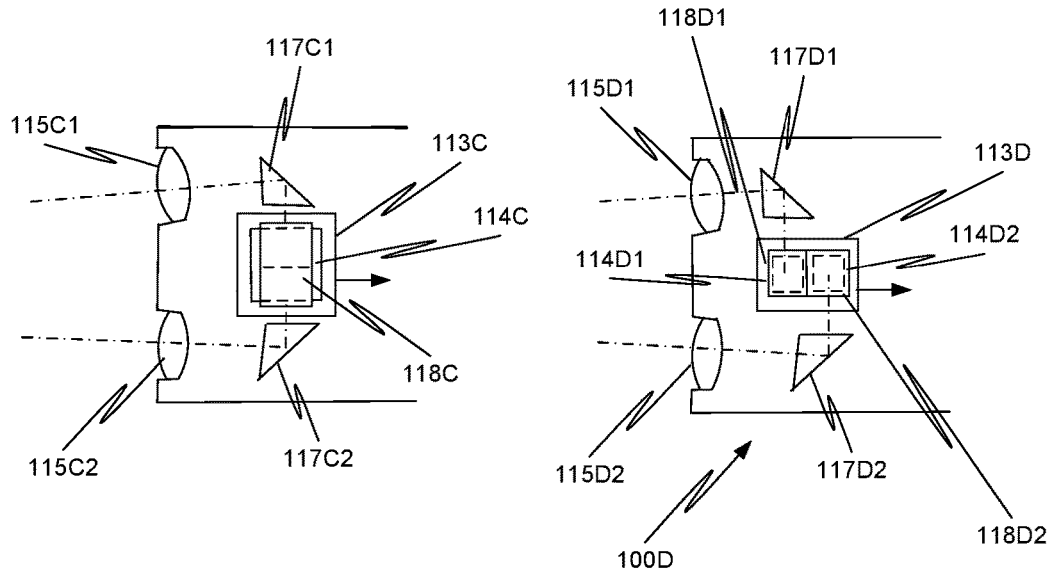
Prior Art
Fig. 1C
Prior Art
Fig. 1D

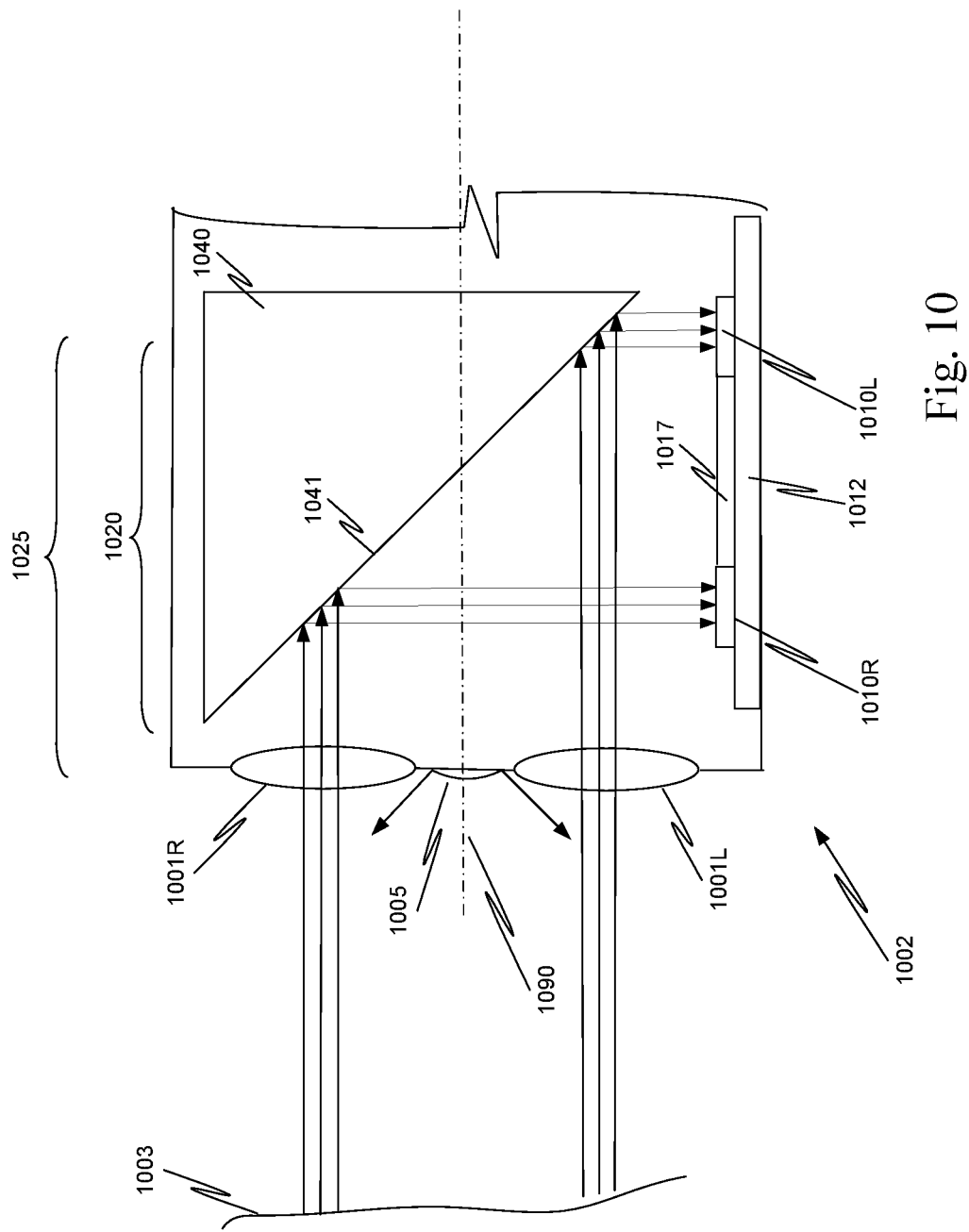

INCREASED RESOLUTION AND DYNAMIC RANGE IMAGE CAPTURE UNIT IN A SURGICAL INSTRUMENT AND METHOD

CROSS REFERENCE TO RELATED APPLICATIONS

This application is a continuation of U.S. patent application Ser. No. 14/258,275 (filed 22 Apr. 2014), which is a divisional of U.S. patent application Ser. No. 13/209,084 (filed 12 Aug. 2011; now U.S. Pat. No. 8,734,328 B2), each of which is incorporated herein by reference.

BACKGROUND

Field of Invention

Aspects of this invention are related generally to endoscopic imaging and are more particularly related to capturing light from a common front end optical structure in a plurality of coplanar image capture sensors.

Related Art

The da Vinci® Surgical Systems, commercialized by Intuitive Surgical, Inc., Sunnyvale, Calif., are minimally invasive teleoperated surgical systems that offer patients many benefits, such as reduced trauma to the body, faster recovery and shorter hospital stay. One key component of a da Vinci® Surgical System (e.g., the model IS3000, da Vinci® Si HD) is a capability to provide two-channel (i.e., left and right) video capture and display of visible images to provide stereoscopic viewing for the surgeon. Such electronic stereoscopic imaging systems may output high definition video images to the surgeon, and may allow features such as zoom to provide a "magnified" view that allows the surgeon to identify specific tissue types and characteristics, as well as to work with increased precision.

Typically in a minimally invasive surgical system, an image capture system is coupled to a proximal end (away from the surgical site) of a stereoscopic endoscope. However, some stereoscopic endoscopes have included image capture components in the distal end (nearest the surgical site) of the endoscope. FIGS. 1A to 1D are examples of image capture sensor configurations in a distal end of a stereoscopic endoscope from U.S. Pat. No. 4,873,572 (filed Feb. 24, 1988).

In FIG. 1A, a distal end 100A of an endoscope includes a plate-like package 113A with a center line coinciding with a longitudinal axis 133A of the endoscope. Two charge coupled devices (CCDs) 114A1 and 114A2 are mounted on opposing surfaces of package 113A. Two objective lenses 115A1 and 115A2 are symmetrically arranged on both sides of longitudinal axis 133A of the endoscope. Mirrors 116A1, 116A2 are symmetrically arranged on the optical axis of the respective objective lenses 115A1, 115A2. Light reflected from an object external to the endoscope passes through objective lens 115A1, 115A2 and is reflected by mirrors 116A1, 116A2 onto the imaging surfaces of CCDs 114A1 and 114A2. The video signals from CCDs 114A1 and 114A2 are transmitted to a video processor external to the endoscope.

In FIG. 1B, a distal end 100B of an endoscope includes two objective lenses 115B1, 115B2 arranged the same as objective lenses 115A1 and 115A2 in FIG. 1A. Mirrors 116B1 and 116B2 are mounted with the mirror surfaces parallel to and removed from longitudinal axis 133B of the endoscope. Light reflected from an object external to the endoscope passes through objective lenses 115B1, 115B2 and is reflected by mirrors 116B1, 116B2 to refracting prisms 117B1, 117B2. The optical path from prisms 117B1, 117B2 is to the imaging surfaces of CCDs 114B1, 114B2. CCDs 114B1 and 114B2 are mounted so that the imaging surfaces of CCDs 114B1, 114B2 intersect at right angles with the optical axis of the optical path from prisms 117B1, 117B2, respectively. Thus, CCD 114B1 and 114B2 are each mounted with the imaging surface inclined at a predetermined angle with respect to longitudinal axis 133B of the endoscope.

In FIG. 1C, two objective lenses 115C1 and 115C2 are eccentric, for example, to the upper side from the center axis of the lens. Reflecting prisms 117C1 and 117C2 are arranged on the optical axes of the respective objective lenses 115C1 and 115C2. The centers of Prisms 115C1 and 115C2 are positioned at a same height as the respective objective lenses 115C1 and 115C2, but are somewhat displaced in the horizontal direction. Prism 117C1 is somewhat displaced to the left from objective lens 115C1 and the prism 117C2 is somewhat displaced to the right from objective lens 115C2.

The light reflected by each of prisms 117C1 and 117C2 is reflected by the respective slopes of prism 118C to form an image on the imaging surface of CCD 114C fitted to package 113C. Video signals from CCD 114C are transmitted to a video processor external to the endoscope.

In FIG. 1D, a distal end 100D of an endoscope includes two eccentric objective lenses 115D1, 115D2 arranged the same as objective lenses 115C1 and 115C2 in FIG. 1C. The positions of prisms 117D1 and 117D2 are displaced forward and rearward in comparison to prisms 117C1 and 117C2 in FIG. 1C. The light from prisms 117D1 and 117D2 is reflected respectively by mirrors 118D1 and 118D2 to form respective images on CCDs 114D1 and 114D2 mounted adjacently on package 113D, which is parallel to longitudinal axis of the endoscope.

One mirror 118D1 is concave and so forms an image on CCD 114D1 for a somewhat shorter optical path length than the optical path length for the image on CCD 114D2. Hence, in this example, the left optical channel has a shorter optical path length than the right optical channel. Video signals from CCDs 114D1 and 114D2 are transmitted to a video processor external to the endoscope.

FIGS. 1A to 1D illustrate a few ways of capturing a stereo image in the constrained space of an endoscope tip. But since a small outer diameter of the endoscope distal end is desirable, the configurations in these figures also illustrate how difficult it is to capture high quality stereoscopic images in small outer diameter distal-end image capture systems due to many problems.

Consider the configuration in FIG. 1A. To focus this device one has to move the tiny lenses of both objective lenses 115A1 and 115A2 very precisely to obtain focus. The configuration in FIG. 1B suffers from needing to bend the light at an odd angle with a prism. This likely leads to lateral color distortion and uneven performance on the left and right image sensors. The images are not optimally spaced.

The configurations in FIGS. 1C and 1D require the image to lie flat in the plane of the optics. Either the CCD or the optical components cannot lie on the mid-plane of a round endoscope tip thus these configurations require either very small optical components (and a small inter-pupillary distance) or a very small CCD which limits the imaging quality as the area is small thus restricting the number of pixels and/or the pixel size. Also, in the configuration of FIG. 1D, the optical path lengths have different lengths, and so the optical components for each channel must be different.

SUMMARY

An image capture unit with coplanar image capture sensors overcomes shortcomings of the prior art cameras used in the distal end of an endoscope and provides many new capabilities. Each of the coplanar image capture sensors in a channel of the endoscope has a common front end optical structure, e.g., the lens assembly in the image capture unit is the same for each of the sensors. The common optical and coplanar configuration of the image capture sensors eliminates the need for calibration of lens artifacts. Re-registration of different images captured in independent channels of the endoscope is not required. The images captured in a channel of the endoscope are temporally registered. The images are also spatially registered relative to each other.

Visible images of a scene or a visible image of a scene and one or more fluorescence images in the scene are acquired by the image capture unit. A controller enhances the acquired images. The enhanced images are displayed on a stereoscopic display, in one aspect. The enhanced images may include (a) visible images with enhanced feature definition, in which a particular feature in the scene is emphasized to the operator of a minimally invasive surgical system, for example; (b) images having increased image apparent resolution; (c) images having increased dynamic range; (d) images displayed in a way based on a pixel color component vector having three or more color components; and (e) images having extended depth of field.

In one aspect, an image capture unit includes a first image capture sensor with a first sensor surface and a second image capture sensor with a second sensor surface. The first and second sensor surfaces are coplanar. In another aspect, the first surface is in a first plane and the second surface is in a second plane. The first and second planes are parallel, and are separated by a known distance. A beam splitter, in the image capture unit, is positioned to receive light. The beam splitter directs a first portion of the received light to the first sensor surface and passes a second portion of the received light through the beam splitter. A reflective unit, in the image capture unit, is positioned to receive the second portion of the received light and to direct the second portion of the received light to the second image capture sensor.

In one aspect, the first and second image capture sensors are different areas on an image capture sensor chip. In another aspect, the first and second image capture sensors are two separate image capture sensor chips mounted on a common platform. In yet another aspect, the first and second image capture sensors are two separate imaging areas on a single image capture sensor chip.

In one aspect, a distal end of an endoscope includes the first and second image capture sensors, a prism assembly including the beam splitter, and the reflective unit. In another aspect, a stereoscopic endoscope includes a distal end, a pair of channels, and a plurality of first and second image capture sensors, prism assemblies, and reflective assemblies. The first image capture sensor, the second image capture sensor, the prism assembly, and the reflective unit are included in the plurality. Each channel in the pair of channels includes, in the distal end of the stereoscopic endoscope, a different first image capture sensor, a different second image capture sensor, a different prism assembly, and a different reflective unit in the plurality.

In one implementation, the beam splitter is included in a prism assembly that also includes a surface positioned to direct the first portion of light received from the beam splitter onto the first sensor surface. This surface is positioned so that no other light hits the surface. The reflective unit includes a reflective surface positioned to reflect the second portion of the received light onto the surface of the second image capture sensor. In another implementation, the prism assembly and the reflective unit are included in a single integral structure.

In one aspect, the prism assembly includes a distal face through which the received light enters the prism assembly. The image capture unit has a first optical path length from the distal face to the first sensor surface that is about equal to a second optical path length from the distal face to the second sensor surface. In another aspect, the first and second optical path lengths have different lengths and the difference in length of the two optical path lengths is configured to provide a difference in focus between the images acquired by the first image capture sensor and the second image capture sensor.

Independent of the implementation, the prism assembly includes a beam splitter configured to reflect the first portion of the light received by the prism assembly and to transmit the second portion of the received light. In one aspect, the first portion of the received light is a first percentage of the received light, and the second portion of the received light is a second percentage of the received light. In one aspect, the beam splitter is configured so that the first and second percentages are about equal. In another aspect, the beam splitter is configured so that the first and second percentages are not equal. The beam splitter may be implemented in many ways, including but not limited to, thin metallic coatings, dielectric coatings, dichroic coatings, or a pattern of reflective tiles on an otherwise transparent interface.

The first and second image capture sensors can both be color image capture sensors or alternatively, one of the image sensors is a color image sensor and the other of the image captures sensors is a monochrome image capture sensor.

With the image capture unit, a first image from a first portion of light received from a common front end optical system is captured by the first image capture sensor. A second image from a second portion of the light received from the common front end optical system is captured by the second image capture sensor. The first and second image capture sensors are coplanar and the first and second images are registered spatially relative to each other upon being captured.

The same basic geometry for the prism assembly and the reflective unit is used in each of the various aspects to achieve the advantages described above. Depending on the particular enhancement, the configuration of the beam splitter is varied and the illumination source may be varied.

For enhanced feature differentiation, the light received from the lens assembly enters the prism assembly through a distal face. The beam splitter is configured to reflect a first portion of the received light on a basis of a polarization state of the received light, and to transmit a second portion of the received light on the basis of the polarization state of the received light. A first optical path length from the distal face to the first sensor surface is about equal to a second optical path length from the distal face to the second sensor surface. A controller is coupled to the first and second image capture sensors. The controller combines information from a first image captured by the first image capture sensor and information from a second image captured by the second image capture sensor to generate an image increasing the saliency of a feature in the image based on polarization differences in the received light.

For enhanced resolution and dynamic ranges, the beam splitter is configured to reflect a first percentage of the received light, and to transmit a second percentage of the received light. Again, a first optical path length from a distal face of the prism assembly to the first sensor surface is about equal to a second optical path length from the distal face to the second sensor surface.

In one aspect, the first and second image capture sensors are color image capture sensors. Again, the controller is coupled to the first and second image capture sensors. The controller combines information from a first image captured by the first image capture sensor and information from a second image captured by the second image capture sensor to generate an image having one of enhanced spatial resolution and enhanced dynamic range relative to an image captured by a single image capture sensor.

When the first and second percentages are about equal, the controller generated image has enhanced spatial resolution. When the first and second percentages are not about equal, and the controller generated image has enhanced dynamic range.

For the enhanced resolution in one aspect, the first percentage is about fifty percent of the received light and the second percentage is about fifty percent of the received light. The beam splitter and reflective surface of the prism assembly are positioned to offset an image captured by the first image capture sensor from an image captured by the second image capture sensor with the first optical path length remaining about equal to the second optical path length. The controller samples a first pixel in a first image captured by the first image capture sensor and samples a second pixel captured by the second image capture sensor and corresponding to the first pixel. Using information from the two sampled pixels, the controller generates a pixel in an image having increased color performance in comparison to the images captured by the first and second image capture sensors. The controller may perform this process using groups of pixels instead of single pixels.

When the beam splitter separates the received light so that the first percentage and the second percentage are not equal, the first percentage is selected based on the dynamic range of the first image capture sensor, e.g., so that an image captured by the first image capture sensor is not clipped due to the dynamic range of the first image capture sensor. In one aspect, the first percentage is about N % of the received light and the second percentage is about M % of the received light. N and M are positive numbers. One hundred percent minus N % is about equal to M %. The controller samples a pixel in an image captured by the first image capture sensor and samples a corresponding pixel in an image captured by the second image capture sensor. The controller uses the information from the sampled pixels to generate a pixel in an output image. The output image has an increased dynamic range relative to an image captured by a single image capture sensor. The controller may perform this process using groups of pixels instead of single pixels.

In another aspect of enhanced resolution, the light received by the beam splitter includes a plurality of color components. The beam splitter is configured to reflect one color component of the plurality of color components and to transmit other color components in the plurality of color components. The first optical path length from the distal face of the prism assembly to the first sensor surface is about equal to the second optical path length from the distal face to the second sensor surface.

In this aspect, the first image capture sensor is a monochrome image capture sensor, and the second image capture sensor is an image capture sensor having a color filter array for the other color components in the plurality of color components. The controller has full spatial resolution in the one of the plurality of color components and has reduced spatial resolution in the other of the plurality of color components. The controller generates an image having improved spatial resolution and sharpness relative to an image captured by a color image capture sensor.

For aspects including a pixel color component vector having three or more color components, the beam splitter includes a plurality of notch filters. A notch filter is a filter with a spectrally narrow band in which the filter is reflective, and a broader pass band, which may be on one side or both sides of the reflective band. The plurality of notch filters reflects a first set of light components as a first portion of the received light and passes a second set of light components as a second portion of the received light. Again, the first optical path length from the distal face of the prism assembly to the first sensor surface is about equal to a second optical path length from the distal face to the second sensor surface.

The system includes an illuminator that generates output light including a plurality of color components. The controller is configured to receive a demosaiced image of a first image captured by the first image capture sensor, and configured to receive a demosaiced image of a second image captured by the second image capture sensor. The controller generates an N-element color component vector for a pixel in an output image from a color component vector of a corresponding pixel in the first demosaiced image and a color component vector of a corresponding pixel in the demosaiced second image, where N is at least three.

For the extended depth of field aspect, the beam splitter reflects a first portion of the received light and transmits a second portion of the received light. A first optical path length from a distal face of the prism assembly to the first sensor surface is smaller than a second optical path length from the distal face to the second sensor surface. The first image capture sensor captures an image focused at a first object distance, and the second image capture sensor captures an image focused at a second object distance. In one aspect, the controller is coupled to the first and second image capture sensors to receive the first and second images. The controller automatically shifts an output image between the first image and the second image as the object to endoscope distance changes without physically moving the optics inside the endoscope. In another aspect, the controller is configured to sample a region of pixels in the first image and to sample a corresponding region of pixels in the second image to generate pixels in an output image having increased apparent depth of field in comparison to the first and second images individually. In still yet another aspect, the controller combines a first image captured by the first image capture sensor with a second image captured by the second image capture sensor, and generates a third image that automatically stays in focus during physical motion of the endoscope relative to the tissue being viewed. This is accomplished by the controller processing regions of the first and second images and comparing their sharpness. The controller creates the third image from the pixels in the sharper of the two images at each of the regions. The third image is thus constructed from the sharpest portions of the two images.

In a further aspect, the controller retrieves a first image captured by the first image capture sensor and a second image captured by the second image capture sensor, and generates a channel depth map based on the relative sharpness of pixel regions acquired from the first and second image capture sensors. The depth map may be used by the system in various ways. One way is for the controller to generate a three-dimensional surface of a scene and then to project (by executing software) and texture map the first and second images back on the three-dimensional surface to generate a textured virtual image surface. The controller generates a new virtual image for a virtual camera point from the channel depth map and the textured image surface. More than one virtual camera position and corresponding image may be created if desired. For example, real-time images of a scene are generated as the virtual camera position is swept back and forth from a left eye position to a right eye position, i.e., swept back and forth across an interocular separation. When an image from a virtual camera view point is generated, the image is displayed on a non-stereo display unit. The view point is moved to the next virtual camera position, and an image from that view point is generated and displayed. Thus, as the virtual camera position is swept back and forth, the displayed scene rocks back and forth over time and so gives depth cues to a person viewing the display without requiring a stereoscopic viewer.

In yet another aspect, an apparatus includes a first image capture sensor and a second image capture sensor. The first capture image sensor has a first sensor surface, while the second image capture sensor has a second sensor surface. The apparatus also includes a first lens assembly and a second lens assembly. A reflective unit is positioned to receive light that passes through the first lens assembly and is positioned to receive light that passes through the second lens assembly. The reflective unit reflects the received light from the first lens assembly unto the first sensor surface. The reflective unit also reflects the received light from the second lens assembly unto the second sensor surface. A first optical path length from the first lens assembly to the first sensor surface is about equal to a second optical path length from the second lens assembly to the second sensor surface.

In one aspect, the first and second image capture sensor surfaces of this apparatus are coplanar. In another aspect, the first sensor surface is in a first plane. The second sensor surface is in a second plane, and the first and second planes are substantially parallel and are separated by a known distance. In both cases the first optical path length and the second optical path length are about equal.

BRIEF DESCRIPTION OF THE DRAWINGS

FIGS. 1A to 1D are prior art examples of image capture sensor configurations in a distal end of a stereoscopic endoscope.

FIG. 10 is a schematic illustration of a distal end of a stereoscopic endoscope with a surface that directs light received from two lens assemblies to coplanar image sensors.

Figure 2:
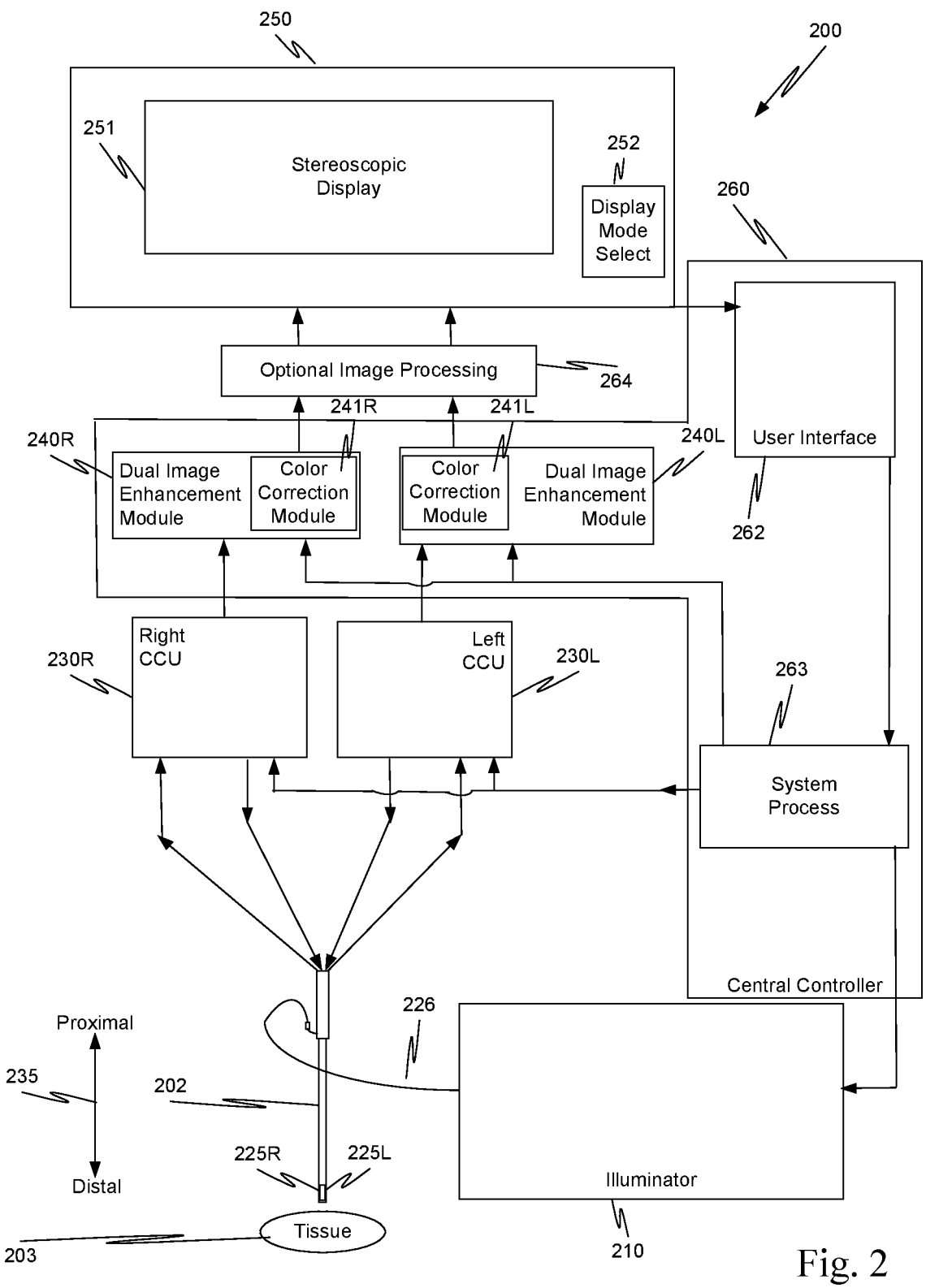
FIG. 2 is a block diagram of a minimally invasive surgical system that includes a plurality of image capture units in a distal end of a stereoscopic endoscope.

In the drawings, the first digit of a reference number indicates the figure in which the element with that reference number first appeared for single digit figure numbers. The first two digits of a reference number indicates the figure in which the element with that reference number first appeared for double digit figure numbers.

DETAILED DESCRIPTION

As used herein, electronic stereoscopic imaging includes the use of two imaging channels (i.e., one channel for left side images and another channel for right side images).

As used herein, a stereoscopic optical path includes two channels (e.g., channels for left and right images) for transporting light from an object such as tissue to be imaged. The light transported in each channel represents a different view (stereoscopic left or right) of a scene in the surgical field. Each one of the stereoscopic channels may include one, two, or more optical paths, and so light transported along a single stereoscopic channel can form one or more images. For example, for the left stereoscopic channel, one left side image may be captured from light traveling along a first optical path, and a second left side image may be captured from light traveling along a second optical path. Without loss of generality or applicability, the aspects described more completely below also could be used in the context of a field sequential stereo acquisition system and/or a field sequential display system.

As used herein, an illumination channel includes a path providing illumination to tissue from an illumination source located away from an image capture unit (e.g., away from the distal end of an endoscope), or an illumination source located at or near the image capture unit (e.g., one or more light emitting diodes (LEDs) at or near the distal end of an endoscope).

As used herein, white light is visible white light that is made up of three (or more) visible color components, e.g., a red visible color component, a green visible color component, and a blue visible color component. If the visible color components are provided by an illuminator, the visible color components are referred to as visible color illumination components. White light may also refer to a more continuous spectrum in the visible spectrum as one might see from a heated tungsten filament or xenon lamp, for example.

As used herein, a visible image includes a visible color component.

As used herein, a non-visible image is an image that does not include any of the visible color components. Thus, a non-visible image is an image formed by light outside the range typically considered visible.

As used herein, images captured as the result of fluorescence are referred to as acquired fluorescence images. There are various fluorescence imaging modalities. Fluorescence may result from natural tissue fluorescence, or the use of, for example, injectable dyes, fluorescent proteins, or fluorescent tagged antibodies. Fluorescence may result from, for example, excitation by laser or other energy source. In such configurations, it is understood that a notch filter is used to block the excitation wavelength that enters the endoscope. Fluorescence images can provide vital in vivo patient information that is critical for surgery, such as pathology information (e.g., fluorescing tumors) or anatomic information (e.g., fluorescing tagged tendons).

As used herein, the angle of incidence is the angle between a light ray incident on a surface and the line perpendicular to the surface at the point of incidence.

As used herein, images are processed digitally and may be re-oriented or mirrored by changing the way in which the image is indexed. Re-orientation or mirroring may also be accomplished in the order in which the image sensor is read.

Aspects of this invention facilitate acquiring visible and non-visible stereoscopic images of a scene in a surgical field. Referring to FIG. 2, for example, image capture units 225L, 225R (FIG. 2) are located at a distal end of a stereoscopic endoscope 202 in a minimally invasive surgical system 200, e.g., a da Vinci® minimally invasive teleoperated surgical system commercialized by Intuitive Surgical, Inc. of Sunnyvale, Calif. As indicated by arrow 235, the distal direction is towards tissue 203 and the proximal direction is away from tissue 203.

One image capture unit 225L captures left side images for a stereoscopic image, sometimes referred to as left side stereoscopic images. A second image capture unit 225R captures right side images for a stereoscopic image, sometimes referred to as right side stereoscopic images.

As described more completely below, each image capture unit includes a lens assembly and a sensor assembly. The lens assembly is sometimes referred to as a front end optical system. The sensor assembly includes a pair of coplanar image capture sensors, in one aspect, a folded optical path that transmits light from the lens assembly to one of the coplanar image capture sensors, and another folded optical path that transmits light from the lens assembly to the other coplanar image capture sensor. The same lens assembly in the image capture unit is used for both image capture sensors so that the image capture sensors are said to have a common front end optical structure. The combination of the shared lens assembly and the coplanar configuration of the image capture sensors eliminates the need for calibration to compensate for lens artifacts. Since the spatial relation between the two image capture sensors is constant, and since the image captures sensors share a common lens assembly, spatial registration of a pair of images captured by the two image capture sensors remains constant over time and during changing optical conditions, such as changing focus. A pair of images captured in a channel of endoscope 202 may also be temporally registered to each other.

In one aspect, image capture units 225L, 225R are used in a minimally invasive surgical system that includes multiple viewing modes: a normal mode, and one or more enhanced modes. A person switches between the viewing modes by using display mode switch 252 that typically is in a user interface 262 presented on a surgeon's control console 250, sometimes referred to as surgeon's console 250.

In the normal viewing mode, visible images of a scene in the surgical field are acquired by image capture units 225L, 225R and displayed in stereoscopic display 251 of a surgeon's control console 250. In an enhanced viewing mode, visible images of the scene or a visible image of the scene and one or more fluorescence images in the scene are acquired by image capture units 225L, 225R, and dual image enhancement modules 240R, 240L in a central controller 260 enhance the acquired images. The enhanced images are displayed in stereoscopic display 251. The enhanced images may include (a) visible images with enhanced feature definition, in which a particular feature in the scene is emphasized to the operator of minimally invasive surgical system 200; (b) images having increased image apparent resolution;

(c) images having increased dynamic range; (d) images displayed in a way based on a pixel color component vector having three or more color components; and (e) images having extended depth of field.

Prior to considering image capture units 225L, 225R and the enhanced modes of operation in further detail, minimally invasive surgical system 200 is described. System 200 is illustrative only and is not intended to limit the application of image capture units 225L, 225R to this specific system. Image capture units 225L, 225R could be implemented in various other devices such as stereoscopic microscopes, monoscopic endoscopes, microscopes, and also could be used for replacement of existing endoscopic cameras.

Minimally invasive surgical system 200, for example, a da Vinci® Surgical System, includes image capture units 225L, 225R. In this example, a surgeon at surgeon's console 250 remotely manipulates endoscope 202 that is mounted on a robotic manipulator arm (not shown). There are other parts, cables, etc. associated with the da Vinci® Surgical System, but these are not illustrated in FIG. 2 to avoid detracting from the disclosure. Further information regarding minimally invasive surgical systems may be found for example in U.S. patent application Ser. No. 11/762,165 (filed Jun. 23, 2007; disclosing Minimally Invasive Surgical System), U.S. Pat. No. 6,837,883 B2 (filed Oct. 5, 2001; disclosing Arm Cart for Telerobotic Surgical System), and U.S. Pat. No. 6,331,181 (filed Dec. 28, 2001; disclosing Surgical Robotic Tools, Data Architecture, and Use), all of which are incorporated herein by reference.

An illuminator 210 is coupled to stereoscopic endoscope 202. Illuminator 210 includes at least a white light source and optionally may include one or more fluorescence excitation sources. Illuminator 210 is used in conjunction with at least one illumination channel in stereoscopic endoscope 202 to illuminate tissue 203. Alternatively and without loss of generality, illuminator 210 may be replaced by an illumination source at the distal tip, or near the distal tip, of endoscope 202. Such distal tip illumination may be provided by LEDs, for example, or other illumination sources.

In one example, illuminator 210 provides white light illumination that illuminates tissue 203 in white light. In some implementations, illuminator 210 can also provide non-visible light that excites fluorescence and as well as a subset of the visible color components that make-up white light.

Typically, three (or more) visible color components make up white light, e.g., white light includes a first visible color component, a second visible color component, and a third visible color component. Each of the three visible color components is a different visible color component, e.g., a red color component, a green color component, and a blue color component. Additional color components may also be used such as cyan to improve color fidelity of the system.

In some implementations, a fluorescence excitation source in illuminator 210 provides a fluorescence excitation illumination component that excites fluorescence in tissue 203. For example, narrow band light from the fluorescence excitation source is used to excite tissue-specific near infrared emitting fluorophores so that fluorescence images of specific features within tissue 203 are acquired by image capture units 225L, 225R.

Light from illuminator 210 is directed onto an illumination channel 226 that couples illuminator 210 to the illumination channel in endoscope 202. The illumination channel in stereoscopic endoscope 202 directs the light to tissue 203. In another aspect, an illumination source, such as LEDs or other sources, is provided at, or near the distal tip on endoscope 202. The illumination channels can be implemented with a fiber optic bundle, a single stiff or flexible rod, or an optical fiber.

Each one of image capture units 225R, 225L in endoscope 202 include, in one aspect, a single lens assembly for passing light received from tissue 203 to a sensor assembly. Light from tissue 203 may include visible spectrum light components reflected from a white light illumination source and fluorescence light (visible or non-visible) that originates at tissue 203, for example as the result of receiving energy from a fluorescence excitation illumination source. The reflected white light components are used to capture an image or images that a viewer would expect to see in the normal visible light spectrum.

Image capture unit 225L is coupled to a stereoscopic display 251 in surgeon's console 250 via a left camera control unit (CCU) 230L. Image capture unit 225R is coupled to stereoscopic display 251 in surgeon's console 250 via a right camera control unit (CCU) 230R. Camera control units 230L, 230R receive signals from a system process module 263 that controls gains, controls capturing images, controls transferring captures images to dual image enhancement modules 240R, 240L, etc. System process module 263 represents the various controllers including the vision system controllers in system 200. Camera control units 230L, 230R may be separate units, or may be combined in a single dual controller unit.

Display mode select switch 252 provides a signal to a user interface 262 that in turn passes the selected display mode to system process module 263. Various vision system controllers within system process module 263 configure illuminator 210 to produce the desired illumination, configure left and right camera control units 230L and 230R to acquire the desired images, and configure any other elements needed to process the acquired images so that the surgeon is presented the requested images in display 251.

Color correction modules 241L and 241R are in some embodiments each part of dual image enhancement modules 240L and 240R, respectively (described in more detail below). Color correction modules 241L and 240L transform the color of the acquired images to a new desired color balance as determined by system process module 263. As shown in FIG. 2, user interface 262, system process module 263, and image enhancement modules 240L, 240R are grouped as a central controller 260 for descriptive purposes. Optional image processing module 264 receives video from central controller 260 and processes images from color correction modules 241L and 241R prior to display on stereoscopic display 251 in surgeons console 250. Optional image processing module 264 is equivalent to image processing modules in prior art minimally invasive surgical systems and so is not considered in further detail.

Figure 3A:
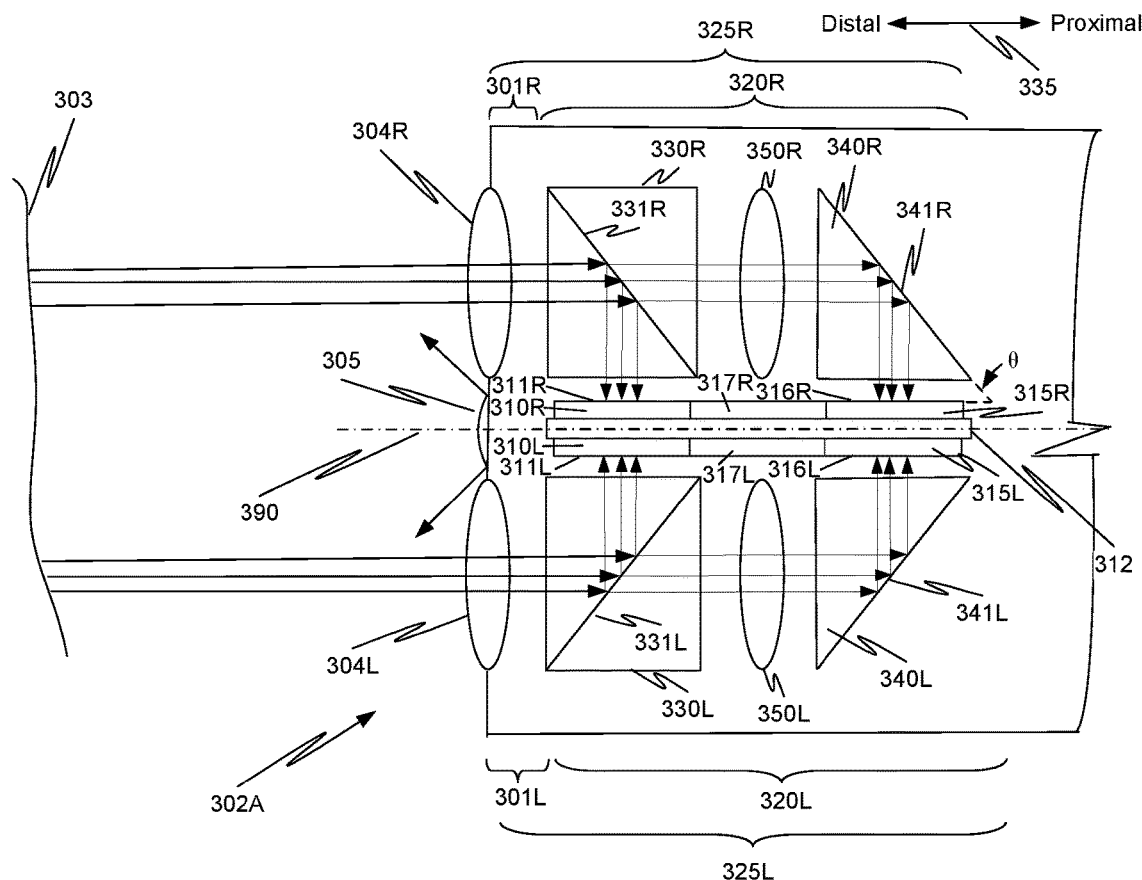
FIG. 3A is a block diagram of a distal end of a stereoscopic endoscope that includes a plurality of image capture units.

FIG. 3A is a block diagram of a distal end of stereoscopic endoscope 302A that includes image capture units 325L and 325R and an illumination channel 305. Each image capture unit 325R, 325L includes a lens assembly 301R, 301L and a sensor assembly 320R, 320L. Sensor assembly 320R, 320L is positioned to receive light that passes through lens assembly 301R, 301L. Each image capture unit 320R, 320L includes a prism assembly 330R, 330L, a reflective assembly 340R, 340L and coplanar image capture sensors (310R, 315R), (310L, 315L), in one aspect. Stereoscopic endoscope 302A is an example of stereoscopic endoscopic 202.

As illustrated in FIG. 3A, each stereoscopic channel in a distal end of stereoscopic endoscope 302A, sometimes referred to as endoscope 302A, has the same component configuration. In this FIG. 3A aspect, image capture unit 325L (for the left stereoscopic channel) and image capture unit 325R (for the right stereoscopic channel) are symmetric with reference to a plane that intersects centerline longitudinal axis 390 of endoscope 302A (i.e., they are positioned as mirror images of each other). As indicated by arrow 335, the distal direction is towards tissue 303 and the proximal direction is away from tissue 303.

Light from one or more illumination channels 305 in endoscope 302A illuminates tissue 303 in this example. While it not shown in FIG. 3A, one or more surgical instruments within the field of view of endoscope 302A may also be illuminated via light from illumination channel 305. The use of an illumination channel in an endoscope is illustrative only and is not intended to be limiting in the various examples presented in this description. The illumination may be provided by an illumination source in the endoscope or by some other apparatus that is internal or external to the endoscope.

Light reflected from tissue 303 and any fluorescence are received by lens assembly 301L and 301R. Lenses 304L and 304R in lens assembly 301L and 301R may include one of more optical components that direct the received light to sensor assembly 320L and sensor assembly 320R, respectively. In other aspects, lens assembly 301L and 301R are folded to reduce the longitudinal length of image capture units 325L and 325R.

Light from lenses 304L and 304R passes to sensor assemblies 320L, 320R, respectively. Within sensor assemblies 320L, 320R, the light is received by beam splitters 331L and 331R, respectively in prism assemblies 330L, 330R. In one aspect, each of beam splitters 331L and 331R is implemented as a buried coated surface 331L, 331R. As explained more completely below, the coating or coatings on each of coated surface 331L, 331R are selected to provide a particular functionality. Coated surface 331L, 331R reflects a first portion of the light received from lens assembly 301L, 301R and transmits a second portion of the received light. For differentiation of features of tissue 303, the coated surface distinguishes between differences in polarization of the light received from lens assembly 301L, 301R. In still other aspects, the coated surface includes notch filters that also reflect portions of the received light and transmit other portions of the received light.

Irrespective of the implementation of coated surfaces 331L, 331R, beam splitter 331L directs a first portion of the received light onto a first image capture sensor 310L, e.g., onto a surface 311L of image capture sensor 310L, in image capture unit 325L and transmits a second portion of the received light through beam splitter 331L. Similarly, beam splitter 331R directs a first portion of the received light onto a first image capture sensor 310R, e.g., onto a surface 311R of image capture sensor 310R, in image capture unit 325R and transmits a second portion of the received light through beam splitter 331R.

In the example of FIG. 3A, light passed through beam splitters 331L and 331R is received by an optional lens 350L and 350R, respectively. Lenses 350L and 350R focus the received light to account for the optical path length to image capture sensors 315L and 315R. Lenses 350L and 350R are optional.

The light from lenses 350L and 350R is received by reflective assemblies 340L and 340R, respectively. Reflective unit 340L directs the received light onto a second image capture sensor 315L, e.g., directs the received light onto a surface 316L of image capture sensor 315L, in image capture unit 325L. Similarly, reflective unit 340R directs the received light onto a second image capture sensor 315R, e.g., directs the received light onto a surface 316R of image capture sensor 315R, in image capture unit 325R. In each of the aspects described herein, the light is directed onto a surface of an image capture sensor and so for brevity it is said that the light is directed onto the image capture sensor.

Each of reflective assemblies 340L and 340R includes a reflective surface 341L, 341R, e.g., a mirror surface, which reflects the received light. In the example of FIG. 3A, apparatuses 340L and 340R are each implemented as a prism with one face having a reflective coating, or are each implemented using total internal reflection on the hypotenuse of the prism. In one aspect, an angle θ formed by the intersection of a plane including reflective surface 341R and a plane including surface 311R of image capture sensor 310R and surface 316R of image capture sensor 315R is a forty-five degree angle and so the prism is referred to as a forty-five degree prism. Surface 341R of a forty-five degree prism exhibits total internal reflection when the medium proximal to surface 314R is air and so surface 341R is a reflective surface.

Image capture sensors 310L and 315L are coplanar, i.e., top sensor surfaces 311L and 316L are effectively in the same plane. Bottom surfaces of sensors 310L and 315L are on a plane defined by a first surface of platform 312. Similarly, image capture sensors 310R and 315R are coplanar, e.g., top surfaces 311R and 316R are effectively in the same plane. Bottom surfaces of sensors 310R and 315R are on a plane defined by a second surface of platform 312. Platform 312 may be composed of two planar parts, e.g., two ceramic parts bonded along axis 390. The first surface of platform 312 is opposite and removed from the second surface of platform 312.

In one aspect, a first semiconductor die 317R including two image capture sensors 310R, 315R is mounted on a first ceramic platform. A second semiconductor die 317L including two image capture sensors 310L, 315L is mounted on a second ceramic platform. The two ceramic platforms are then bonded together to form platform 312. Wires to the two dies 317R, 317L are passed through a channel or channels in platform 312. The use of two image capture sensors in a die is illustrative only and is not intended to be limiting. In some aspects, the two image sensors are in separate dies. (See FIG. 9.) The two image capture sensors may be part of one large image capture sensor in the die, and pixels of the image capture sensor between image capture sensor 310R and image capture sensor 315R, for example, are ignored.

In some aspects, platform 312 may not be used and the two sets of image capture sensors are included in a single structure configured to provide the necessary connections to power, control, and video cables. Also, the use of the two coplanar image capture sensors in an image capture unit as shown in FIG. 3A is only illustrative and is not intended to be limiting. For example, in some aspects, more than two coplanar image capture sensors could be used, e.g., multiple beam splitters could be used in a line and the reflective unit placed at the proximal end of the line.

The coplanar configuration of the image capture sensors eliminates the need for calibration to compensate for lens artifacts and re-registration of different images captured by image captures sensors 310R/315R (first pair) and 310L/315L (second pair). As described above, the spatial relation between the two image capture sensors within a given pair is constant, and since the image captures sensors within a given pair share a common lens assembly, i.e., a common front end optical structure, spatial registration of a pair of images captured by the two image capture sensors remains constant over time and during changing optical conditions, such as changing focus.

Figure 3B:
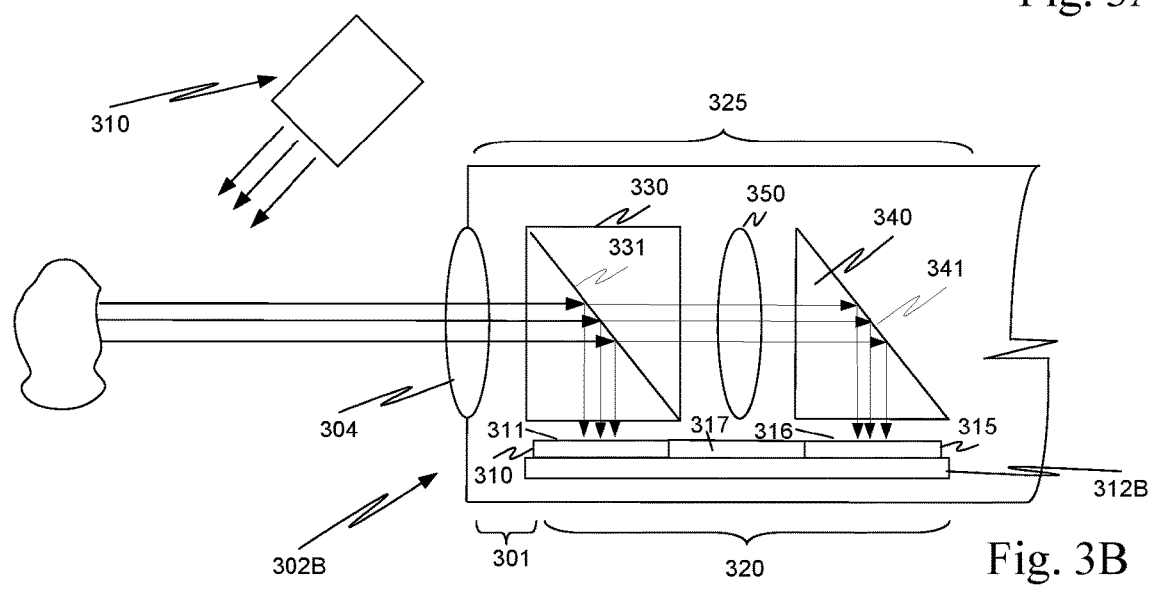
FIG. 3B is a block diagram of a distal end of a monoscopic endoscope that includes an image capture unit.

FIG. 3B is similar to FIG. 3A, except endoscope 302B is a monoscopic endoscope, and the illumination is provided by an illuminator external to and not connected to endoscope 302B. However, in some aspects the illuminator is mounted on endoscope 302B. In endoscope 302B, elements 301, 304, 320, 330, 331, 340, 341, 350 310, 311, 315, 316, and 312B of image capture unit 325 are the same as elements 301L, 304L, 320L, 330L, 331L, 340L, 341L, 350L, 310L, 311L, 315L, 316L, and 312, respectively, and so the description of these elements is not repeated. An illumination source external to the endoscope may be used for the various described endoscope embodiments and aspects rather than, or in addition to, an illumination channel inside or mounted on the endoscope.

Figure 4A:
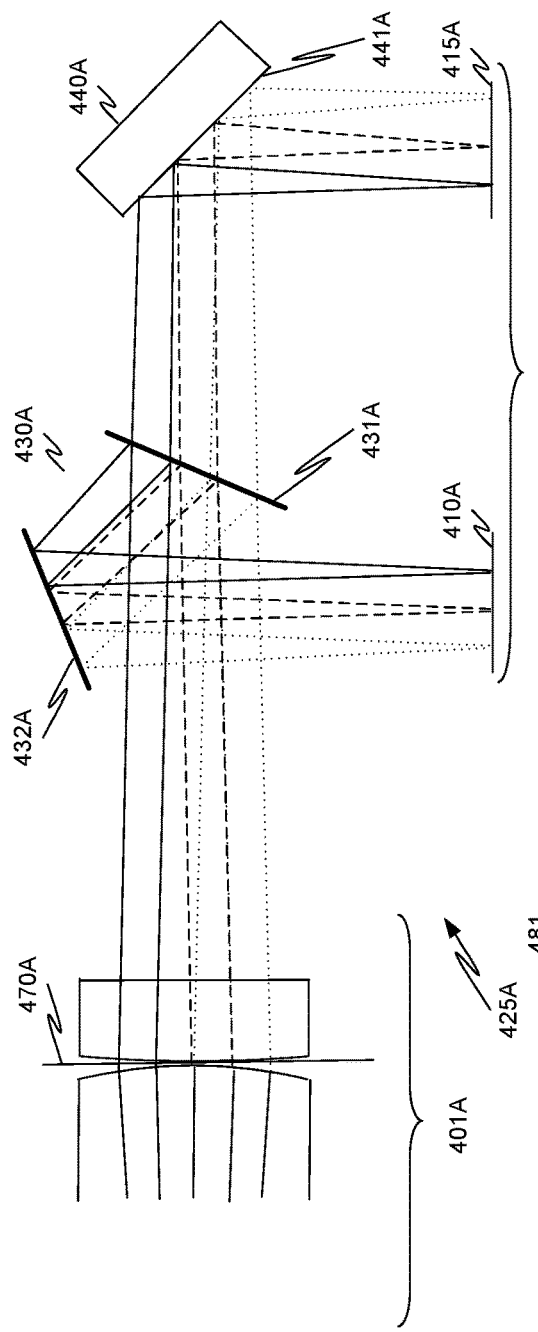
FIG. 4A is an illustration of a portion of an image capture unit that includes a lens assembly and a sensor assembly having coplanar image capture sensors.

FIG. 4A is an illustration of a portion of an image capture unit 425A that includes a lens assembly 401A and a sensor assembly 420A. Sensor assembly 420A includes a prism assembly 430A, a reflective unit 440A, and coplanar image capture sensors 410A, 415A, in one aspect. Lens assembly 401A includes a plurality of optical elements including an optical element that defines an optical stop 470A, sometimes referred to as stop 470A. As used herein, a stop is a plane in space having an aperture or a place in an optical path where the chief ray has a height of zero. Light passing through stop 470A is received by a beam splitter 431A in prism assembly 430A of image capture unit 425A.

A stereoscopic apparatus would include two image capture units as illustrated in FIG. 4A. However, as demonstrated above with respect to FIG. 3A, the left and right stereoscopic channels with image capture units are symmetric, and so only a single channel and image capture unit is described to avoid duplicative description. The other channel including the image capture unit is symmetric across a plane intersecting the longitudinal axis of the endoscope with the channel illustrated in FIG. 4A.

Beam splitter 431A is positioned to receive light that passes through stop 470A. Beam splitter 431A is configured to direct a first portion of the received light to a first image capture sensor 410A, and to pass a second portion of the received light through the beam splitter to reflective unit 440A. In this example, beam splitter 431A in prism assembly 430A is implemented as a coated first surface. Thus, beam splitter 431A is sometimes referred to as coated first surface 431A. Coated first surface 431A separates the received light into the two portions.

Coated first surface 431A reflects the first portion of the received light to a second surface 432A that in turn directs, e.g., reflects, the light onto first image capture sensor 410A. Coated first surface 431A transmits the second portion of the received light through coated first surface 431A to reflective unit 440A. In one aspect, the angle of incidence of the light to coated surface 431A is less than forty-five degrees.

Second surface 432A is positioned so that no light other than the light reflected by coated first surface 431A hits second surface 432A. In one aspect, second surface 432A is a reflective surface that is implemented as one of a coated surface and a total internal reflection surface.

Reflective unit 440A includes a third surface 441A that reflects the light received from beam splitter 431A onto a second image capture sensor 415A. In one aspect, third surface 441A is a reflective surface implemented, for example, as one of a coated surface and a total internal reflection surface.

Image capture sensors 410A and 415A are coplanar. In one aspect, a first optical path length from stop 470A to coated first surface 431A to second surface 432A to image capture sensor 410A is about equal to a second optical path length from stop 470A through coated first surface 431A to coated surface 441A to image capture sensor 415A. In another aspect, the first and second optical path lengths are not equal. The unequal optical path lengths can be implemented by adjusting the spatial relationship between a surface in reflective unit and the beam splitter in the prism assembly, as described more completely below.

Figure 9:
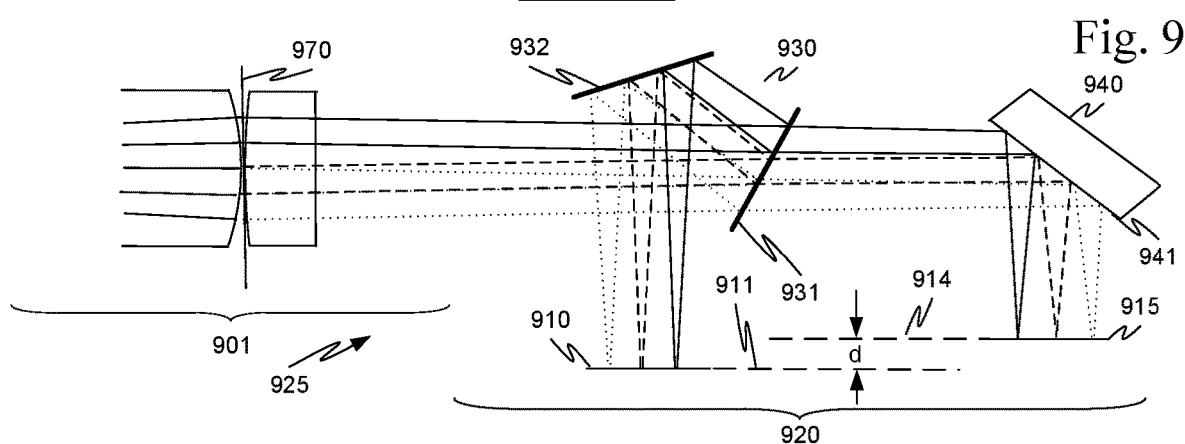
FIG. 9 is an illustration of a portion of an image capture unit that includes a lens assembly and a sensor assembly having image capture sensors that are not coplanar.

Alternatively, image capture sensor 410A has a top sensor surface in a first plane and image capture sensor 415A has a top sensor surface in a second plane, where the first and second planes are parallel and are separated by a known distance (See FIG. 9). In this alternative arrangement of the image capture sensors, the optical path lengths to the two image capture sensors can be either about equal or unequal. The top sensor surface of an image capture sensor is the surface of the image capture sensor that receives light from at least one optical component in the sensor assembly. Optional optics, as illustrated by lenses 350 (FIG. 3) may be used in the second optical path to sensor 415A, for example.

Herein, about equal or substantially equal means that the two optical path lengths are equal within the tolerances associated with manufacturing and mounting the various optical path elements. Also, the definition of the optical path lengths as starting at stop 470A is illustrative and is not intended to be limiting. The optical path lengths could also be variously defined, such as with respect to a distal face of prism assembly 430A through which the received light enters prism assembly 430A, with respect to a first element in the lens assembly, or with respect to coated first surface 431A.

Figure 4B:
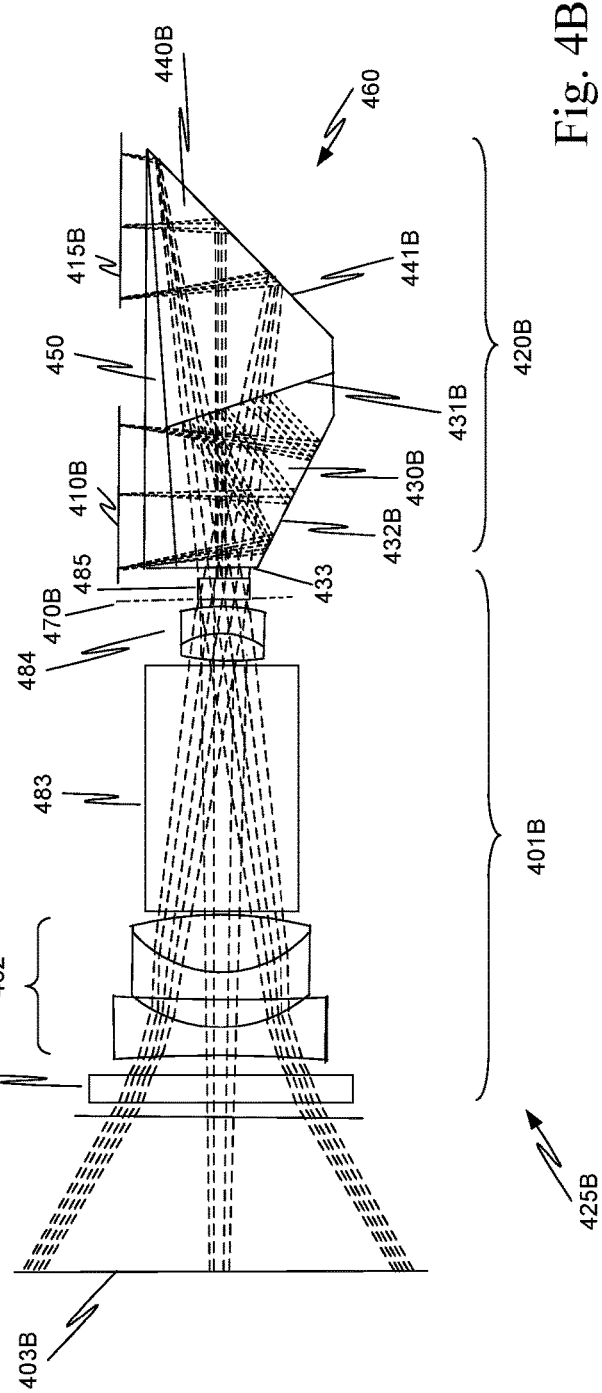
FIG. 4B is an example of an implementation of the structure in FIG. 4A using a pentaprism as the prism assembly.

In FIG. 4A, the separation of prism assembly 430A, reflective unit 440A, and image capture sensors 410A, 415A is not to scale. In actual use, prism assembly 430A and reflective unit 440A are mostly solid glass and there is a small gap between the glass structures and image capture sensors 410A, 415A. FIG. 4B is an example of an implementation of the structure in FIG. 4A using prisms.

FIG. 4B is an illustration of an image capture unit 425B in distal end of a stereoscopic endoscope. Image capture unit 425B includes a shared lens assembly 401B and a sensor assembly 420B. Sensor assembly 420B includes a prism assembly 430B, a reflective unit 440B, and coplanar image capture sensors 410B, 415B, in one aspect. Sensor assembly 420B is positioned to receive light that passes through lens assembly 401B. The other image capture unit (not shown) includes components equivalent to those shown in FIG. 4B. The two image capture units are symmetric across a plane that intersects the longitudinal axis of the stereoscopic endoscope in a way equivalent to that shown in FIG. 3A.

Light from an illuminator is reflected by tissue, or fluorescence originating from tissue is represented by plane 403B. The light enters lens assembly 401B through a window 481 and then passes through a first set of lenses 482, a prism 483, a second set of lenses 484, and an aperture element 470B that implements the stop.

Element 485 is optional and is illustrative of various features, either singly or in combination, that may be incorporated into the various lens assembly embodiments at various positions. In one aspect, element 485 represents a window for notch filters to block fluorescence excitation wavelengths. In another aspect, element 485 represents a focusing element.

In another aspect, element 485 represents a plano-plano element. In yet another aspect, element 485 represents a structure that includes liquid crystal cells that function as a variable focus lens when a control voltage is applied to the liquid crystal cells. The control voltage dynamically changes the refractive index profile of the material the light passes through. The liquid crystal cells can adjust the focus to a desired focal distance from infinity to ten centimeters with good optical performance. A liquid crystal cell having these performance characteristics is available as the LensVectorm AutoFocus element from LensVector, Inc. of Mountain View, Calif., US. (LENSVECTOR is a trademark of Lens-Vector, Inc. in the United States.)

In some aspects, element 485 represents one or more filters to preprocess the light that is received by the other elements in the lens assembly. Alternatively, the filter or filters can be attached to the distal end surface of the endoscope, or the filter or filters may be inserted between aperture element 470B and prismatic structure 460.

In this aspect, prismatic structure 460 is an integral prismatic structure (two prisms or more are joined without any gaps between the prisms) that includes a prism assembly 430B with beam splitter 431B and a reflective unit 440B with a reflective surface 441B. In one aspect, prismatic structure 460 is designed with a material with a particular refractive index and prism geometry to achieve the desired image separation onto the two image capture sensors. The design of prismatic structure 460 starts out as a multi-face prism and is then optimized to accommodate the sensor spacing, and the desired maximal outer tube diameter of the stereoscopic endoscope, which restricts the prism geometry.

In the aspect illustrated in FIG. 4B, prism assembly 430B includes a pentaprism with at least two coated surfaces 431B and 432B. Alternatively, surface 432B may not be coated and may use total internal reflection. A beam splitter, i.e., coated first surface 431B, separates the received light into the two portions. Coated first surface 431B reflects the first portion of the received light to second surface 432B that in turn directs, i.e., reflects, the light onto first image capture sensor 410A. Coated first surface 431B transmits the second portion of the received light through surface 431A to reflective unit 440B. Prism 450 is optional and is provided to facilitate handling and mounting of prismatic structure 460.

The pentaprism is a reflecting prism used to deviate a beam of light by ninety degrees. The light beam reflects inside the pentaprism twice, which allows the transmission of the light beam through a right angle without producing an inverted or reversed image. Typically, a pentaprism has a periphery made up of five sides. A pentaprism is a constant deviation prism in that the pentaprism deviates the optical path through the same angle irrespective of the orientation of the pentaprism to the optical path. Herein, a pentaprism may be bonded or otherwise jointed to or positioned with respect to other prisms or optics.

In one aspect, coated first surface 431B is a multi-layer buried coated surface. The surface is coated with a multi-layer coating, e.g., a multi-layer dichroic coating, metallic coating, or a rugate coating, which has the desired reflective and transmission properties, as discussed more completely below. The angle of incidence of the light with surface 431B is less than forty-five degrees, in one aspect, although this is not a requirement. Second surface 432B is positioned so that no light other than the light reflected by coated first surface 431B hits second surface 432B.

Distal end surface 433, sometimes referred to as a distal face, is the end of prismatic structure 460 and of prism assembly 430B through which the light received from lens assembly 401B enters. In one aspect, first, second, and third surfaces 431B, 432B and 441B are positioned so that a first optical path length from distal end surface 433 to image capture sensor 410B is about equal to a second optical path length from distal end surface 433 to image capture sensor 415B. In another aspect, surface 441B is positioned so that the two optical path lengths are not equal by a small amount.

Reflective unit 440B, in one aspect, is a prism with a surface 441B having a reflective coating or surface 441B is used at such an angle to afford reflection via total internal reflection. In one aspect, an angle formed by the intersection of a plane including reflective surface 441B and a plane including a top sensor surface of image capture sensor 415B is a forty-five degree angle and so the prism is referred to as a forty-five degree prism. In this example, prismatic structure 460 is an integral structure formed by gluing three parts together using known techniques. As noted previously, the three parts are designed with materials, refractive index, and prism geometry to achieve the desired image separation on image capture sensors 410B and 415B. The use of three parts is illustrative only and is not intended to be limiting. For example, prismatic structure 460 could be an integral structure formed using two parts.

Image capture sensors 410B and 415B are coplanar and in one aspect are mounted on a platform on which the coplanar image sensors for the other lens assembly are also mounted (See FIG. 3A). In some aspects, the two image capture sensors are included in a single structure.

Stop 470B is placed or formed near or inside prismatic structure 460 to reduce the size of prismatic structure 460 and to reduce the angle of incidence of corner rays onto image capture sensors 410B, 415B. Stop 470B may be positioned either distally (as shown) or proximally of element 485

For the example aspects shown in FIG. 4B, middle element 483 in lens assembly 401B may be a prism. In some aspects this prism is positioned to create a folded optical path to create an endoscope with, for example, a field of view oriented at 30 degrees to the endoscope's longitudinal axis. This fold happens in a plane perpendicular to the plane of image capture sensors 410B, 415B.

Referring again to FIGS. 2, 3A, 3B, 4A, and 4B, various aspects of an image capture unit are shown and described. The image capture unit includes a lens assembly that receives light from an object to be imaged. The front end optical path through the lens assembly may be straight or may be folded to provide various angled fields of view for the endoscope. Light from the lens assembly travels to a sensor assembly. Various optional optical components (apertures, filters, focusing elements, and the like) may be placed in the lens assembly, or as design limits allow, such optical components may be inserted in an optical path or paths of the sensor assembly.

In one aspect, the sensor assembly includes two or more coplanar image capture sensors. These coplanar image capture sensors are arranged lengthwise along the endoscope. For example, with two coplanar image capture sensors, one of the image capture sensors is positioned relatively closer to the lens assembly (towards the endoscope's distal end), and one of the image capture sensors is positioned relatively farther away from the lens assembly (away from the endoscope's distal end). Thus, the image capture sensors are in a plane generally parallel to the endoscope's centerline longitudinal axis. In one aspect the image capture sensors are both formed as image capture regions (e.g., CMOS image capture regions; alternatively, CCD regions may be used) on the same semiconductor substrate. This single substrate therefore has a length at least about twice its width, and so it can be positioned within the endoscope for space use efficiency, since the sensor regions are arranged lengthwise in the endoscope. Alternatively, the image capture sensors may be individually formed and positioned on a support platform or substrate that is arranged in the endoscope in a way similar to the single sensor substrate arrangement.

Inside the sensor assembly, light received from the lens assembly is split into two or more beams at a beam splitter. In a two sensor implementation, for example, one of the beams travels from the beam splitter along one optical path to be incident on the first image capture sensor, and the other beam travels along another optical path to be incident on the second image capture sensor. The optical paths in the sensor assembly are folded so that light that is incident on the image capture sensors is generally perpendicular to light received from the lens assembly. In some aspects, the optical paths in the sensor assembly are arranged to be substantially equal length so that the lens assembly affects the images captured on the optical sensors in substantially the same way. Various combinations of reflective surfaces, either coated surfaces or total internal reflection surfaces may be used to define the image capture assembly optical path geometries. In some aspects, prisms are used to simplify reflective surface alignment requirements for the image capture sensors.

In some aspects a single image capture unit is used in an endoscope, and so the endoscope has a monoscopic capability. In other aspects, however, two image capture units are used in an endoscope to provide stereoscopic capability. One image capture unit provides left stereoscopic image capability and the other image capture unit provides right stereoscopic image capability. In some aspects, the image capture sensors in the two image capture units are oriented back-to-back so that the sensors are generally towards the center of the endoscope. This arrangement allows an efficient use of lateral space in an endoscope, since the front end objective paths for the two image capture units are positioned to provide good stereoscopic separation and the image capture sensor circuitry can be consolidated. In some aspects the back-to-back image capture sensors are supported by a single platform or substrate to provide further space savings and better optical alignment (e.g., the two image capture units can be aligned with one another prior to incorporation into the endoscope). The back-to-back image capture sensors may be positioned generally along the endoscope's centerline longitudinal axis, although in some aspects they may be offset from the endoscope's centerline longitudinal axis due to, for example, other distal end endoscope features that may be used. Alternatively, two image capture units may be positioned so that the coplanar image capture sensors are facing one another, or so that the coplanar image capture sensors for one image capture unit are coplanar with the coplanar image capture sensors of the other image capture sensor (i.e., all image capture sensors are coplanar, in some instances on the same substrate). Various other orientations of the image capture sensor planes between the two image capture units may be used. It should also be understood that although the one or more image capture units are generally described as being at the endoscope's distal end, in some aspects the one or more image capture units may be at the endoscope's proximal end.

As described in more detail below, the compact dual imaging image capture unit optical geometry allows two relatively large image sensors to be placed in an endoscope for each desired optical channel, and the image capture unit feature that splits the incoming light into two or more beams allows many different visual display features to be presented to a person using an imaging system. For example, if two image capture units are used, two sets of precisely aligned stereoscopic images may be captured, with one stereoscopic image set having the characteristics captured from the first light beam and the other stereoscopic image set having the characteristics captured from the second light beam.

Enhanced Feature Differentiation

In images of a scene from a surgical site, one problem sometimes encountered is saturation when trying to enhance the images presented to the surgeon on surgeons control console 250. One reason is that surgical instruments in the field of view typically reflect more light than tissue. Another issue is identifying features of interest, e.g., nerves, diseased tissue, etc., in the scene that may not be directly on the surface of the tissue.

In one aspect, the imaging of the scene is enhanced by using prismatic structure 460 and coplanar image capture sensors 410B, 415B to gather additional information about the way the illumination interacts with tissue and other objects in the field of view. In particular, the polarization state of the illumination light is perturbed differently by the tissue surface, subsurface structures in the tissue, and surgical instruments.

There are at least two ways to implement the enhanced feature differentiation capability on the illumination side. Either the illumination can be predominantly polarized or predominantly unpolarized. As is known to those knowledgeable in the field, light is never fully polarized, and so predominantly polarized means polarized to the extent that is required for differentiation, e.g., ideally better than 1,000:1 although lower contrast ratios may suffice. Similarly, predominantly unpolarized means unpolarized to the extent that is required.

Enhanced Feature Differentiation—Unpolarized Illumination

Figure 5A:
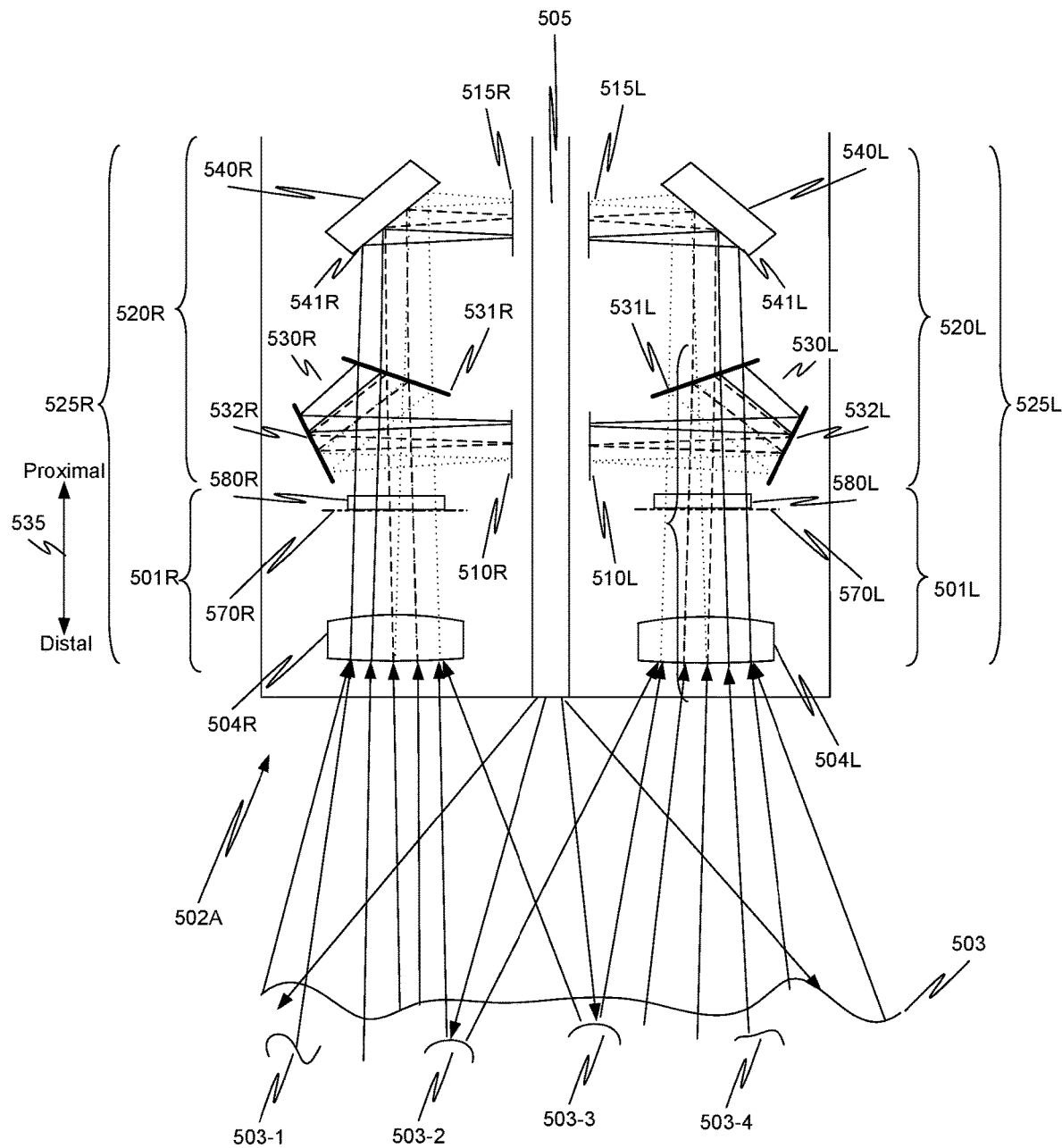
FIG. 5A is a schematic illustration of a distal end of a stereoscopic endoscope including an illumination channel, which provides unpolarized light from an illuminator, and left and right stereoscopic optical channels that each includes an image capture unit having a lens assembly and a sensor assembly.

FIG. 5A is a schematic illustration of a distal end of a stereoscopic endoscope 502A with an image capture unit 525L, 525R and an illumination channel 505, which provides unpolarized light from an illuminator. As indicated by arrow 535, the distal direction is towards tissue 503 and the proximal direction is away from tissue 503.

Each image capture unit 525R, 525L includes a lens assembly 501R, 501L and a sensor assembly 520R, 520L. Sensor assembly 520R, 520L is positioned to receive light passed through lens assembly 501R, 501L. Each sensor assembly 520R, 520L includes a prism assembly 530R, 530L, a reflective unit 540R, 540L, and coplanar image capture sensors (510R, 515R), (510L, 515L), in one aspect. Stereoscopic endoscope 502A is sometimes referred to as endoscope 502A.

Some of the illumination from illumination channel 505 is reflected at the surface of tissue 503. While it is not shown in FIG. 5A, some of the illumination from illumination channel 505 also may be reflected by surgical instruments within the field of view of endoscope 502A. Some tissues impart a degree of polarization in the reflected light from those tissues.

In the following description, the optical paths in the right channel of stereoscopic endoscope 502A are described. The optical paths through the left channel of stereoscopic endoscope 502A are equivalent to those in the right channel due to the symmetry of endoscope 502A, and so in the following description, the left channel reference numeral is included within parentheses following the description of an element in the right channel. This indicates that the description is also applicable to the corresponding element in the left channel.

The reflected light from tissue 503, polarized and unpolarized, passes through lens element 504R (504L) in lens assembly 501R (501R) to stop 570R (570L). The elements in lens assembly 401B (FIG. 4B) are an example of lens element 504R (504L). In this example, an optional quarter wave plate 580R (580L) is inserted in the optical path between stop 570R (570L) and the distal end surface of image capture unit 525R (525L). In another aspect (not shown), quarter wave plate 580R (580L) is not included in the optical path.

The light that passes through stop 570R (570L) is received by sensor assembly 520L (520R) and enters a prism assembly 530R (530L) that includes beam splitter 531R (531L). Beam splitter 531R (531L) is a polarization based beam splitter, in this aspect. Beam splitter 531R (531L) is configured to reflect a first portion of the received light on a basis of a polarization state of the received light and to transmit a second portion of the received light on the basis of a polarization state of the received light. In one aspect, beam splitter 531R (531L) is a coated surface.

For example, unpolarized light entering prism assembly 530R (530L) is evenly divided between first image capture sensor 510R (510L) and second image capture sensor 515R (515L) by beam splitter 531R (531L). Light linearly polarized entering prism assembly 530R (530L) is reflected or transmitted by beam splitter 531R (531L) according to the relative orientation of the polarization of the light and the coating orientation of surface 531R (531L). In the orthogonal cases, all the polarized light is directed to either first image capture sensor 510R (510L) or second image capture sensor 515R (515L). In one aspect, the angle of incidence of the light to coated surface 531R (531L) is less than forty-five degrees.

Coated first surface 531R (531L) reflects the first portion of the received light to a second surface 532R (532L) that in turn directs, e.g., reflects, the light onto first image capture sensor 510R (510L). Second surface 532R (532L) can be either a coated surface or a total internal reflection surface. Second surface 532R (532L) is positioned so that no light other than the light reflected by coated first surface 531R (531L) hits second surface 532R (532L).

Coated first surface 531R (531L) transmits the second portion of the received light through surface 531R (531L) to reflective unit 540R (540L). Specifically, the light transmitted through coated first surface 531R (531L) is received by a third surface 541R (541L) of reflective unit 540R (540L) that in turn directs, e.g., reflects, the light onto second image capture sensor 515R (515L). Surface 541R (541L) can be either a coated surface or a total internal reflection surface.

In one aspect, prism assembly 530R (530L) and reflective unit 540R (540L) are included in a prismatic structure. The prismatic structure, in this aspect, is equivalent to prismatic structure 460 (FIG. 4B) with buried coated surface 431B having a buried multi-layer polarization selective layer, as described more completely below. Thus, the description of prismatic structure 460 is applicable to the prismatic structure used in the aspect of FIG. 5A.

Coated first surface 531R (531L) is, for example, a buried multi-layer polarization beam splitter. Such layers are known to those knowledgeable in the field, and are commonly used in polarizing beam splitter cubes. These dielectric film based coatings are usually buried and such coatings are used in one aspect. Alternatively, a polarization based beam splitter may be constructed with materials from Moxtek® Incorporated of Orem Utah, a Polatechno Co. Ltd of Japan company, as a PBF02 polarizing beam splitter. (MOXTEK is a registered U.S. trademark of Moxtek® Incorporated of Orem Utah.)

Image capture sensors 510R (510L) and 515R (515L) are coplanar. In one aspect, a first optical path length from stop 570R (570L) to coated first surface 531R (531L) to second surface 532R (532L) to image capture sensor 510R (510L) is about equal to a second optical path length from stop 570R (570L) through coated first surface 531R (531L) to third surface 541R (541L) to image capture sensor 515R (515L). Also, the definition of the optical path lengths as starting at stop 570R (570L) is illustrative and is not intended to be limiting. The optical path lengths could also be variously defined, such as with respect to a distal face of prism assembly 530R (530L) through which the received light enters prism assembly 530R (530L), with respect to a first element in lens assembly 501R (501L), or with respect to coated first surface 531R (531L).

Coplanar image capture sensors 510R (510L) and 515R (515L) have a common optical path length through the front end optical structure in lens assembly 501R (501L) and about the same optical path length to each image capture sensor in sensor assembly 520R (520L). One image capture sensor 510R (510L) captures an image comprised of light reflected by polarization beam splitter 531R (531L). Other image capture sensor 515R (515L) captures an image comprised of light transmitted by polarization beam splitter 531R (531L)

Image capture unit 525R (525L) images two polarization states (either orthogonal linear states, or with quarter wave plate 580R (580L), left and right circularly polarized states). In this case, the images acquired by image capture unit 525R (525L) provide information based on the preferential polarization imparted by the structures in the tissue itself. Image capture unit 525R (525L) can only capture the relative strength of two orthogonal components of the polarization state of the received light (not the entire polarization nature of the light.) However, this is sufficient to provide useful information.

For example, light is preferentially polarized when the light is specularly reflected from a surface. The degree of the polarization (and the state of the polarization) depends on the illumination angle and the surface reflectance properties of the surface.

In a clinical setting, this enables reduction in some specular reflections. The reflected light that enters image capture unit 525R (525L) is separated on the basis of the linear polarization and two images are captured. The reflections off shiny tools in the captured images can be identified and reduced by executing software, because such reflections appear in one captured image and not the other captured image. This process works because the light reflected by the shiny tools is partially polarized. This process results in the reduction of specular reflections in the image presented to the surgeon on stereoscopic display 251.

In one aspect, dual image enhancement module 240R (240L) (FIG. 2) processes the images captured by image capture sensors 510R (510L) and 515R (515L) (FIG. 5A) to reduce the reflection from surgical instruments. Information from pixels in the second image captured by image capture sensor 515R (515L) is used to modify pixels in the first image captured by image capture sensor 510R (510L), e.g., a percentage of the pixel value in the second image is subtracted from the corresponding pixel value in the first image, to further reduce the brightness of pixels representing the surgical instrument. In one aspect, the percentage is empirically determined. This is possible because the two images have the same front end optical structure and are registered spatially relative to each other and are registered temporally relative to each other.

Additionally, some tissues impart a degree of polarization in the light reflected by the tissue, for example, long stringy tissues may impart polarization to the reflected light. In this aspect, dual image enhancement module 240R (240L) (FIG. 2) processes the pixels in the second image captured by image capture sensor 515R (515L) from the received polarized light, and may, for example, false color the pixels. The false colored image is then combined with the first image from image capture sensor 510R (515L) and the combined image is sent to stereoscopic display 251 for viewing by the surgeon. In this context, "false color" is a good thing; it enables the particular pixels of interest to be visually salient relative to the background.

In addition, or alternatively, dual image enhancement module 240R (240L) (FIG. 2) processes the pixels in the second image captured by image capture sensor 515R (515L) from the received polarized light, and then determines corresponding pixels in the first image captured by image capture sensor 510R (510L). Dual image enhancement module 240R (240L) changes the properties of the corresponding pixels in the first image, e.g., makes them more transparent and then combines the first and second images. The combined image is sent to stereoscopic display 251 for viewing by the surgeon. Since tissue that did not polarize the incident light is now more transparent, this allows the surgeon to more clearly identify, the tissue that polarized the incident light and so provides additional cues for tissue differentiation. Thus, the combined image generated by dual image enhancement module 240R (240L) increases the saliency of a feature in the image based on polarization differences in the received light, e.g., makes the feature more visible by making overlying tissue more transparent and by reducing other specular reflections.

Since the image capture sensors in an image capture unit are coplanar, the sets of image capture sensors in the two image capture units are in a fixed constant relationship to each other. Also, lens assemblies for each of the image capture units are equivalent. Thus, there is no need for active registration when processing the various images to assure that the images viewed by the surgeon are aligned and form proper stereoscopic images. This reduces the processing required of the images relative to images that are captured without these characteristics.

Enhanced Feature Differentiation—Polarized Illumination

Figure 5B:
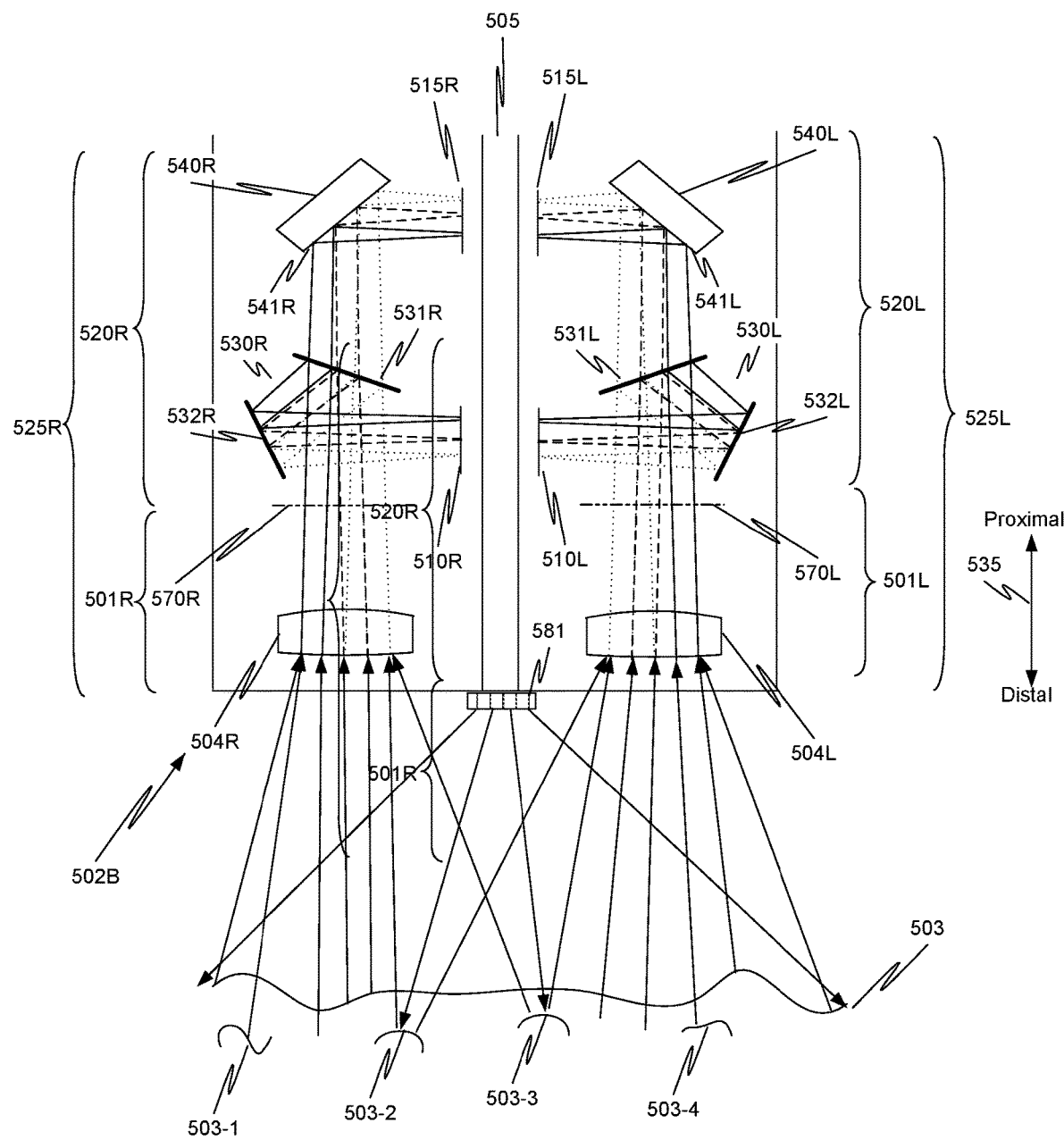
FIG. 5B is a schematic illustration of a distal end of a stereoscopic endoscope including an illumination channel that provides unpolarized light from an illuminator, a polarizer that polarizes the illumination from the illumination channel, and left and right stereoscopic optical channels that each includes an image capture unit having a lens assembly and a sensor assembly.

FIG. 5B is a schematic illustration of a distal end of a stereoscopic endoscope 502B with an image capture unit 525R, 525L and an illumination channel 505 that provides light from an illuminator. As indicated by arrow 535, the distal direction is towards tissue 503 and the proximal direction is away from tissue 503.

Each image capture unit 525R, 525L includes a lens assembly 501R, 501L and a sensor assembly 520R and 520L. Sensor assembly 520R and 520L is positioned to receive light passed through lens assembly 501R, 501L. Each sensor assembly 520R, 520L includes a prism assembly 530R, 530L, a reflective unit 540R, 540L, and coplanar image capture sensors (510R, 515R), (510L, 515L), in one aspect. Also, stereoscopic endoscope 502A is sometimes referred to as endoscope 502A.

A polarizer 581 that polarizes the illumination is provided in the illumination optical path length. In FIG. 5B, polarizer 581 is shown at the distal end of stereoscopic endoscope 502A, but this illustrative only and is not intended to be limiting to this location. Polarizer 581 represents a polarizer in the path of the illumination and can be placed at an appropriate place in that path. Alternatively, illumination channel 505 can deliver light from a polarized source, or polarized light source can be located at location 581.

In the following description, the optical paths in the right channel of stereoscopic endoscope 502B are described. The optical paths through the left channel of stereoscopic endoscope 502B are equivalent to those in the right channel, and so in the following description, the left channel reference numeral is included within parentheses following the description of an element in the right channel. This indicates that the description is also applicable to the corresponding element in the left channel.

The light from tissue 503, polarized and unpolarized, passes through lens element 504R (504L) and stop 570R (570L). Again, the elements in lens assembly 401B (FIG. 4B) are an example of lens element 504R (504L). In this example, optional quarter wave plate 580R (580L) (FIG. 5A) between stop 570R (570L) and the distal end surface of sensor assembly 520R (520L) has been removed. However, in other aspects described below, the quarter wave plate is included in the lens assembly.

The light that passes through stop 570R (570L) is received by sensor assembly 520L (520R) and enters prism assembly 530R (530L) through a distal face. As described above, polarization beam splitter 531R (531L) in prism assembly 530R (530L) is configured to reflect a first portion of the received light on a basis of a polarization state of the received light and to transmit a second portion of the received light on the basis of a polarization state of the received light.

In this example, polarization beam splitter 531R (531L) is configured to direct one polarization state onto first image capture sensor 510R (510L) and to transmit, e.g., pass, the remaining light to reflective unit 540R (540L) that in turn directs the transmitted light onto image capture sensor 515R (515L). Thus, the description of prism assembly 530R (530L), polarization beam splitter 531R (531L), reflective unit 540R (540L) and image capture sensors 510R (510L) and 515R (515L) is not repeated and the above description with respect to FIG. 5A is incorporated herein by reference.

Some of the polarized illumination from polarizer 581 reflects from the surface of tissue 503. The light reflected on the surface has approximately the same polarization as the polarized illumination, e.g., the top surface reflection retains a greater portion of the original polarization state of the light hitting tissue 503.

Light that is not reflected at the surface enters into tissue 503 and interacts with features 503-1 to 503-4, which are below the surface of tissue 503 and which modify the polarization of the incident light. The light that enters into tissue 503 is scattered or absorbed. Some of the scattered light exits the surface of tissue 503 and appears as reflected light at lens element 504R (504L). Thus, some of the light that exits tissue 503 provides additional information in the captured images due to the change in polarization. Therefore, when illuminating with polarized light and imaging with a polarization sensitive detector, the light which has a polarization different from the polarization of the illumination, e.g., light that is depolarized, must have interacted with the sub-surface of tissue 503.

For example, if the illumination is linearly polarized, the light is progressively depolarized as it enters and reflects back from subsurface features 503-1 to 503-4 of tissue 503. The reflected light from the subsurface features 503-1 to 503-4 is essentially depolarized.

Hence, with the appropriate orientations of polarizer 581 and coated first surface 531R (531L), image capture sensor 515R (515L) captures an image from light primarily reflected from the surface of tissue 503 and approximately fifty percent of the light from subsurface features 503-1 to 503-4. Image capture sensor 510R (510L) captures an image from light that was primarily reflected from subsurface features 503-1 to 503-4 and does not capture a significant portion of the light from surface 503. Sensor assemblies 520R (520L) can only capture the relative strength of two orthogonal components of the polarization state of the received light (not the entire polarization nature of the light.) However, this is sufficient to provide useful information.

In particular, the use of polarized illumination in conjunction with polarization sensitive imaging enables one to selectively reduce the surface layer from the tissue in the imaging process. In this aspect, dual image enhancement module 240R (240L) (FIG. 2) processes the pixels in the first image captured by image capture sensor 510R (510L) from the received light, and then determines corresponding pixels in the second image captured by image capture sensor 515R (515L). Dual image enhancement module 240R (240L) can, under the control of input from user interface 262, adjust what is shown in stereoscopic display 251. For example to see just surface 503, image enhancement module 240R (240L) subtracts the image captured by image capture sensor 510R (510L) from the image captured by image capture sensor 515R (515L). The resulting image is sent to stereoscopic display 251 for viewing by the surgeon. Alternatively, to show subsurface features 503-1 to 503-4 in response to input from user interface 262, image enhancement module 240R (240L) scales the image captured by image capture sensor 510R (510L) to achieve similar brightness to the image being displayed on stereoscopic display 251. The resulting image is sent to stereoscopic display 251 for viewing by the surgeon.

Since surface tissue that did not change the polarization of the incident light is now more transparent, this allows the surgeon to more clearly identify the sub-surface features that changed the polarization of the incident light and so provides additional cues for tissue differentiation. Thus, the enhanced image generated by dual image enhancement module 240R (240L) increases the saliency of a feature in the image based on polarization differences in the received light.

Additionally, if the illumination is circularly polarized, reflections from the top surface of tissue 503 are reflected with the handedness of the polarization reversed. In sensor assembly 520R (520L), if the reflected light enters through a quarter wave plate (see quarter wave plate 580R in FIG. 5A) and is then separated on the bases of the linear polarization, the top surface reflection is significantly reduced and reflections off shiny tools are also reduced. Sub surface tissue layers still progressively depolarize the light enabling the surface layers to be presented to the surgeon in such a way as to appear more translucent than before. This enables the ability to better differentiate tissue layers, tissue types, or disease states which manifest themselves below the surface of tissue 503. Thus, a surgeon has the ability to preferentially see "through" the top surface of tissue 503 as the reflection from that top layer can be suppressed, as previously described, by making the top layer more transparent and by reducing specular reflections. Additionally, just the top surface of tissue 503 may be seen as described above.

Examples of tissue features this technique may accentuate may include endometriosis. This technique also may enhance the ability to differentiate nerves which have polarization signatures. Thus, in various clinical settings, the combined image generated by dual image enhancement module 240R (240L) increases the saliency of a feature in the image based on polarization differences in the received light.

Enhanced Resolution and Dynamic Range

While the prior art cameras at the distal end of an endoscope provided stereoscopic color images, the cameras were limited to the resolution and dynamic range provided by the single CCD that captured an image in each stereoscopic channel. As with conventional cameras on a stereoscopic endoscope, the resolution was limited by the number of pixels of the CCDs and the color filter array. Since it is not practical to increase the number of pixels on the CCDs given the limited space available in the distal end of a stereoscopic endoscope, further increasing the resolution was not practical.

Similarly, the center of a scene of a surgical site is typically much brighter than the periphery of the scene. This could result in the captured image being clipped (in intensity) if the range of brightness in the captured image exceeded the dynamic range of the CCD. Image capture units 625R, 625L (FIG. 6A) eliminate the problems of the prior art by providing both higher apparent resolution and higher dynamic range as described more completely below.

Figure 6A:
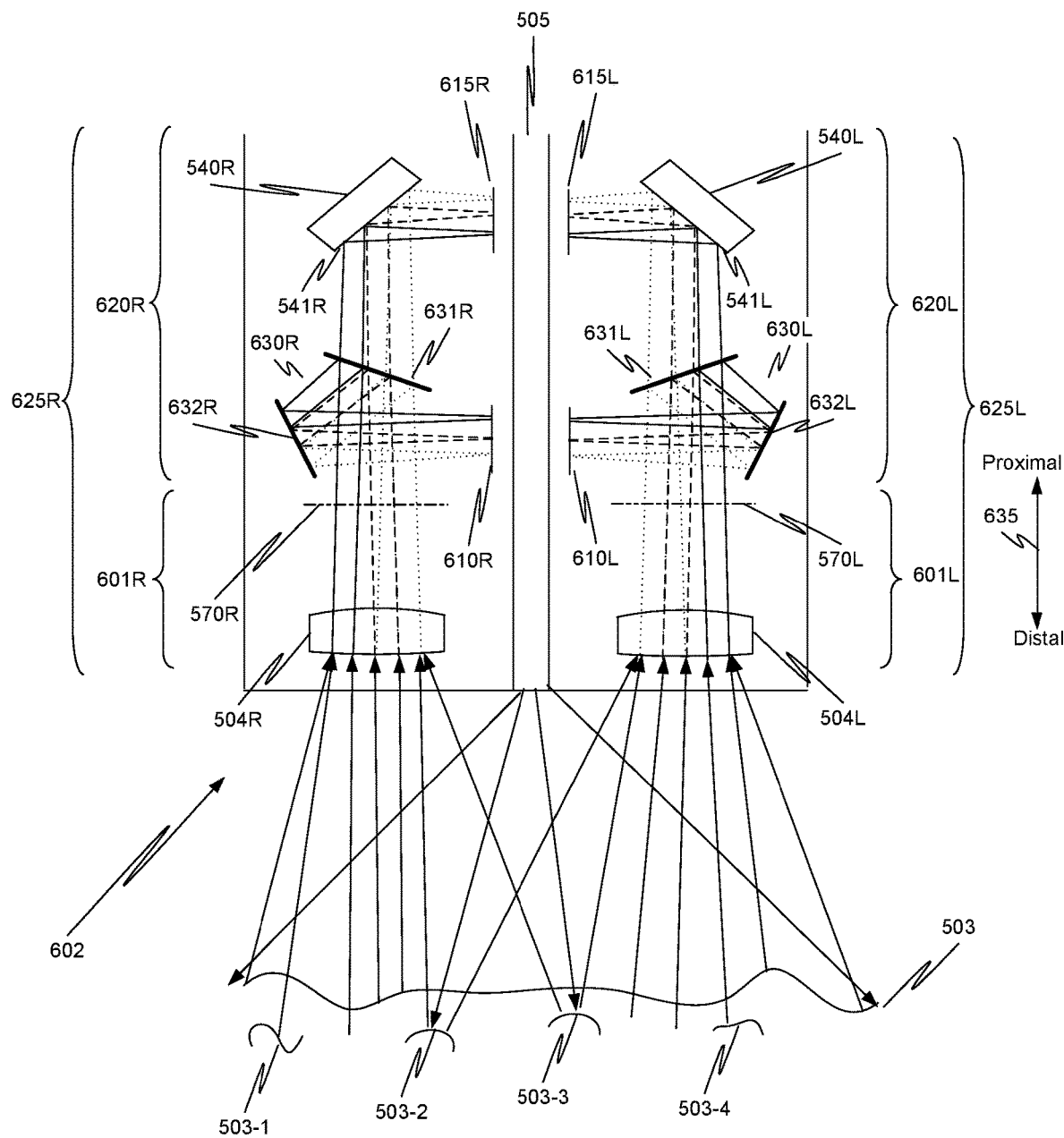
FIG. 6A is a schematic illustration of a distal end of a stereoscopic endoscope, an illumination channel that provides light from an illuminator, and left and right stereoscopic optical channels that each includes an image capture unit having a lens assembly and a sensor assembly. Each sensor assembly includes a beam splitter with a coated surface that reflects a first percentage of the received light and that passes a second percentage of the received light through the coated surface.

FIG. 6A is a schematic illustration of a distal end of a stereoscopic endoscope 602 with an image capture unit 625L, 625R and an illumination channel 505 that provides light from an illuminator. As indicated by arrow 635, the distal direction is towards tissue 603 and the proximal direction is away from tissue 603.

Each image capture unit 625R, 625L includes a lens assembly 601R, 601L and a sensor assembly 620R and 620L. Sensor assembly 620R, 620L is positioned to receive light that passes through lens assembly 601R, 601L. Each sensor assembly 620R, 620L includes a prism assembly 630R, 630L, a reflective unit 640R, 640L, and coplanar image capture sensors (610R, 615R), (610L, 615L), in one aspect. Stereoscopic endoscope 602 is sometimes referred to as endoscope 602.

In the following description, the optical paths in the right channel of stereoscopic endoscope 602 are described. The optical paths through the left channel of stereoscopic endoscope 602 are equivalent those in the right channel due to the symmetry of endoscope 602, and so in the following description, the left channel reference numeral is included within parentheses following the description of an element in the right channel. This indicates that the description is also applicable to the corresponding element in the left channel. Also in FIG. 6A, elements with the same reference numeral as elements in FIGS. 5A and 5B are the same or equivalent elements to those previously described with respect of FIGS. 5A and 5B. To avoid repetition, elements with the same reference numeral are not described again in detail with respect to FIG. 6A.

The light from tissue 503 passes through lens element 504R (504L) and stop 570R (570L) in lens assembly 501R (501L). The elements in lens assembly 401B (FIG. 4B) are an example of lens element 504R (504L). The light received by sensor assembly 620L (620R) enters prism assembly 630R. Prism assembly 630R (630L) includes a beam splitter 631R (631L), e.g., a coated first surface, that reflects a first percentage of the light received by prism assembly 630R (630L) and that passes a second percentage of the received light through the coated first surface, e.g., through beam splitter 631R (631L) to reflective unit 540R (540L).

The light reflected by coated first surface 631R (631L) is received by a second surface 632R (632L) that in turn directs, e.g., reflects, the light onto first image capture sensor 610R (610L). Second surface 632R (632L) is, for example, one of a coated surface, and a total internal reflection surface. The light transmitted through coated first surface 631R (631L) is received by a third surface 541R (541L) of reflective unit 540R (540L) that in turn directs, e.g., reflects, the light onto second image capture sensor 615R (615L).

Second surface 632R (632L) is positioned so that no light other than the light reflected by coated first surface 631R (631L) hits second surface 632R (632L). In one aspect, the angle of incidence of the light to coated first surface 631R (631L) is less than forty-five degrees.

In one aspect, prism assembly 630R (630L) and reflective unit 540R (540L) are included in a prismatic structure with a pentaprism that includes prism assembly 630R (630L). The prismatic structure in this aspect is equivalent to prismatic structure 460 (FIG. 4B) with buried coated surface 431B configured to reflect a first percentage of the received light and to pass through the coated surface a second percentage of the received light. Thus, the description of prismatic structure 460 is applicable to the prismatic structure used in the aspect of FIG. 6A.

In one aspect, the first and second percentages are about equal. In another aspect, the first and second percentages are different. Thus, prism assembly 630R (630L) includes a beam splitter implemented as a coated first surface 531R (531L) that separates the received light into the two portions-(i) a first percentage of the received light sometimes referred to as a first portion, and (ii) a second percentage of the received light, sometimes referred to as a second portion.

Image capture sensors 610R (610L) and 615R (615L) are coplanar. In one aspect, a first optical path length from stop 570R (570L) to coated first surface 531R (531L) to second surface 632R (632L) to image capture sensor 610R (610L) is about equal to a second optical path length from stop 570R (570L) through coated first surface 631R (631L) to a third surface 541R (541L) to image capture sensor 615R (615L). Again, the definition of the optical path lengths as starting at stop 570R (570L) is illustrative and is not intended to be limiting. The optical path lengths could also be variously defined, such as with respect to a distal face of prism assembly 630R (630L) through which the received light enters prism assembly 630R (630L), with respect to a first element in lens assembly 601R (601L), or with respect to coated first surface 631R (631L).

Thus, coplanar image capture sensors 610R (610L) and 615R (615L) have a common optical path length through the front end optical structure in lens assembly 601R (601L) and about the same optical path length to each image capture sensor in sensor assembly 620R (620L). One image capture sensor 610R (610L) captures an image from the first portion of the light received by sensor assembly 620R (620L). Other image capture sensor 615R (615L) captures an image from the second portion of the light received by sensor assembly 620R (620L). As described more completely, below, in one aspect, each of image capture sensors 610R (610L) and 615R (615L) is a color sensor with a color filter array. In another aspect, the color filter array is removed from one of the color sensors and the sensor functions as a monochrome sensor. The color filter array of the other color sensor is modified for the number of color components received by that sensor.

Enhanced Resolution—Example One

In one aspect, coated first surface 631R (631L) of prism assembly 630R (630L) is configured to reflect and to transmit about equal portions of the light received by prism assembly 630R (630L) from lens assembly 601R (601L), i.e., the first and second percentages are about equal. When beam splitter 631R (631L) reflects and transmits about equal portion of light, the beam splitter is referred to as a balanced beam splitter. Each of image capture sensors 610R (610L) and 615R (615L) is a color sensor with a color filter array in this aspect. The color filter array is a Bayer color filter array. Thus, the two Bayer pattern image capture sensors are looking through the same optics at the same scene. Here, a Bayer pattern image capture sensor is a single chip sensor, or part of a single chip, that includes a Bayer color filter array. As noted above, coplanar image capture sensors 610R (610L) and 615R (615L) have a common front end optical structure and about the same optical path length to each sensor.

When prism assembly 630R (630L) and reflective unit 540R (540L) are arranged so that the color images captured by both Bayer pattern image capture sensors 610R (610L) and 615R (615L) are the same, the color image captured by image capture sensor 610R (610L) is the same scene as the color image captured by image capture sensor 615R (615L). Thus, with some static calibration, each point in space in the scene is represented by two pixels-one pixel in the color image captured by image capture sensor 610R (610L) and one pixel in the color image captured by image capture sensor 615R (615L).

Capturing two pixels for each point in space in the scene has several advantages over a normal color image that has one pixel for each point in space in the scene. For example in display 251, pixels that are each based on two pixels for a point in space have reduced noise level and greater apparent resolution. Each output pixel to stereoscopic display 251 from dual image enhancement module 240R (240L) in central controller 260 is based on sampling of two pixels, one from each of the images captured by Bayer pattern image capture sensors 610R (610L) and 615R (615L).

The sampling of two input pixels by dual image enhancement module 240R allows imaging of smaller features than is possible if only an image from a single image capture sensor is processed by central controller 260. Thus, the apparent resolution in the image viewed on stereoscopic display 251 is greater than the resolution in an image viewed on stereoscopic display 251 based on an image captured by a single image capture sensor. Here, the resolution of an image sent to stereoscopic display 251 can be higher than that of the image from a single image capture sensor and so is said to have greater apparent resolution.

Enhanced Resolution—Example Two

In another aspect, coated first surface 631R (631L) of prism assembly 630R (630L) is still configured to reflect and transmit about equal portions of the light received by prism assembly 630R, i.e., the first and second percentages are about equal. Each of image capture sensors 610R (610L) and 615R (615L) is a color sensor with a Bayer color filter array. Again, coplanar image capture sensors 610R (610L) and 615R (615L) have a common front end optical structure and about the same optical path length to each sensor. However, surfaces 631R (631L) and 632R (632L) of prism assembly 630R (630L) are tilted slightly, without changing the total optical path length, so that the image captured by image capture sensor 610R (610L) is offset from the image captured by image capture sensor 615R (615L) by one-half pixel.

Figure 6B:
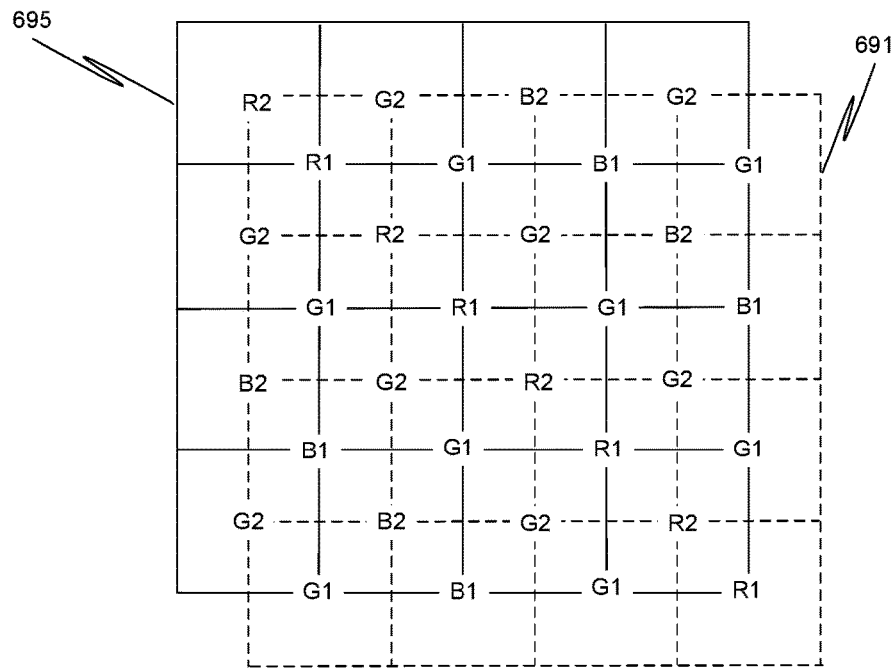
FIG. 6B is a schematic illustration of the offset for a block of pixels in the first image and a corresponding block of pixels in the second image.

In this case, two Bayer pattern image capture sensors are "looking" through the same optics at the same scene. However, the two captured images are offset from one another by a half pixel. FIG. 6B is a schematic illustration of the offset for a block of pixels 691 in the first image and a corresponding block of pixels 695 in the second image. Each pixel in block of pixels 691 is represented by a square having a dashed line perimeter and the color of the pixel is given by the first letter of the color followed by the number 2 at the center of the square. Each pixel in block of pixels 695 is represented by a square having a solid line perimeter and the color of the pixel is given by the first letter of the color followed by the number 1 at the center of the square. In the example, the Bayer color filter array is a red-green-blue-green (RGBG) array.

In one aspect, dual image enhancement module 240R (240L) in central controller 260 interpolates the pixels in the two images to create a color image with higher spatial resolution for the image sent to stereoscopic display 251. The interpolation is equivalent to that done in a three CCD color camera, except unlike the three CCD color camera, two color images are used. The larger number of pixels available for the sampling enhances the apparent resolution and provides improved signal-to-noise performance.

Enhanced Resolution—Example Three

In yet another aspect, coated first surface 631R (631L) of prism assembly 630R (630L) is configured to reflect a first color component in the light received by prism assembly 630R from lens assembly 601R (601L) and to transmit other color components in the received light. In this aspect, image capture sensors 610R (610L) and 615R (615L) are not each a color sensor with a Bayer color filter array.

Rather, image capture sensor 610R (610L) is a monochrome sensor, e.g., a color sensor with the color filter array removed. For purposes of illustration, the light received by sensor assembly 620R (620L) is taken as having a plurality of visible color components—a first visible color component, a second visible color component, and a third visible component. Image capture sensor 615R (615L) is a color sensor with a color filter array for two of the three visible color components, e.g., the number of visible color components in the plurality of visible color components minus one. As noted above, coplanar image capture sensors 610R (610L) and 615R (615L) have a common front end optical structure and about the same optical path length to each sensor.

In this aspect, prism assembly 630R (630L) and reflective unit 540R (540L) are arranged so that the images captured by both image capture sensors 610R (610L) and 615R (615L) are the same scene, but the first image is monochrome and the second image is multi-color. For example, the monochrome image represents the green color component image, and the multi-color image is a red color component and a blue color component image. In this case, color filter array of image capture sensor 615R (615L) is a red and blue checkerboard pattern.

The ratio of green pixels to red and blue pixels is the same as in a Bayer color filter array, but there are twice as many pixels of each color compared to a prior art single color sensor. Thus, the resolution of the green pixels is generated using full spatial sampling by dual image enhancement module 240R (240L) in central controller 260, while the resolution of the red and blue pixels is generated using reduced spatial sampling, relative to the green pixels, by dual image enhancement module 240R (240L). Nevertheless, the spatial sampling for the red and blue pixels in this aspect is the same as the spatial sampling for the green pixels in the prior art single color sensor. This enhanced spatial sampling also provides enhanced apparent resolution and improved signal to noise ratio.

Enhanced Dynamic Range

Typically, surgical site images are similar and have a bright central region and a darker peripheral region. Also, reflections from some surgical instruments are much brighter than reflections from tissue. This results in differences in the range of brightness values that are captured by the image capture sensor in a prior art endoscope. If the brightness values are beyond the dynamic range of the image capture sensor, the values for the pixels are clipped, i.e., set to the highest value of the image capture sensor.

Suppose a scene has a brightness range from 0 to 400. If this scene is imaged to a sensor having a dynamic range from 0 to 100, values over 100 are clipped. For example if the brightness value for a pixel should be 400, the brightness value captured for that pixel is 100. Brightness information is lost for parts of the scene having a brightness larger than 100, because all brightness values greater than 100 are clipped and set to 100. If the gain for the image capture sensor is adjusted to 0.25, the high brightness values are not clipped, but all scene brightness values lower than four are mapped to zero. For this case, the high brightness values are not clipped, but information in the darker parts of the scene is lost. Image capture unit 625R (625L) provides a solution to this problem by preserving both the high brightness information and more of the low brightness information relative to the prior art systems. A brightness range of 0 to 400 is illustrative only. In an actual surgical scene, the brightness variation may be many orders of magnitude. Thus, the dynamic range of the surgical scene is greater than the dynamic range of the image capture sensor. Thus, a single image capture sensor cannot capture the dynamic range of the surgical scene.

Coated first surface 631R (631L), e.g., the beam splitter, of prism assembly 630R (630L) in sensor assembly 620R (620L) is configured to reflect and to transmit different portions of the light received by prism assembly 630R (630L), i.e., the first and second percentages defined above are different. Beam splitter 631R (631L) is a dynamic range adjusted beam splitter in this aspect. A dynamic range adjusted beam splitter reflects M % of the received light and passes N % of the received light, where M % is different from N %. Here, M and N are positive numbers. In one aspect, M % plus N % is equal to about one hundred percent. The equality may not be exact due to light losses and due to tolerances of the various parts of sensor assembly 620R (620L).

In this aspect, each of image capture sensors 610R (610L) and 615R (615L) is a color sensor with a color filter array. The color filter array is a Bayer color filter array in one aspect. Thus, the two Bayer pattern image capture sensors 610R (610L) and 615R (615L) are looking through the same optics at the same scene. Here, a Bayer pattern image capture sensor is a single chip sensor, or part of a single chip, that includes a Bayer color filter array. As noted above, coplanar image capture sensors 610R (610L) and 615R (615L) have a common front end optical structure and about the same optical path length to each sensor. For a pair of coplanar image capture sensors 610R (610L) and 615R (615L) with known dynamic ranges, e.g., the gains of image capture sensors 610R (610L) and 615R (615L) are adjusted to correspond to the configuration of beam splitter 631R (631L).

Typically, the selection of properties of the coating for first surface 631R (631L) considers the brightness of the image captured and/or the brightness of a portion of the image captured, the possible dynamic ranges of image capture sensors 610R (610L) and 615R (615L), and the capabilities of the imaging pipeline. As used here, the imaging pipeline is the portion of central control system 260 (FIG. 2) that processes the captured images and generates output images for stereoscopic display 251. The imaging pipeline may be part of CCU 230R (230L) or part of dual image enhancement module 240R (240L) depending on the implementation chosen.

To assure that no information is clipped in a region of a typical surgical scene that is of importance, a maximum brightness Bmax of the region is empirically determined. The region of importance can be either the complete scene or a portion of the complete scene. The dynamic range of image capture sensor 610R (610L) is then determined, e.g., 0 to S1max. Fraction M of the received light that is reflected by the coating on surface 631R (631L) is selected as:

$M \approx (S1max/Bmax)$

The percentage of the received light M % that is reflected by the coating on first surface 631R (631L) is selected so that dynamic range of light incident on first image capture sensor 610R (610L) is not clipped. Thus, the brightness of pixels in high brightness regions of the image captured by first image capture sensor 610R (610L) are not clipped in this aspect. The percentage of the received light transmitted by the coating on surface 631R (631L) is N %, where N % is about equal to one hundred minus M %. The gain of second image capture sensor 615R (615L) is adjusted so the dynamic range of sensor 615R (615L) is from zero to about N % times maximum brightness Bmax.

As an example, consider a scene that has a maximum brightness Bmax of 400. Image capture sensor 610R (610L) has a dynamic range of 0 to 100. Thus,

M=100/400=¼
M %=25%
N %=75%

Thus, the coating on first surface 631R (631L) is selected to reflect about 25% of the received light and to transmit about 75% of the received light. The gain for image capture sensor 615R (615L) is adjusted to have a dynamic gain of 0 to 300.

The two images captured by sensors 610R (610L) and 615R (615L) are acquired essentially simultaneously. The light received by sensor assembly 620R (620L) is split into two images with a brightness range on sensor 610R (610L) being 0 to 100 (¼ *400) and a brightness range on sensor 615R (615L) being 0 to 300 (¾ *400). Pixels in the high brightness regions of the scene are not saturated in the image captured by sensor 615R (615L). At the same time, the image captured by sensor 610R (610L) preserves and accurately images the darker portions of the scene. Note that in this example scene regions with a brightness of one may be lost if the image capture sensors do not save values less than one. However, this is only one part out of four hundred so is unlikely to be noticed by the surgeon viewing the image on stereoscopic display 251.

In some situations, better results may be obtained by intentionally letting the sensor receiving the most light saturate at the high end. This expands the range at the low end where the other sensor is too dark to register any values.

When prism assembly 630R (630L) and reflective unit 540R (540L) are arranged so that the color images captured by both Bayer pattern image capture sensors 610R (610L) and 615R (615L) are the same scene with different brightness ranges, each point in space in the scene is represented by two pixels-one pixel in the color image captured by image capture sensor 610R (610L) and one pixel in the color image captured by image capture sensor 615R (615L). However, the two pixels have different brightness values that are a linear scale of each other if the brightness value on neither pixel has been clipped.

In this example, the maximum brightness was assumed known. However, in a clinical setting, the structure of stereoscopic endoscope is fixed and not every scene will have the same maximum brightness. Thus, if the configuration just described is used in a scene with a maximum brightness of 500, the pixels for the brightest part of the scene will be clipped. Nevertheless, the dynamic range is still extended over the prior art solutions.

Capturing two pixels with different brightness values for each point in space in the scene has advantages over a normal color image that has one brightness value for each point in space. For example in display 251, pixels that are each based on two pixels for a point in space have reduced noise level for mid brightness regions and the dynamic range is extended compared to the prior art. These advantages are in addition to the spatial resolution advantages described above.

Each output pixel to stereoscopic display 251 from dual image enhancement module 240R (240L) in central controller 260 is based on sampling of two pixels, one from each of the images captured by Bayer pattern image capture sensors 610R (610L) and 615R (615L). As noted above, the sampling of input two pixels by dual image enhancement module 240R (240L) allows imaging of smaller features than is possible if only an image from a single image capture sensor is processed by central controller 260. In addition, in one aspect, a tone mapping process in dual image enhancement module 240R (240L) maps regions of the acquired images to preserve contrast and to match the dynamic output range of stereoscopic display 251. The tone mapping maps the brightness from the captured images to the displayable range while preserving the image contrast and color appearance important to best represent the original scene content. The tone mapping is similar to prior art techniques except that it is enhanced by sampling two pixel values for the same point in space and time instead of one pixel value sequentially.

In the above example, brightness values from 0 to 400 are mapped to the dynamic output range (contrast ratio) of stereoscopic display 251 by the tone mapping. For pixels that are not saturated, the brightness value in the image captured by sensor 615R (615L) is three times the brightness value in the image captured by sensor 610R (610L) for the same point in space. The tone mapping process utilizes this relationship in determining the brightness for a pixel in an image output to stereoscopic display 251. Based on information on the surrounding pixels, tone mapping works on individual groups/regions of pixels to maintain the contrast and thus reduces the noise level and the dynamic range.

The prior art brightness range 0 to 100 has been extended to a brightness range of 1 to 400 for a gain in overall dynamic range performance. Combining the two images and taking advantage of the double sampling further enables reductions in noise in the middle brightness regions along with the increased dynamic range overall.

In the aspect of FIG. 6A and each of the examples described above with respect to FIG. 6A, the image capture sensors in a stereoscopic channel are coplanar. This is illustrative only and is not intended to be limiting. For example, a first of the image capture sensors could have a top sensor surface in a first plane, and a second of the image capture sensors could have a top sensor surface in a second plane. (See FIG. 9.) The first and second planes are parallel to each other and are separated by a known distance. The spacing between the beam splitter and the reflective surface in the reflective unit is adjusted to compensate for the known distance so that the first optical path length to the first image capture sensor is about equal to the second optical path length to the second image capture sensor. Thus, each of the aspects of FIG. 6A described above are directly applicable to this configuration as the two optical path lengths remain about equal.

Enhanced Color Performance

Currently, most imaging system use three visible color components, red, green, and blue (RGB), which is referred to as a three color primary model. Most cameras use a Bayer color filter array image capture sensor with a RGB based color filter array. The three color primary model is also used in most liquid crystal displays (LCDs) and plasma displays.

The three color primary model actually restricts the range of hues, which can be captured by a camera and presented in a display. Using additional color primaries enables the capture and display of more perceptually accurate images. Sharp Electronics Corporation (Sharp) sells light emitting diode (LED) backlit LCD televisions with quad pixel technology. Sharp adds yellow to the conventional red, green and blue color filter array, enabling richer colors to be displayed.

Capturing additional color components in an image by a camera would enable more faithful color reproduction. However, capturing more color components would require changing the conventional Bayer red, green, green, blue (RGGB) color filter array to include the new colors such as yellow and orange, i.e., changing the color filter array to red, orange, green, yellow, green, blue (ROGYGB). However, for an image capture sensor with a given number of pixels, this six component color filter array would reduce the spatial resolution of the camera and would require the development of new masks and dyes suitable for printing on image sensors. The selection of the yellow or orange colors would be optimized in concert with the display.

The use of an appropriate illuminator in combination with image capture units 725R (725L) provides up to a six color component vector per pixel, for example, without reducing the spatial resolution and without requiring the development of new masks and dyes suitable for printing on image sensors. This capability is implemented in a number of ways as described more completely below. The capability not only provides from a three to a six color component vector per pixel after de-mosaicing, but also provides images with an extended depth of field, and also provides enhanced fluorescence imaging capability.

Figures 7B, 7C, 7D, 7E:
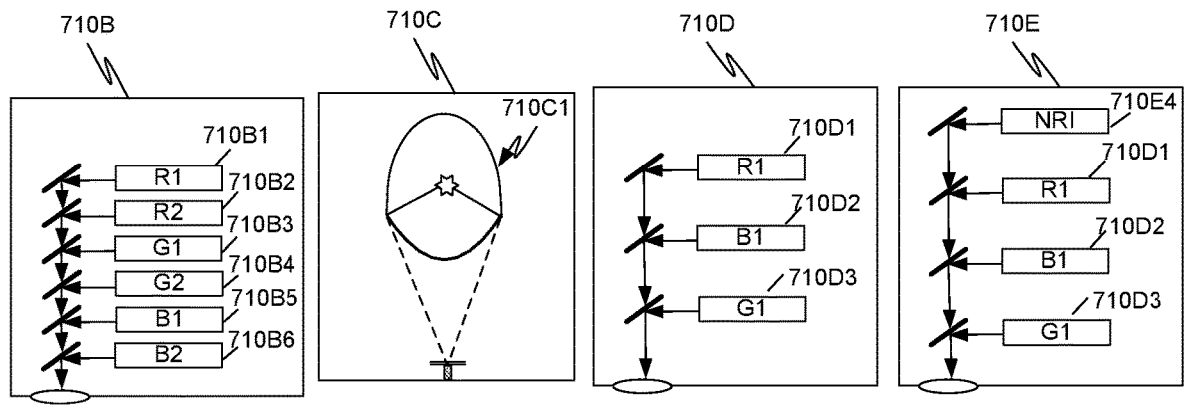
FIGS. 7B to 7E are block illustrations of different illuminators that can be coupled to the stereoscopic endoscope of FIG. 7A as well as to any of the other endoscopes and devices described herein.
Figure 7A:
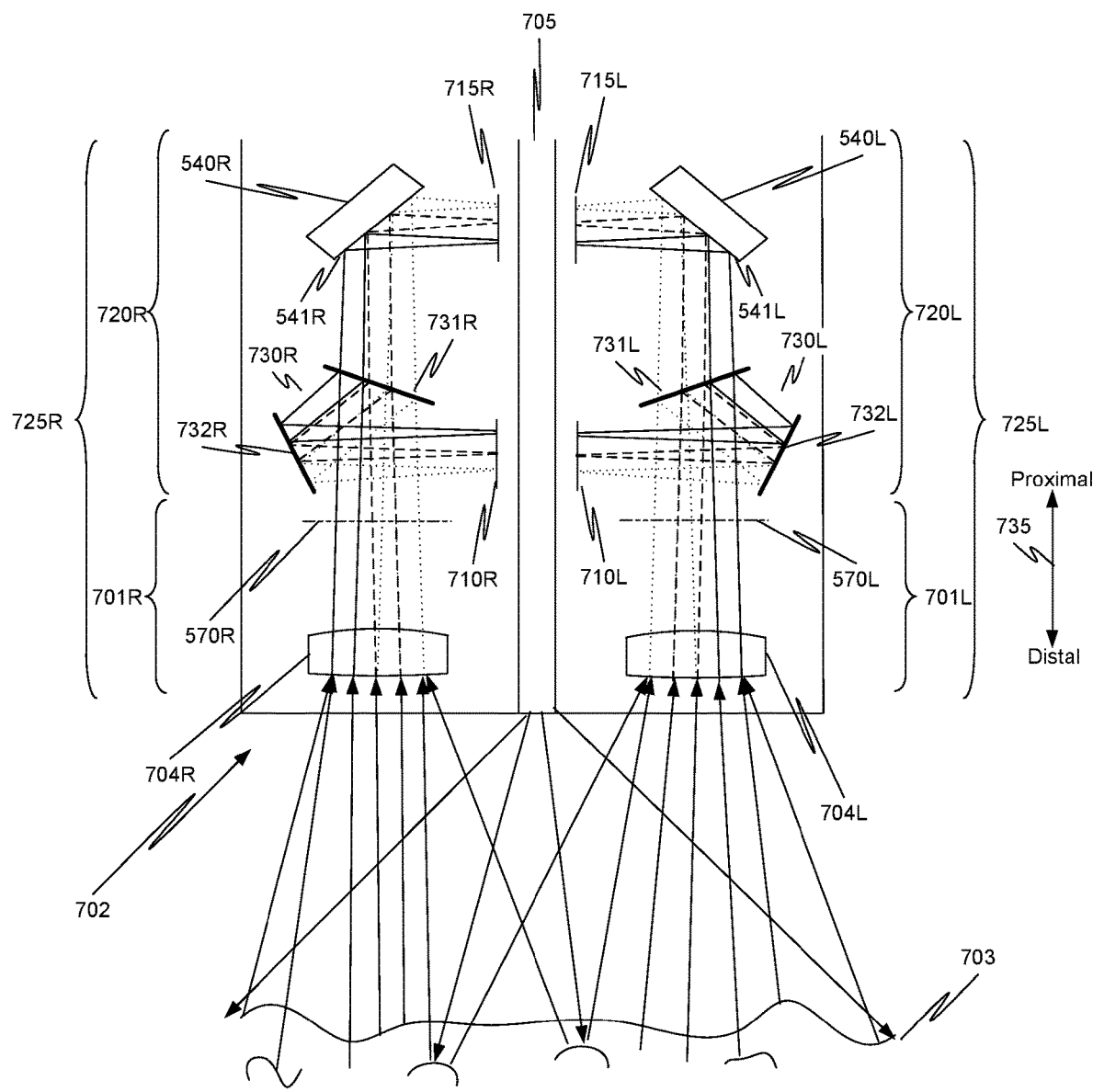
FIG. 7A is a schematic illustration of a distal end of a stereoscopic endoscope including an illumination channel that provides light from one of a plurality of illuminators, and left and right stereoscopic optical channels that each includes an image capture unit having a lens assembly and a sensor assembly.

FIG. 7A is a schematic illustration of a distal end of a stereoscopic endoscope 702 with image capture units 725L, 725R and an illumination channel 705 that provides light from, for example, one of illuminator 710B (FIG. 7B), illuminator 710C (FIG. 7C), illuminator 710D (FIG. 7D) and illuminator 710E (FIG. 7E). See FIG. 2 for an illustration of how the illuminator is coupled to the illumination channel. As indicated by arrow 735, the distal direction is towards tissue 703 and the proximal direction is away from tissue 703.

Each image capture unit 725R, 725L includes a lens assembly 701R, 701L and a sensor assembly 720R, 720L. Sensor assembly 720R, 720L is positioned to receive light that passes through lens assembly 701R, 701L. Each sensor assembly 720R, 720L includes a prism assembly 730R, 730L, a reflective unit 740R, 740L, and coplanar image capture sensors (710R, 715R), (710L, 715L), in one aspect. Stereoscopic endoscope 702 is sometimes referred to as endoscope 702.

In the following description, the optical paths in the right channel of stereoscopic endoscope 702 are described. The optical paths through the left channel of stereoscopic endoscope 702 are equivalent those in the right channel due to the symmetry of endoscope 702, and so in the following description, the left channel reference numeral is included within parentheses following the description of an element in the right channel. This indicates that the description is also applicable to the corresponding element in the left channel. Also in FIG. 7A, elements with the same reference numeral as elements in FIGS. 5A and 5B are the same or equivalent elements to those previously described with respect of FIGS. 5A and 5B. To avoid repetition, elements with the same reference numeral are not described again in detail with respect to FIG. 7A.

The basic structure of image capture units 725L, 725R in each of the different aspects described below is presented in FIG. 7A. The spatial relationships and alignments between prism assembly 730R (730L), reflective unit 540R (540L), image capture sensors 710R (710L), and image capture sensors 715R (715L) are the same for each of the different aspects considered with respect to FIG. 7A. However the coatings on coated first surface 731R (731L) of prism assembly 730R (730L), the type of image capture sensors, and the filters used on the image capture sensors may change in different as aspects, as described more completely below.

The reflected light from tissue 703 passes through lens element 704R (704L) and stop 570R (570L) in lens assembly 701R (701L). The elements in lens assembly 401B (FIG. 4B) are an example of lens element 704R (704L). The light that passes through lens assembly 701R (701L) is received by prism assembly 730R (730L) and enter beam splitter 731R (731L). Beam splitter 731R (731L) is implemented, in this aspect, as a coated first surface that reflects a first portion of the received light, and passes a second portion of the received light to reflective unit 540R (540L).

The light reflected by coated first surface 731R (731L) is received by a second surface 732R (732L) in prism assembly 730R (730L) that in turn directs, e.g., reflects, the light onto first image capture sensor 710R (710L). Surface 732R (732L) can be either a coated surface or a total internal reflection surface. The light transmitted through coated first surface 731R (731L) is received by a third surface 541R (541L) of reflective unit 540R (540L) that in turn directs, e.g., reflects, the light onto second image capture sensor 715R (715L).

Second surface 732R (732L) is positioned so that no light other than the light reflected by coated first surface 731R (731L) hits second surface 732R (732L). In one aspect, the angle of incidence of the light to coated first surface 731R (731L) is less than forty-five degrees.

In one aspect, prism assembly 730R (730L) and reflective unit 740R (740L) are included in a prismatic structure with a pentaprism that includes prism assembly 730R (730L). The prismatic structure in this aspect is equivalent to prismatic structure 460 (FIG. 4B) with buried coated surface 431B including a plurality of notch filters, as described more completely below. Thus, the description of prismatic structure 460 is applicable to the prismatic structure used in this aspect.

In one aspect, the first portion reflected by coated first surface 731R (731L) includes first selected wavelengths of a plurality of color components in the received light, and the second portion transmitted by coated first surface 731R (731L) includes second selected wavelengths of the plurality of color components in the received light. The first selected wavelengths of the plurality of color components in the received light are different from the second selected wavelengths of the plurality of color components in the received light. In one aspect, coated first surface 731R (731L) comprises a plurality of notch filters. The notch filters separate the received light into the first portion and the second portion.

Image capture sensors 710R (710L) and 715R (715L) are coplanar. In one aspect, a first optical path length from stop 570R (570L) to coated first surface 731R (731L) to second surface 732R (732L) to image capture sensor 710R (710L) is about equal to a second optical path length from stop 570R (570L) through coated first surface 731R (731L) to a third surface 741R (741L) to image capture sensor 715R (715L). Again, the definition of the optical path lengths as starting at stop 570R (570L) is illustrative and is not intended to be limiting. The optical path lengths could also be variously defined, such as with respect to a distal face of prism assembly 730R (730L) through which the received light enters prism assembly 630R (630L), with respect to a first element in lens assembly 701R (701L), or with respect to coated first surface 731R (731L).

Thus, coplanar image capture sensors 710R (710L) and 715R (715L) have a common front end optical structure and about the same optical path length to each sensor. A first image capture sensor 710R (710L) captures an image from the first portion of the light received by sensor assembly 720R (720L). A second image capture sensor 715R (715L) captures an image from the second portion of the received light. As described more completely, below, in one aspect, each of image capture sensors 710R (710L) and 715R (715L) is a color sensor with a standard color filter array. In another aspect, the color filter array on one of the color sensors and the sensor function is selected based on the light that is received by endoscope 702.

Controller 260 processes the first and second images captured by image capture sensors 710R (710L) and 715R (715L), respectively, and generates an output image for stereoscopic display 251. Controller 260 generates an N color component vector for each pixel in the output image, where N ranges from three to six. The color component vector for a pixel in the output image is generated from a color component vector of a corresponding pixel (or some combination of pixels) in the first image and a color component vector of a corresponding pixel in the second image. Recall, that each pixel in the output image represents a point in space in the scene captured by the image capture sensors. The pixels in the captured images corresponding to the pixel in the output image are the pixels representing the same point in space.

Enhanced Color Performance—Six Color Component Illumination

In a first aspect, a six color component illuminator 710B (FIG. 7B) is coupled to illumination channel 705 (FIG. 7A). Illuminator 710B includes six laser illumination sources 710B1 to 710B6 that generate red color component R1, red color component R2, green color component G1, green color component G2, blue color component B1, and blue color component B2, respectively. With laser illumination sources, the wavelengths of red color components R1 and R2, green color components G1 and G2, and blue color components B1 and B2 are typically 2 to 5 nanometer (nm) wide instead of about 60 nm per color component from a conventional light emitting diode based illuminator. The configuration of an illuminator with multiple different illumination sources with a mirror for source 710B1 and dichroic mirrors for sources 710B2 to 710B6 is known and so is not considered in further detail herein. See for example, U.S. patent application Ser. No. 12/855,905 (filed Aug. 13, 2010; disclosing Surgical Illuminator with Dual Spectrum Fluorescence), which is incorporated herein by reference.

In this aspect, coated first surface of 731R (731L) of prism assembly 730R (730L) includes a plurality of notch filters. A first notch filter reflects red color component R1 in the received light and transmits red color component R2 in the received light. A second notch filter reflects green color component G1 in the received light and transmits green color component G2 in the received light. A third notch filter reflects blue color component B1 in the received light and transmits blue color component B2 in the received light. The use of three notch filters is for ease of discussion and is not intended to be limiting to three separate filters. In view of this description, one knowledgeable in the field can implement a notch filter with the reflect, transmit properties described here. The coating design would implement the notches. See for example, the "Stopline" and "Quad-Notch" product lines of Semrock Products, Rochester, N.Y.

Hence, coated first surface 731R (731L) reflects red color component R1 in the received light, green color component G1 in the received light, and blue color component B1 in the received light to second surface 732R (732L). Second surface of 732R (732L) reflects red color component R1, green color component G1, and blue color component B1 received from coated first surface 731R (731L) onto image capture sensor 710R (710L).

Coated first surface of 731R (731L) transmits red color component R2 in the received light, green color component G2 in the received light, and blue color component B2 in the received light to third surface 541R (541L) in reflective unit 540R (540L). Third surface of 541R (541L) reflects red color component R2, green color component G2, and blue color component B2 received from coated first surface 731R (731L) onto image capture sensor 715R (715L).

Each of image capture sensors 710R (710L) and 715R (715L) is a color sensor with a color filter array in this aspect. The color filter array is a Bayer red, green, green, blue (RGGB) color filter array. Thus, the two Bayer pattern image capture sensors are looking through the same optics at the same scene. Here, a Bayer pattern image capture sensor is a single chip sensor, or part of a single chip, that includes a Bayer color filter array. As noted above, coplanar image capture sensors 710R (710L) and 715R (715L) have a common front end optical structure and substantially the same optical path length to each sensor.

When prism assembly 730R (730L) and reflective unit 540R (540L) are arranged so that the color images captured by both Bayer pattern image capture sensors 710R (710L) and 715R (715L) are the same scene, the color image captured by image capture sensor 710R (710L) has the same full resolution as the color image captured by image capture sensor 715R (715L). Thus, each point in space in the scene is represented by two pixels with each of the two pixels having a different three color component vector. Sensor assembly 720R (720L) and consequently image capture unit 725R (725L) has acquired a full resolution image with six primary color components with no loss of light or spatial resolution.

The color component vector for each pixel output to stereoscopic display 251 from dual image enhancement module 240R (240L) in central controller 260 is derived from the six primary color components for this pixel. This permits driving a stereoscopic display with for example, a four element vector for each pixel without any loss in resolution. Dual image enhancement module 240R (240L) samples the two captured images and applies a color correction matrix to generate the pixel vector required by stereoscopic display 251.

The color component vector sent to stereoscopic display 251 can have more than three color components to more accurately represent the spectral content of the scene. In actual use, the number of color components used in the color component vector, sometimes referred to as a color vector, would match the number of color components used by the display. Sharp has shown five color component displays.

In another aspect, it is noted, for example, that when fluorescence is excited, the fluorescence may be in the visible spectrum. For example, Fluorescein may be excited by 490 nm blue light and fluoresces mainly in the 520 to 530 nm range. Thus, in this aspect, a color filter that blocks transmission of the reflected illumination from the excitation laser module, at say 490 nm, is included in coated first surface 731R (731L). The notch filter for the blue wavelengths is configured to reflect color component B1 and to pass other blue wavelengths so that the fluorescence from the Fluorescein is passed to image capture sensor 715R (715L). The notch filters and the illumination components from the illuminator for the red and green color components are selected so that the reflected color components R1, B1, and G1 are captured by first image capture sensor 710R (710L). The remaining colors are delivered to second image capture sensor 715R (715L). Note that the excitation laser component B1 may saturate the blue pixels of first image capture sensor 710R (710L), but this is acceptable as the fluorescence from the Fluorescein is captured by second image capture sensor 715R (715L)

In another aspect, a color correction module 241R (241L) in dual image enhancement module 240R (240L) of central controller 260 uses the three color pixels from the first image and the three color pixels from the second image to generate a five color component output vector for a Sharp five color display, e.g., generated a red, red complement, yellow, green, blue (RR'YGB) color component. The color correction matrix is set to the desired mapping from the six element acquisition color space to the display's five element color space.

More specifically, color correction module 241R (241L) in dual image enhancement module 240R (240L) of central controller 260 is coupled to the first and second image capture sensors 710R (710L) and 715R (715L). Camera control unit 230R (230L) demosaics the first image captured by the first image capture sensor 710R (710L), and demosaics the second image captured by the second image capture sensor 715R (715L). Each pixel in the demosaiced images has a three element color vector. The two demosaiced imaged are received by color correction module 241R (241L). The three element color vectors are combined from the two demosaiced images to create an N-element color component vector for each pixel, where N is at least three and in this example N is six. The color correction matrix in color correction module 241R (241L) then generates an M-element color component vector for a pixel in an output image from the N-element color component vector of the corresponding pixel. Note that when M is three, the processes described above that utilize the two captured images to enhance resolution, etc. can also be applied.

Enhanced Color Performance—White Broadband Illumination

In a second aspect, a white broadband illuminator 710C (FIG. 7C) is coupled to illumination channel 705 (FIG. 7A). In one example, illuminator 710C use a Xenon lamp 710C1 with an elliptic back reflector and a band pass filter coating to create broadband white illumination light with little infrared content. The use of a Xenon lamp is illustrative only and is not intended to be limiting. For example, a high pressure mercury arc lamp, other arc lamps, or other broadband light sources may be used.

Figure 7F:
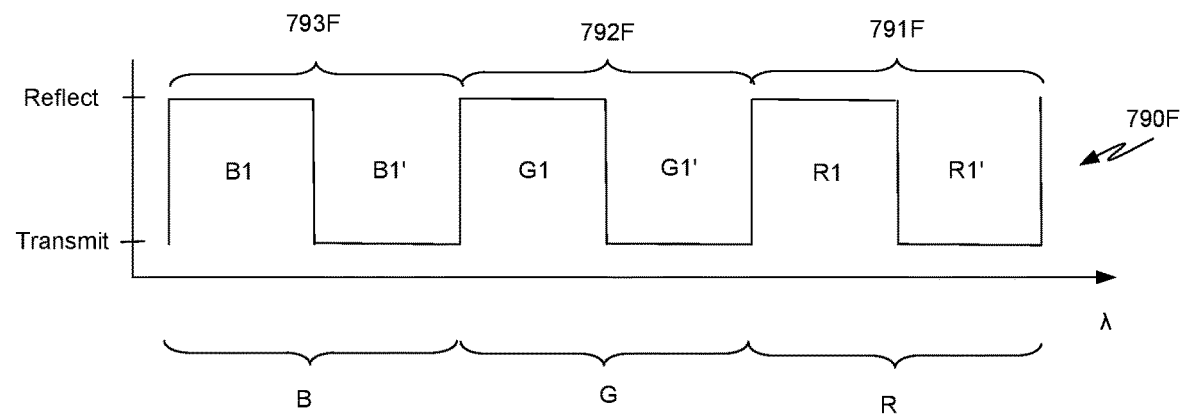
FIG. 7F is a graphical representation of a filter that includes a plurality of notch filters.

In this aspect, coated first surface of 731R (731L) of prism assembly 730R (730L) includes a filter 790F (FIG. 7F) that includes a plurality of notch filters. A first notch filter 791F reflects a first part R1 of a red color component R in the received light and transmits a complement R1' of first part R1 of red color component R in the received light. A second notch filter 792F reflects a first part G1 of a green color component G in the received light and transmits a complement G1' of first part G1 of green color component G in the received light. A third notch filter 793F reflects a first part B1 of a blue color component B in the received light and transmits a complement B1' of first part B1 of blue color component B in the received light. The use of three notch filters is for ease of discussion and is not intended to be limiting to three separate filters. The three separate notch filters can be viewed as a single multi-notch filter with the reflect, transmit properties described here.

Hence, coated first surface of 731R (731L) reflects red color component R1 in the received light, green color component G1 in the received light, and blue color component B1 in the received light onto second surface 732R (732L). Coated surface of 732R (732L) reflects all wavelengths received from coated first surface 731R (731L) onto image capture sensor 710R (710L).

Coated first surface of 731R (731L) transmits red color component R1' in the received light, green color component G1' in the received light, and blue color component B1' in the received light to third surface 541R (541L) in reflective unit 540R (540L). Coated surface of 541R (541L) reflects all wavelengths received from coated first surface 731R (731L) onto image capture sensor 715R (715L).

Each of image capture sensors 710R (710L) and 715R (715L) is a color sensor with a color filter array in this aspect. The color filter array is a Bayer RGGB color filter array. Thus, the two Bayer pattern image capture sensors are looking through the same optics at the same scene. Here, a Bayer pattern image capture sensor is a single chip sensor, or part of a single chip, that includes a Bayer color filter array. As noted above, coplanar image capture sensors 710R (710L) and 715R (715L) have a common front end optical structure and substantially the same optical path length to each sensor.

When prism assembly 730R (730L) and reflective unit 540R (540L) are arranged so that the color images captured by both Bayer pattern image capture sensors 710R (710L) and 715R (715L) are the same scene, the color image captured by image capture sensor 710R (710L) has the same full resolution as the color image captured by image capture sensor 715R (715L). Thus, each point in space in the scene is represented by two pixels with each of the two pixels having a different three color component vector. Thus, sensor assembly 720R (720L) has acquired a full resolution image with six primary color components-three from the first captured image and three from the second captured image-per pixel with no loss of light due to the notch filters.

The color component vector for each output pixel to stereoscopic display 251 from dual image enhancement module 240R (240L) in central controller 260 is derived from the six primary color components for this pixel. This permits driving a stereoscopic display with for example, a four element color vector for each pixel without any loss in resolution. Dual image enhancement module 240R (240L) samples the two images and applies a color correction matrix to generate the pixel vector required by stereoscopic display 251.

In this aspect, the coatings—the notch filter—on coated first surface 731R (731L) provide the flexibility to pick the color separation. The color separation of coated first surface 731R (731L) is, of course, multiplied by the pixel RGGB pattern. Thus, if coated first surface 731R (731L) is separating out yellow for example, it is expected that this would excite both green and red pixels and this would then be recovered in the color correction matrix process of the imaging pipeline. Similarly, the coated first surface can be configured to pass blue wavelengths in a fluorescence spectrum, and reflect all other wavelengths of blue, for example.

As described above, the color correction matrix acts upon a six element vector per pixel (a three color component vector of a corresponding pixel in a first image captured by image capture sensor 710R (710L) plus a three color component vector of a corresponding pixel from a second image captured by image capture sensor 715R (715L)) and produces an output color component vector with the number of color components in the display—for a "normal" LCD, this is the red, green blue (RGB) color components, and for a Sharp five color display, this is the red, red complement, yellow, green, blue (RR'YGB) color components.

More specifically, color correction module 241R (241L) in dual image enhancement module 240R (240L) of central controller 260 is coupled to the first and second image capture sensors 710R (710L) and 715R (715L). Camera control unit 230R (230L) demosaics the first image captured by the first image capture sensor 710R (710L) and generates an N-element color vector for each pixel-N typically is three. Camera control unit 230R (230L) similarly demosaics the second image captured by the second image capture sensor 715R (715L) into pixels, where each pixel is presented by a second N-element color vector. Dual image enhancement module 240R (240L) then processes the two N-element color vector as a 2N (typically six) color vector through color correction color correction module 241R (241L) to create an output color vector for each pixel with the desired number of color components. The output color vector for a typical liquid crystal display would have three color components. For a Sharp display with five primaries, the output color vector would be a five element color vector. A specific color correction matrix would be chosen based on optimization to achieve the best color performance by some metric. The metric could be, for example, to match the color seen by a human observer with Xenon illumination for some set of tissue types.

Enhanced Color Performance—White Broadband Illumination and Enhanced Depth of Field In a third aspect, illuminator 710C (FIG. 7C) is coupled to illumination channel 705 (FIG. 7A). Illuminator 710C is the same as that described above and so that description is not repeated here. Thus, the scene is illuminated by broadband white light from illuminator 710C.

As noted above, the reflected light from tissue 703 passes through lens element 704R (704L) and stop 570R (570L). In this aspect, lens element 704R (704L) is different from the lens element considered above for the other aspects related to FIG. 7A. In the other aspect, lens element 704R (704L) is designed to correct for longitudinal color aberrations so that the various color components focus on about the same plane. In this aspect, lens element 704R (704L) does not correct for longitudinal color aberrations. Instead, lens element 704R (704L) is designed to focus different wavelengths of light at different distances from the lens, i.e., is designed to have a significant and controlled amount of longitudinal color. For example, lens groups 482 and 484 in lens assembly 401B (FIG. 4B) are designed to have a significant and controlled amount of longitudinal color. Such lens groups are known to those knowledgeable in the field and so is not considered in further detail herein.

In this aspect, coated first surface of 731R (731L) of prism assembly 730R (730L) includes filter 790F (FIG. 7F) that was previously described. To avoid repetition, the above description of filter 790F is not repeated here.

Hence, coated first surface of 731R (731L) reflects red color component R1 in the received light, green color component G1 in the received light, and blue color component B1 in the received light to second surface 732R (732L). Coated surface of 732R (732L) reflects all wavelengths received from coated first surface 731R (731L) onto image capture sensor 710R (710L).

Coated first surface of 731R (731L) transmits red color component R1' in the received light, green color component G1' in the received light, and blue color component B1' in the received light to third surface 541R (541L) in reflective unit 540R (540L). Coated surface of 541R (541L) reflects all wavelengths received from coated first surface 731R (731L) onto image capture sensor 715R (715L).

Again, each of image capture sensors 710R (710L) and 715R (715L) is a color sensor with a color filter array in this aspect. The color filter array is a Bayer RGGB color filter array. Thus, the two Bayer pattern image capture sensors are looking through the same optics at the same scene. Here, a Bayer pattern image capture sensor is a single chip sensor, or part of a single chip, that includes a Bayer color filter array. As noted above, coplanar image capture sensors 710R (710L) and 715R (715L) have a common front end optical structure and substantially the same optical path length to each sensor.

When prism assembly 730R (730L) and reflective unit 540R (540L) are arranged so that the color images captured by both Bayer pattern image capture sensors 710R (710L) and 715R (715L) are the same scene, the color image captured by image capture sensor 710R (710L) has the same full resolution as the color image captured by image capture sensor 715R (715L). Thus, each point in space in the scene is represented by two pixels with each of the two pixels having a different three element vector. Thus, sensor assembly 720R (720L) has acquired a full resolution image with six primary color components-three from the first captured image and three from the second captured image—for each point in space with no loss of light due to the notch filters. However, due to the longitudinal color, the captured images are blurred different amounts in each of the six color primaries acquired.

Hence, in this aspect, dual image enhancement module 240R (240L) includes a digital filter kernel for each of the first and second images. The digital filter kernel processes the captured image based on the known longitudinal color aberrations to enhance the sharpness and focus of the image, i.e., to generate third and fourth images. The third and fourth images are demosaiced. The resulting demosaiced third image and fourth image can each be focused at a range of distances from the lens assembly and so as to provide an image having a greater depth of field than from a traditional lens design that brought all the color components into focus. Digital filter kernels are known to those knowledgeable in the field. This approach works well for surfaces with smooth reflectance curves in wavelength; this is the case for most tissue.

The vector for each output pixel to stereoscopic display 251 from dual image enhancement module 240R (240L) in central controller 260 is derived from the six primary color components for pixels in the demosaiced third and fourth images. Dual image enhancement module 240R (240L) samples the third and fourth images created by the digital filter kernel and applies a color correction matrix to generate the pixel vector required by stereoscopic display 251. The resulting combined image has a depth of field that is potentially three times greater than an image obtained from the conventional lens system.

Enhanced Color Performance—Three Color Component Illumination and Fluorescence

In a fourth aspect, an illuminator 710D (FIG. 7D) is coupled to illumination channel 705 (FIG. 7A). Illuminator 710D includes three laser illumination sources 710D1 to 710D3 that generate a red color component R1, a green color component G1, and a blue color component B1, respectively. Sometimes herein, three laser illumination sources 710D1 to 710D3 are referred to as three laser illumination modules. The configuration of an illuminator with multiple different illumination sources, a mirror for source 710D1 and dichroic mirrors for sources 710D2 and 710D3 is known. With laser illumination sources, the wavelengths of red color component R1, a green color component G1, and blue color component B1 are typically 2 to 5 nanometer (nm) wide instead of about 60 nm per color component from a conventional light emitting diode based illuminator.

Figure 7G:
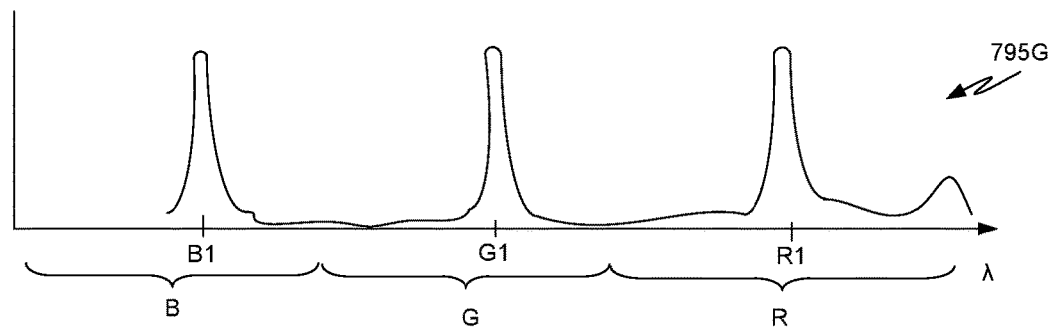
FIG. 7G is a graphical representation of a spectrum of light that is received by an image capture unit.

The light from the red, green and blue lasers reflects off tissue 703. The intensities of the reflected color component R1, color component G1, and color component B1 are modulated by the reflectance function of the tissue. In addition, to the three reflected color components from illuminator 710D, tissue 703 may emit other light. For example, the light from one of the lasers may excite fluorescence. See for example spectrum 795G (FIG. 7G). The three peaks are light reflected by tissue 703 from the red, green and blue lasers of illuminator 710D. The relatively smaller and broader peak in the red region of the spectrum is fluorescence. Spectrum 795G is presented to aid in visualization of the light that enters endoscope 702 and is not representative of any actual data.

Sensor assembly 720R (720L) enables capture of a color image by first image capture sensor 710R (710L) and enables all the light not associated with the color image to be redirected to second image capture sensor 715L (715R). Thus, as explained more completely below, sensor assembly 720R (720L) also enables imaging fluorescence in real time at nearly any wavelength in the visible or near infrared, and enables imaging natural tissue fluorescence.

Fluorescent markers may be stimulated by a narrow band source like a laser 710E4 in illuminator 710E that emits a wavelength in the near infrared spectrum. The fluorescent emission spectrum, however, is a range of wavelengths. The shape of the fluorescent emission spectrum is not significantly dependent on the excitation wavelength in a range of excitation wavelengths for the fluorescence.

Thus, in one aspect, fluorescence is triggered by light from a laser module 710E4 in illuminator 710E. As an example, antibody agents, which were obtained from Medarex, Inc., were excited using a 525 nm laser. In another aspect, illuminator 710D includes one or more light modules in addition to the three laser modules that generate red color component R1, green color component G1, and blue color component B1. The number and type of additional light modules are selected based on the fluorescence excitation wavelengths for one or more fluorescences of interest.

The particular fluorescence excitation source selected for combination light source 210 depends on the fluorophore or fluorophores used. Excitation and emission maxima of various FDA approved fluorescent dyes used in vivo are presented in Table 1.

TABLE 1

| Fluorescent Dye | Excitation maxima (nm) | Emission maxima (nm) |
|---|---|---|
| Fluorescein | 494 | 521 |
| Indocyanine Green | 810 | 830 |
| Indigo Carmine ® | 436 in alkaline solution | 528 in alkaline solution |
| Methylene Blue | 664 | 682 |

Indigo Carmine ® is a U.S. registered trademark of Akorn, Inc. of Lake Forrest, Ill. USA.

Table 2 presents examples of common protein fluorophores used in biological systems.

TABLE 2

| Fluorescent proteins/ Fluorophore | Excitation maxima (nm) | Emission maxima (nm) |
|---|---|---|
| GFP | 489 | 508 |
| YFP | 514 | 527 |
| DsRed (RFP) | 558 | 583 |
| FITC | 494** | 518** |
| Texas red | 595** | 615** |
| Cy5 | 650** | 670** |
| Alexa Fluor 568 | 578** | 603** |
| Alexa Fluor 647 | 650** | 668** |
| Hoechst 33258 | 346 | 460 |
| TOPRO-3 | 642 | 661 |

**Approximate excitation and fluorescence emission maxima for conjugates.

Those knowledgeable in the field understand that a fluorophore can be bound to an agent that in turn binds to a particular tissue of the patient. When a particular fluorophore is selected, if one of the three visible color component laser modules in illuminator 710D does not provide the necessary excitation wavelength, another laser module 710E4 can be added to illuminator 710D to obtain illuminator 710E that provides light with the excitation maxima wavelength for that fluorophore. Thus, given the fluorophore or fluorophores of interest and the number of different fluorophores used, appropriate light sources can be included in illuminator 710D to provide illumination of a color image of the scene and to excite fluorescence.

The above examples in Tables 1 and 2 are illustrative only and are not intended to limit this aspect to the particular examples presented. In view of this disclosure, an alternate imaging characteristic of the tissue can be selected and then an appropriate light source can be selected based upon the fluorescence being utilized.

Figure 7H:
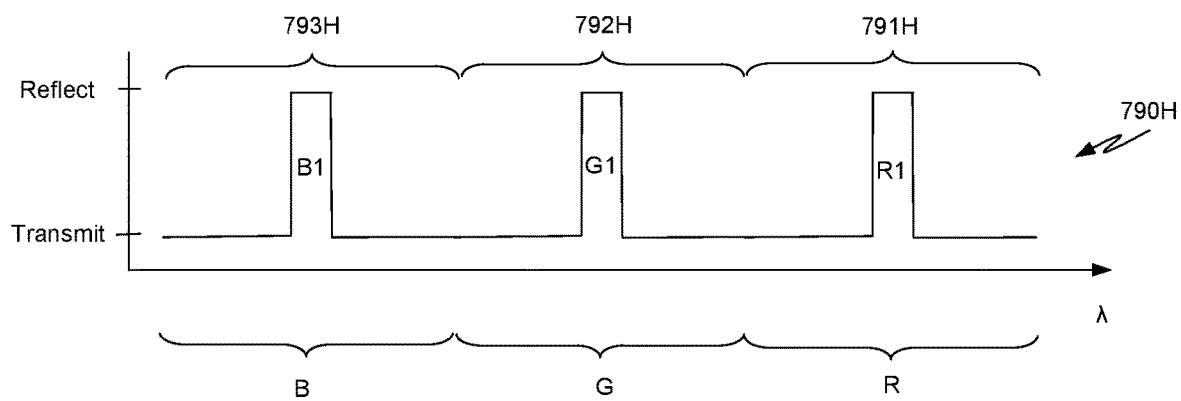
FIG. 7H is a graphical representation of another filter that includes a plurality of notch filters.

In this aspect, coated first surface of 731R (731L) of prism assembly 730R (730L), i.e., the beam splitter, includes a filter 790H (FIG. 7H) that includes a plurality of notch filters. A first notch filter 791H reflects red color component R1 in the received light and transmits other wavelengths of red color component R in the received light. A second notch filter 792H reflects green color component G1 in the received light and transmits other wavelengths of green color component G in the received light. A third notch filter 793H reflects blue color component B1 in the received light and transmits other wavelengths of blue color component B in the received light. The use of three notch filters is for ease of discussion and is not intended to be limiting to three separate filters. The three separate notch filters can be viewed as a single multi-notch filter with the reflect, transmit properties described here.

Hence, coated first surface of 731R (731L) reflects red color component R1 in the received light, green color component G1 in the received light, and blue color component B1 in the received light to second surface 732R (732L). Second surface of 732R (732L) reflects all wavelengths received from coated surface 731R (731L) onto image capture sensor 710R (710L).

Coated first surface of 731R (731L) transmits red light other than red color component R1 in the received light, green light other than green color component G1 in the received light, and blue light other than blue color component B1 in the received light to third surface 541R (541L) in reflective unit 540R (540L). Third surface of 541R (541L) reflects all wavelengths received from coated surface 731R (731L) onto image capture sensor 715R (715L).

Thus, image capture sensor 710R (710L) acquires an RGB image of the laser illuminated scene. This is a color image. All the remaining light is reflected onto image capture sensor 715R (715L). This light must be from a source other than the illumination. For example, if there is natural tissue fluorescence, the fluorescence is captured by image capture sensor 715R (715L). If image capture sensor 715R (715L) is a color image capture sensor, the fluorescence can be of any color and the fluorescence is imaged in color on image capture sensor 715R (715L). There may be slight losses in the fluorescence due to the notch filters on coated first surface of 731R (731L). In this aspect, image capture sensor 710R (710L) is a color sensor with a color filter array. The color filter array is a Bayer RGGB color filter array.

The type of image capture sensor selected for image capture sensor 715R (715L) depends on the characteristics of the other light that is captured by image capture sensor 715R (715L). The gain and other parameters of image capture sensor 715R (715L) may be independent of image capture sensor 710R (710L) so that image capture sensor 715R (715L) acquires the best image possible.

If a single fluorescent spectrum is of interest, or if distinguishing between different fluorescent spectra is not of interest, image capture sensor 715R (715L) can be a monochrome sensor. Alternatively, if more than one color fluorescent spectrum is of interest, e.g., a fluorescent spectrum in the red wavelengths and a fluorescent spectrum in the green wavelengths, image capture sensor 715R (715L) can be a color image capture sensor with a Bayer color filter array.

With a monochrome image capture sensor, there is a benefit in terms of resolution and light gathering. The color image capture sensor gives more information about the wavelength or wavelengths of the light received.

Irrespective of the implementation of image capture sensor 715R (715L), the two image capture sensors are looking through the same optics at the same scene. As noted above, coplanar image capture sensors 710R (710L) and 715R (715L) have a common front end optical structure and substantially the same optical path length to each sensor.

Any small amount of light, which goes to image capture sensor 710R (710L) and is not reflected laser illumination, is small relative to the reflected laser illumination. Assuming broad spectral responses and good registration of the images captured by image capture sensors 710R (710L) and 715R (715L), dual image enhancement module 240R (240L) could correct the image captured by image capture sensors 710R (710L) using the image captured by image capture sensor 715R (715L).

If fluorescence is excited by an excitation wavelength from an illumination module different from the illumination modules in illuminator 710D that generate light having wavelengths R1, G1, B1, an excitation blocking notch filter is required in the image capture unit imaging path, e.g., between stop 570R (570L) and sensor assembly 720L (720R). Irrespective of the excitation wavelength of the fluorescence, the fluorescent light can be in the visible spectrum and be imaged onto image capture sensor 715R (715L). Multiple fluorophores could be imaged simultaneously if desired and the emission spectra excite different colors on image capture sensor 715R (715L).

The configuration of dual enhancement module 240R (240L) depends on the whether second image capture sensor 715R (715L) is a color image capture sensor or a monochrome image capture sensor. If both image capture sensors are color sensor, CCU 230R (230L) demosaics the two captured images and controller 260 generates an N-element color component vector for each pixel in the output image as described above. Three of the color components in the N-element color component vector represent a color image and the remaining color components represents fluorescence. If the second image capture sensor is monochrome, the demosaicing of the second captured image is unnecessary.

Thus, irrespective of the implementation of second image capture sensor 715R (715L), controller 260 is configured to generate at least a four element color component vector for a pixel in an output image from a color component vector for a corresponding pixel in the first image and a color component vector for a corresponding pixel in the second image. Three of the elements in the four element color component vector are for a visible color image, and a fourth element in the four element color component vector is for a fluorescent image.

In the aspect of FIG. 7A and each of the examples described above with respect to FIG. 7A, the image capture sensors in a stereoscopic channel are coplanar. This is illustrative only and is not intended to be limiting. For example, a first of the image capture sensors could have a top sensor surface in a first plane, and a second of the image capture sensors could have a top sensor surface in a second plane. The first and second planes are parallel to each other and are separated by a known distance (See FIG. 9). The spacing between the beam splitter and the reflective surface in the reflective unit is adjusted to compensate for the known distance so that the first optical path length to the first image capture sensor is about equal to the second optical path length to the second image capture sensor. Thus, each of the aspects of FIG. 7A described above are directly applicable to this configuration as the two optical path lengths remain about equal.

Extended Depth of Field

In a surgical endoscope, one would like to provide as sharp and as bright an image as possible to the surgeon. This requires a lens design with the largest possible aperture. A larger aperture forms a sharper image (within the limitations of the sensor) and allows more light through leading to a brighter image (better signal to noise ratio). However, there is a trade-off in that a larger aperture leads to a shallower depth of field. The surgeon would prefer an image with a greater depth of field to avoid having to control the focus of the imaging system as the surgeon looks at things at different distances away from the camera. Thus, the surgeon would like an image with the sharpness and brightness of a large aperture and much improved depth of field. To achieve this goal, each of image capture units 825L and 825R (FIG. 8A) capture images of tissue 803 with different focus. Dual image enhancement modules 240R, 240L (FIG. 2) process the captured images and provide the surgeon with depth of field capabilities not previously available.

For example, in one aspect, a first image 881 (FIG. 8B) captured by sensor assembly 820R (820L) has a first focus. A second image 882 (FIG. 8C) captured by sensor assembly 820R (820L) has a second focus. In image 881, the features in the center of the image are in focus as represented by the dark distinct lines. The features in the left and right sides of image 881 are further from image capture unit 825R (825L) and are out of focus as represented by the cross-hatching. In image 882, the features in the center of the image are out of focus as represented by the cross-hatching. The features in the left and right sides of image 882 are in focus as represented by the dark distinct lines.

Figure 8A:
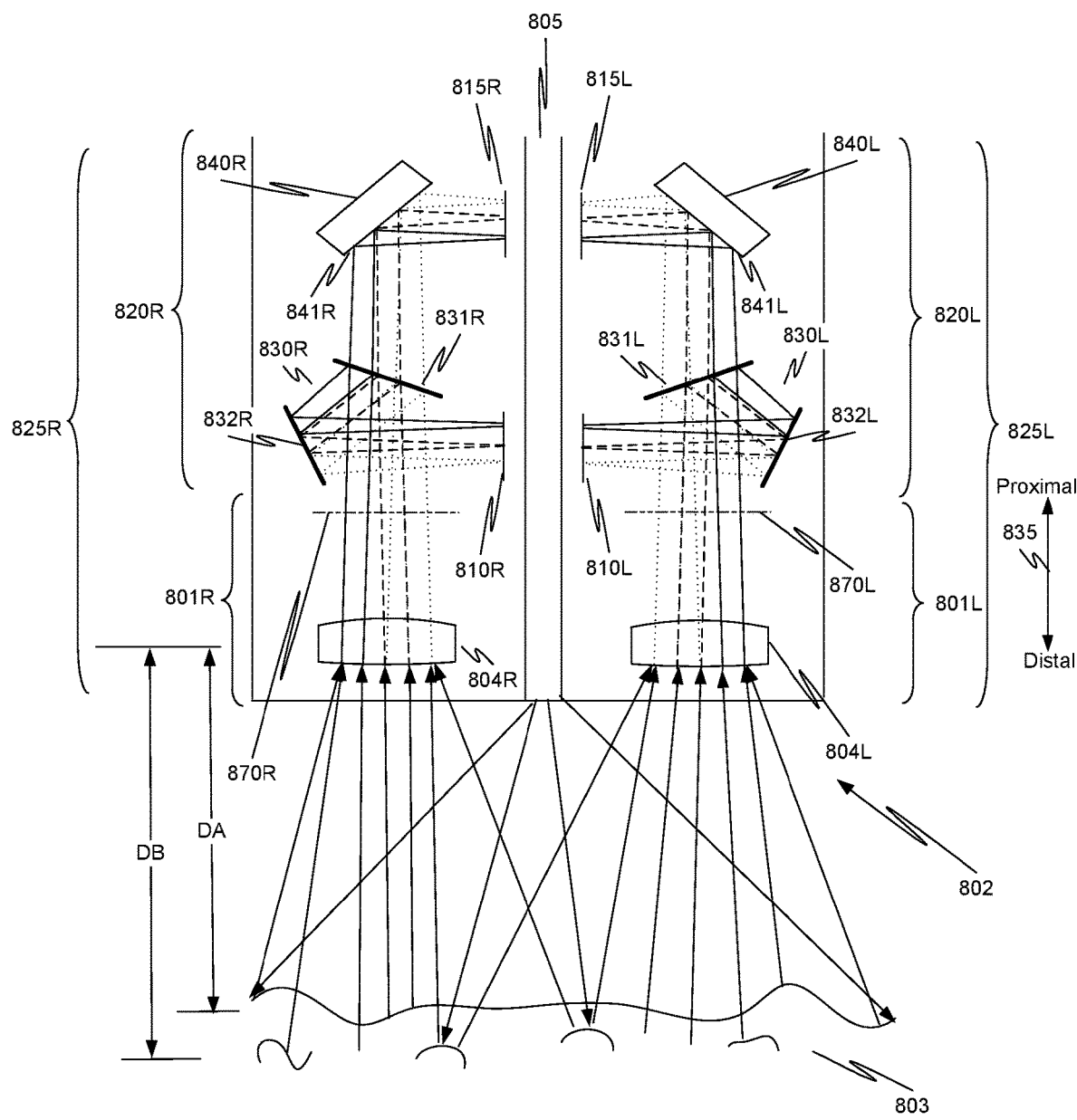
FIG. 8A is a schematic illustration of a distal end of a stereoscopic endoscope including an illumination channel that provides light from an illuminator, and left and right stereoscopic optical channels that each includes an image capture unit having a lens assembly and a sensor assembly. Each sensor assembly has two different optical path lengths.
Figure 8B:
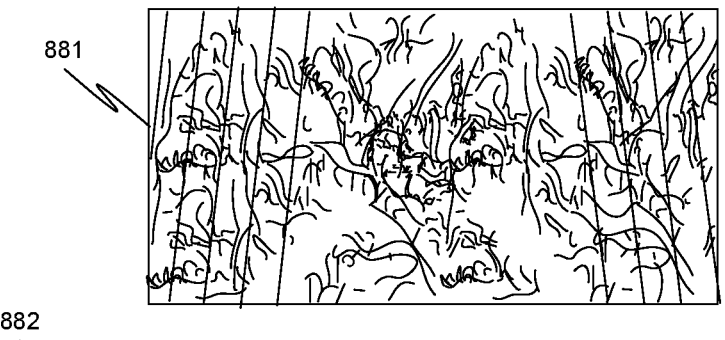
FIGS. 8B and 8C are illustrations of two images captured in a sensor assembly with different depths of field and different focus.
Figure 8C:
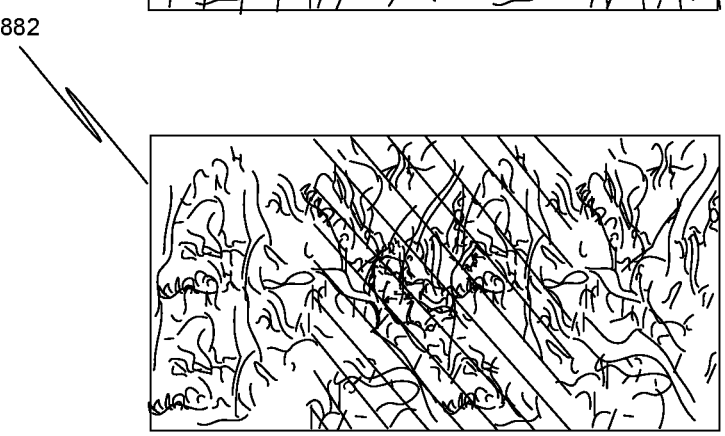
Figure 8D:
FIG. 8D is an illustration of one combination of the two images of FIGS. 8B and 8C combined to form an in focus image with extended depth of field.

As explained more completely below, the in focus portions of images 881 and 882 are used to generate a composite in focus image that is sent to stereoscopic display 251 (FIG. 8D). This provides an image containing better depth of field than is available in either of images 881 and 882. Another benefit of this approach is that information from images 881 and 882 along with a sharpness metric are used to generate an image from a perspective of virtual cameras that are sent to stereoscopic display 251 for display. This allows the surgeon to view tissue 803 from slightly different perspectives without physically moving endoscope 802.

FIG. 8A is a schematic illustration of a distal end of a stereoscopic endoscope 802 with image capture units 825L, 825R and an illumination channel 805 that provides light from an illuminator. As indicated by arrow 835, the distal direction is towards tissue 803 and the proximal direction is away from tissue 803.

Each image capture unit 825R, 825L includes a lens assembly 801R, 801L and a sensor assembly 820R, 820L. Sensor assembly 820R, 820L is positioned to receive light that passes through lens assembly 801R, 801L. Each sensor assembly 820R, 820L includes a prism assembly 830R, 830L, a reflective unit 840R, 840L, and coplanar image capture sensors (810R, 815R), (810L, 815L), in one aspect. However, the configuration illustrated in FIG. 9 could also be used in the aspects described using the configuration of FIG. 8A. Stereoscopic endoscope 802 is sometimes referred to as endoscope 802.

In the following description, the optical paths in the right channel of stereoscopic endoscope 802 are described. The optical paths through the left channel of stereoscopic endoscope 802 are equivalent those in the right channel due to the symmetry of endoscope 802, and so in the following description, the left channel reference numeral is included within parentheses following the description of an element in the right channel. This indicates that the description is also applicable to the corresponding element in the left channel. Also, the imaging processing that is described is performed in real time so that a continuous video sequence is provided to the display.

The light from tissue 803 passes through lens element 804R (804L) and stop 870R (870L) in lens assembly 801R (801L). The elements in lens assembly 401B (FIG. 4B) are an example of lens element 804R (804L). The light that passes through lens assembly 801R (801L) is received by image capture unit 825L (825R) and enters prism assembly 830R. Prism assembly 830R (830L) includes a beam splitter 831R (831L) that reflects a first percentage of the received light. Beam splitter 831R (831L) passes a second percentage of the received light through beam splitter 831R (831L) to reflective unit 840R (840L).

In one aspect, beam splitter 831R (831L) is implemented as a coated first surface 831R (831L). The light reflected by coated first surface 831R (831L) is received by a second surface 832R (832L) that in turn directs, e.g., reflects, the light onto first image capture sensor 810R (810L). Surface 832R (832L) can be either a coated surface or a total internal reflection surface. The light transmitted through coated first surface 831R (831L) is received by a third surface 541R (541L) of reflective unit 540R (540L) that in turn directs, e.g., reflects, the light onto second image capture sensor 815R (815L).

Second surface 832R (832L) is positioned so that no light other than the light reflected by coated first surface 831R (831L) hits second surface 832R (832L). In one aspect, the angle of incidence of the light to coated surface 831R (831L) is less than forty-five degrees.

In one aspect, prism assembly 830R (830L) and reflective unit 840R (840L) are included in a prismatic structure with a pentaprism that includes prism assembly 830R (830L). The prismatic structure in this aspect is equivalent to prismatic structure 460 (FIG. 4B) with buried coated surface 431B that splits the received light into the first and second percentages. Thus, the description of prismatic structure 460 is applicable to the prismatic structure used in this aspect.

In one aspect, the first and second percentages are about equal. In another aspect, the first and second percentages are different. Thus, prism assembly 830R (830L) includes a beam splitter 831R (831L) that separates the received light into the two portions-(i) a first percentage of the received light sometimes referred to as a first portion, and (ii) a second percentage of the received light, sometimes referred to as a second portion.

Image capture sensors 810R (810L) and 815R (815L) are coplanar. In one aspect, a first optical path length from stop 870R (870L) to coated first surface 831R (831L) to second surface 832R (832L) to image capture sensor 810R (810L) is a first length. A second optical path length from stop 870R (870L) through coated first surface 831R (831L) to a third surface 841R (841L) in assembly 840R (840L) to image capture sensor 815R (815L) is a second length. The first and second lengths are different, i.e., are not about equal. Again, the definition of the optical path lengths as starting at stop 870R (870L) is illustrative and is not intended to be limiting. The unequal optical path lengths could also be variously defined, such as with respect to a distal face of prism assembly 830R (830L) through which the received light enters prism assembly 830R (830L), with respect to a first element in lens assembly 801R (801L), or with respect to coated first surface 831R (831L). In another aspect, the different optical path lengths can be achieved with glass plates on the two image sensor areas with different indexes of refraction or other similar means.

Thus, coplanar image capture sensors 810R (810L) and 815R (815L) have a common optical path length through the front end optical structure in lens assembly 801R (801L) and different optical path lengths to each sensor in sensor assembly 820R (820L). First image capture sensor 810R (810L) captures an image from the first portion of the light received by sensor assembly 820R (820L). Second image capture sensor 815R (815L) captures an image from the second portion of the light received by sensor assembly 820R (820L).

In one aspect, each of image capture sensors 810R (810L) and 815R (815L) is a color sensor with a color filter array. In another aspect, the color filter array is removed from one of the color sensors and the sensor functions as a monochrome sensor. When a monochrome sensor is used, the sharpness from the image captured by the monochrome sensor is transferred to the color image if the focus of the two images is not too different, e.g., the two images are focused in the vicinity of the point where sharpness curves 885, 886 of the two images intersect (See FIG. 8E).

In one aspect, coated first surface 831R (831L) of prism assembly 830R (830L) is configured to reflect and to transmit about equal portions of the light received by prism assembly 830R (830L), i.e., the first and second percentages are about equal. Thus, beam splitter 831R, in this aspect, is the balanced beam splitter described above. In this example, each of image capture sensors 810R (810L) and 815R (815L) is a color sensor with a color filter array. The color filter array is a Bayer color filter array. Thus, the two Bayer pattern image capture sensors 810R (810L) and 815R (815L) are looking through the same optics at the same scene. Here, a Bayer pattern image capture sensor is a single chip sensor, or part of a single chip, that includes a Bayer color filter array. As noted above, coplanar image capture sensors 810R (810L) and 815R (815L) have a common front end optical structure, but different optical path lengths to each sensor.

The light going to image capture sensor 810R (810L) is captured as a first image focused at a first object distance DA from image capture unit 825R (825L). See for example FIG. 8B. The light going to image capture sensor 815R (815L) takes a slightly longer path to arrives sensor at 815R (815L) and is captured as a second image focused at a second object distance DB from the image capture unit. See for example, FIG. 8C. Distance DB is larger than distance DA. The difference in the path lengths is based on the front end optical design, e.g., focal length of lens element 804R (804L), and the distance for the best focus of each of the two captured images.

The first and second images are aligned and taken through the same lens element 804R (804L). The focal plane of the two images is different. The depth of field of the two images is also different. The image focused at distance DA, e.g., image 881, has a short depth of field whereas the image focused at distance DB, e.g., image 882, has a broader depth of field.

As noted above, the surgeon can use user interface 262 to cause dual image enhancement module 240R (240L) to generate, from the two captured images (FIGS. 8B and 8C), an in focus image (FIG. 8D) with an enhanced field of view Alternatively, the surgeon can show the two images on two planes of a display so the accommodation in surgeons control console display 251, sometimes called stereoscopic display 251, matches the surgical accommodation at the surgical site. Finally, the surgeon can switch between the first image with one focus and the second image with a second focus.

In one aspect, dual image enhancement module 240R (240L) generates an in focus extended depth of field image from the two images captured by image capture sensors 810R (810L) and 815R (815L). In a first aspect, a first sharpness metric is generated for a group of pixels, i.e., a tile, in the first image and a second sharpness metric is generated for a corresponding group of pixels in the second image. The two sharpness metrics are compared to determine which sharpness metric is larger. The group of pixels (or a selected pixel or pixels within the tile) with the largest sharpness metric is selected for the blended image. Dual image enhancement module 240R (240L) steps through the two captured images group by group and selects one of the two groups for inclusion in the blended image that is in focus over a greater field of view than the two captured images.

Figure 8E:
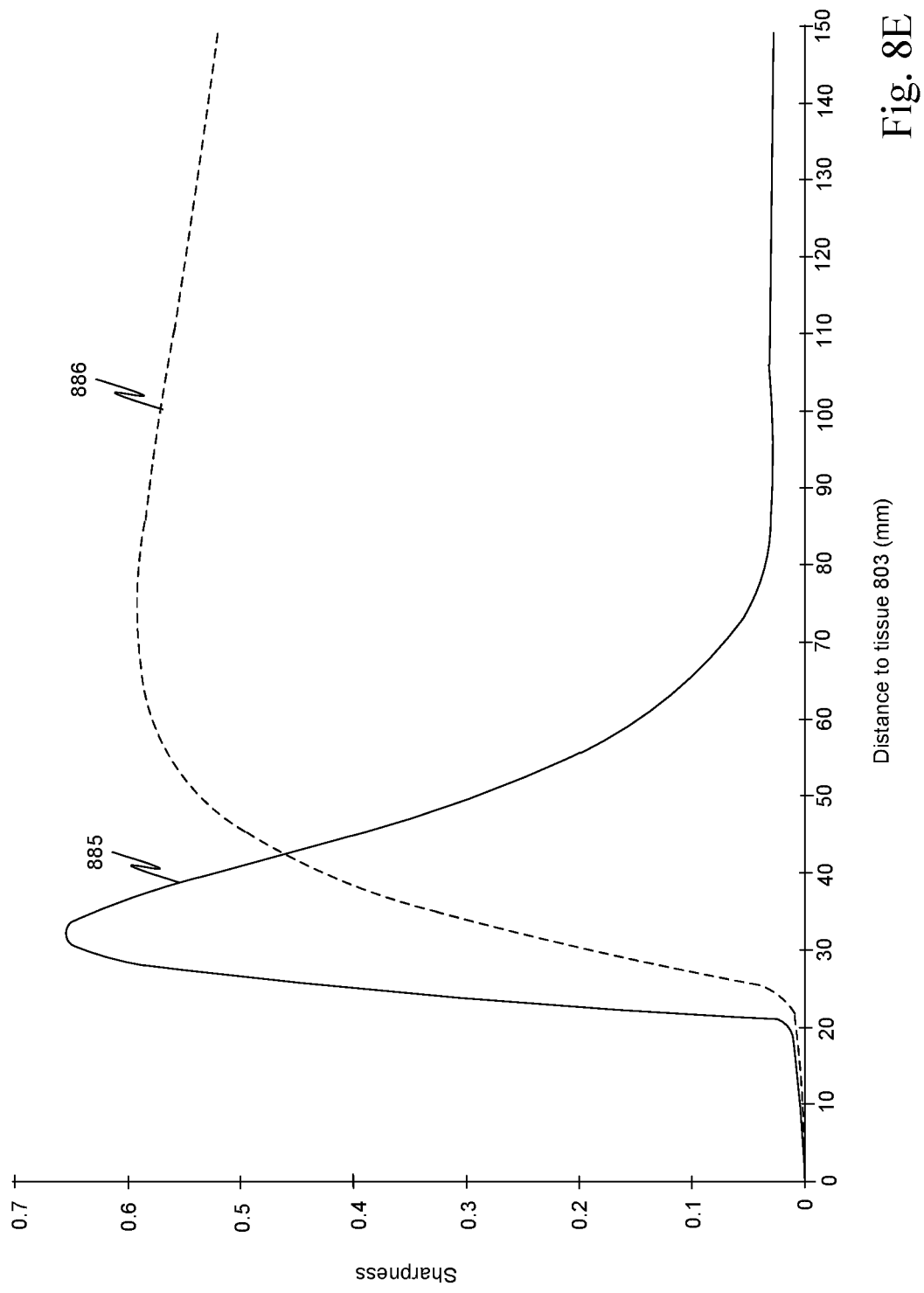
FIG. 8E shows the sharpness of the images acquired by the first and second image capture sensors versus object distance.

FIG. 8E is an illustration of a sharpness profile 885 for imaged captured by image capture sensor 810R (810L) and a sharpness profile 886 for the images captured by image capture sensor 815R (815L). The sharpness profile is a curve of the sharpness of an image captured by an image capture sensor versus the distance from the distal end of the endoscope. In one aspect, sharpness profiles 885 and 886 are empirically generated based on a calibration performed using endoscope 802 and a plurality of images taken of known objects at different distances from the distal end of endoscope 802.

In one aspect, profiles 885 and 886 are stored as look-up tables in a memory. The stored sharpness profiles are used by dual image enhancement module 240R (240L) to determine whether to display a first image captured by image capture sensor 810R (810L) or to display a second image captured by image capture sensor 815R (815L) as endoscope 802 is moved without moving the optics in image capture unit 825R (825L). Dual image enhancement module 240R (240L) generates a sharpness metric, using a conventional technique know to those knowledgeable in the field, for each of the first and second images. Dual image enhancement module 240R (240L) uses sharpness profiles 885 and 886 and the sharpness metrics to determine a distance between the distal end of endoscope 802 and the tissue for each of the images.

For example, if the first image has a sharpness metric of 0.5, distance DA to tissue 803 is either about forty-two millimeters (mm) or about twenty seven millimeters (mm) based on sharpness profile 885. If second image has a sharpness metric of about 0.43, distance DB to tissue 803 is about forty-two millimeters (mm) based on sharpness profile 886. Alternatively if second image has a sharpness metric of about 0.08, then the tissue distance is about twenty seven millimeters (mm). Note that sharpness profile 885 is ambiguous as to tissue depth based on the sharpness metric; the tissue depth is disambiguated by second curve 886. As both images are obtained at substantially the same time, this disambiguation is not skewed by temporal effects. Dual image enhancement module 240R (240L) uses the relative sharpness metric between the two images and the a-priori calibration of the curves to determine which of the two images to display as endoscope 802 is moved and the distance from the image capture unit to the tissue varies. The position of the distal end of the endoscope is known by central controller 260.

If endoscope 802 is moved closer to tissue 803, the first captured is image is sent to display 251 by dual image enhancement module 240R (240L). If endoscope 802 is moved away from tissue 803, dual image enhancement module 240R (240L) compares the distance from tissue 803 of the distal end of endoscope 802 with the distance at which sharpness profiles 885 and 886 intersect, referred to as the profile intersection distance. If the distance from tissue 803 of the distal end of endoscope 802 is smaller than the profile intersection distance, the first captured image is transmitted to display 251. If the distance from tissue 803 of the distal end of endoscope 802 is larger than the profile intersection distance, the second captured image is transmitted to display 251. Thus, for the sharpness metrics in the previous paragraph, when the distal end of end of endoscope 802 is less than 45 mm from tissue 803, the first image would be presented to the surgeon. When the distal end of end of endoscope 802 is more than 45 mm from tissue 803, the second image would be presented to the surgeon. Thus, as endoscope 802 is moved, the surgeon is presented with an appropriate image without having to move the optics in image capture unit 825R (825L).

Additionally, the determination of which of the two images to present to the surgeon may be determined solely on the basis of the relative sharpness metric; the calculation of tissue depth is not necessary. The image pair presented in the left and right eyes of the stereo viewer would be kept consistent and the sharpness metric comparison may use the data from the pair of images captured for the left eye and the pair of images captured for the right eye during the determination to use the first or second image. In general, if switching focus of the entire image presented, the first image would be chosen for both the right and left eyes or the second image would be chosen for the right and left eyes.

In another aspect, the captured two images and sharpness profiles 885, 886 are used to create a depth map. Sharpness profiles 885 is divided into sharpness profile 886 to generate a channel sharpness profile of a sharpness metric versus distance e.g., the value of profile 886 at a given distance is divided by the value of profile 885 at that given distance to obtain the sharpness metric for the given distance. This sharpness metric may be calculated through the use of sliding tiles to create a depth map for the entire image. Naturally, this information may be combined with more traditional stereo matching algorithms to generate a more well conditioned depth map.

Figure 8F:
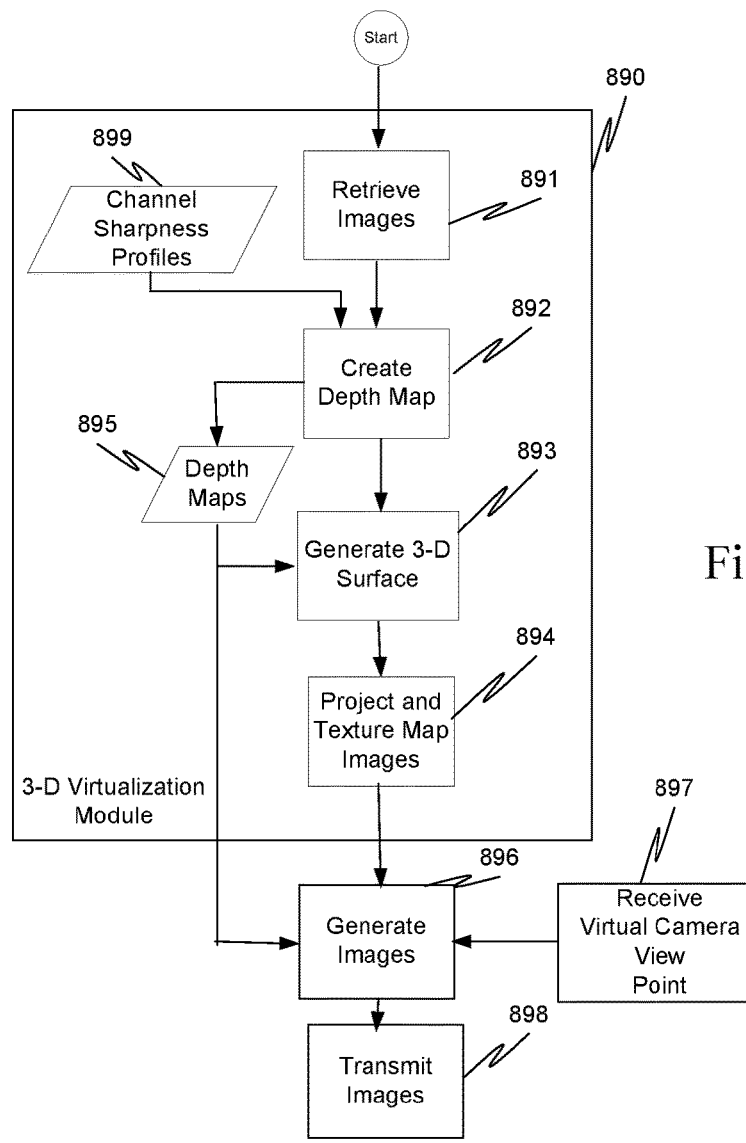
FIG. 8F is a process flow diagram of a method to generate a virtual image at a virtual camera view point from images captured by an image capture unit.

In one aspect, sharpness profiles 885 and 886 are empirically generated based on a calibration performed using endoscope 802 and a plurality of images taken of known objects at different distances from the distal end of endoscope 802. Sharpness profiles are obtained for both image capture unit 825R and for image capture unit 825L. A channel sharpness profile is generated for each of the left and right channels. In one aspect, the left and right channel sharpness profiles are saved as a look-up table in a memory 899 (FIG. 8F).

Recall that there is essentially a one to one correspondence between the pixels in the first captured image and the pixels in the second captured image. Establishing the one to one correspondence, in some instances, may require calibration and slight image warping or software based registration between the images. Dual image enhancement module 240R (240L) generates a sharpness metric, using a conventional technique know to those knowledgeable in the field, for tiles or groups around corresponding pixels in each of the first and second images. The sharpness metric for the pixel, or a group of pixels about the pixel, in the first captured image is divided into the sharpness metric for the corresponding pixel, or corresponding group of pixels about the corresponding pixel, in the second capture image to generate a channel sharpness metric for the pixels. The channel sharpness metric for the pixels is used to locate a point on the channel sharpness profile. The distance corresponding to that point on the channel sharpness profile is the depth associated with the (X,Y) position of the pixel. Performing this process for each pixel in the captured images generates a depth map for the captured images.

In one aspect, the depth map is used to generate view of a scene of tissue 803 from a perspective different from the perspective of endoscope 802, i.e., from a perspective of a virtual camera view point. Central controller 260 uses a three-dimensional virtualization module 890 (FIG. 8F) to generate a stereoscopic image pair for the virtual camera view points.

Three-dimensional virtualization module 890 uses the first and second images captured in the right stereoscopic channel of endoscope 802, and generates a first channel depth map for the scene viewed by the right channel. Similarly, three-dimensional virtualization module 890 uses the first and second images captured in the left stereoscopic channel of endoscope 802, and generates a second channel depth map for the scene viewed by the left channel. Additional information from stereo matching in the images may also be used to improve the stability and accuracy of the combined depth map. A three-dimensional surface of the scene is generated using the first and second channel depth maps and the best focused portions of the four captured images are projected on and textured onto the three-dimensional surface to create a textured three-dimensional image surface.

When a surgeon inputs a view point using user interface 262, i.e., a virtual camera view point, dual image enhancement module 240R uses the channel depth map for the right channel and the textured three-dimensional image surface to generate an image for the right channel from the virtual camera view point. Similarly, dual image enhancement module 240L uses the channel depth map for the left channel and the textured three-dimensional image surface to generate an image for the left channel from the virtual camera view point. The two images are sent to stereoscopic display 251 and the surgeon is presented a virtual three-dimensional image without moving endoscope 802 to the virtual camera view point.

More specifically, a 3-D virtualization module 895 is executed for each channel. This can be done either in parallel or sequentially depending on the memory and processing power available in central controller 260.

In RETRIEVE IMAGES process 891 for the right channel, first and second images captured in image capture sensors 810R and 815R are retrieved and provided to CREATE DEPTH MAP process 892, sometimes called process 892. Process 892 performs the same process repetitively for groups of pixels, e.g., tiles, in the two images.

In process 892 for a pixel (X,Y), a group of pixels including pixel (X,Y) are selected from each of the first and second images in the right channel. Here, X is the x-coordinate of the pixel and Y is the y-coordinate of the pixel. For example, the group of pixels could be a five pixel by five pixel block, with pixel (X,Y) at the center of the block. A first sharpness metric for the block of pixels from the first image is generated and a second sharpness metric for the same block of pixels from the second image is generated. The second sharpness metric is divided by the first sharpness metric to generate a channel sharpness metric. A distance Z corresponding to the channel sharpness metric is obtained using right channel sharpness profile in memory 899. Distance Z is assigned to pixel (X,Y). Thus, in the right channel depth map the pixel is represented as pixel (X, Y, $Z_{xy}$).

Next this process is repeated for pixel (X+1, Y), and the pixel in the depth map is pixel (X+1, Y, $Z_{(x+1)y}$). Thus, some of the pixels used in determining the common block sharpness metric for pixel (X,Y) are also used in determining the common block sharpness metric for pixel (X+1, Y). The process is repeated for each pixel in a row of pixels and then the Y index is incremented and the process repeated for each pixel in the next row pixels. For pixels in a boundary region of the scene that are not surrounded by a complete block of pixels, symmetry is assumed and the values for pixels available in the block are used to generate values for the missing pixels in one aspect.

When all the rows of pixels are processed, a right channel depth map has been created with each pixel in the scene viewed by the right channel. Each pixel has a value in the x-dimension, a value in the y-dimension, and a depth in the z-dimension. The right channel depth map is stored in a memory 895, in one aspect.

The depths in the right channel depth map are averages values that are a function of the size of the group of pixels. A large group of pixels reduces noise, but as the group becomes larger detail in the z-dimension is lost due to the averaging over the group. Thus, a size for the group is empirically determined to reduce the noise to an acceptable level while maintaining the desired specificity in the depth values. Also, the placement of the pixel for which the depth is being generated at the center of block is illustrative only and is not intended to be limiting to this specific placement.

This same process is performed for the left channel by create depth map process 892. When the processing for both the right and left channels is completed, memory 895 includes a right channel depth map and a left channel depth map. The left and right channel depth maps provide a depth mapping of the scene for the view point of endoscope 802.

GENERATE 3-D SURFACE process 893 in central controller 260 uses the left and right channel depth maps to generate a three dimensional surface of the scene. The use of two depths maps to generate a three dimensional depth map surface is known to those knowledgeable in the field and so is not considered further herein.

After generating, the three dimensional surface of the scene, PROJECT AND TEXTURE MAP IMAGES process 894 projects and texture maps the sharpest portions of the two acquired images in the right channel and the sharpest portions of the two acquired images in the left channel back on the three dimensional depth map surface to generate a textured three-dimensional image surface, sometimes referred to as a textured image surface. Projecting and texturing using a plurality of captured images and a three dimensional surface to generate a textured image surface is known to those knowledgeable in the field and so is not considered further herein.

With the textured image surface and the two channel depth maps, images for a stereoscopic image pair from a virtual camera view point can be generated. In this aspect, user interface 262 permits a surgeon to specify a virtual camera view point from which the surgeon wishes to view the current scene, e.g., a different perspective from which the surgeon wishes to view the current scene.

Hence, RECEIVE VIRTUAL CAMERA VIEW POINT process 897 receives the virtual camera view point from user interface 262 and provides the virtual camera view point to GENERATE IMAGES process 896. GENERATE IMAGES process 896 uses the right channel depth map from DEPTH MAPS 895, the textured image surface, and the virtual camera view point to generate a virtual right channel image from the virtual camera view point. Similarly, GENERATE IMAGES process 896 uses the left channel depth map from DEPTH MAPS 895, the textured image surface, and the virtual camera view point to generate a virtual left channel image from the virtual camera view point. Generating a virtual image using a depth map and a textured image surface for a virtual camera view point is know to those knowledgeable in the field and so is not considered in further detail.

Upon generation of the left and right channel virtual images for the virtual camera view point, TRANSMIT IMAGES process 898 sends the two virtual images to stereoscopic display 251 for display to the surgeon. Thus, without moving endoscope 802, the surgeon is able to view the scene from a different view point, i.e., a virtual camera view point. Naturally, viewing the scene from a view point wildly different than that of endoscope 802 does not necessarily lead to a high quality image. However, images for virtual camera points near the endoscope tip are of reasonable quality.

This approach may also be used for generating the images for other participants in an operating room. For example, the operating room staff near the patient likely views the surgical procedure on a non-stereo display unit, such as on a television screen or a monitor. The ability to create images from virtual camera positions can enable the presentation of the scene in such a way as to give the operating room staff a sense of depth on that display.

This may be done by presenting, in real time, a sequence of images from virtual camera positions which sweep from the actual surgeon right eye position to the actual surgeon left eye position and back, i.e., the virtual camera positions are swept over the interocular separation between the two eye positions. The sweeping of the virtual camera view point back and forth generates a sequence of images of a scene from a plurality of virtual camera view points. Specifically, at each time step, an image from a different virtual camera view point is generated and presented.

The actual right eye position and the actual left eye position, for example, refer to the left eye position and the right eye position of a stereoscopic viewer that is a part of the surgeons control console, in one aspect. The left eye position and right eye position are separated by the interocular separation.

The display of the images generated by this sweeping of the virtual camera position over time gives the appearance on the display of small back and forth head motions, i.e., the displayed images provide a slight rocking back and forth of the scene. This is one of the many depth cues used by the human visual system and provides a sense of the scene depth to the operating room staff without requiring the use of a stereoscopic display. Additionally, this has the advantage that the image communicates depth independent of the orientation of the operating room staff to the display and does not require any special additional equipment. The virtual camera images may also be created by considering the images captured as samples of a light field and using image based rendering techniques to create the new virtual camera views.

In the aspect just described, the stereoscopic image for the virtual camera view point was generated using images from stereoscopic endoscope 802. In another aspect, a stereoscopic image for the virtual camera view point is generated using a pair of images from a monoscopic endoscope, e.g., an endoscope that has only the right channel of stereoscopic endoscope 802.

In this aspect, 3-D virtualization module 890 performs process 891 to 894 for the two captured images to generate a first image for the three-dimensional image. To generate the second image for the three-dimensional image, generate images process 896 generates a virtual image from a view point with the proper ocular separation so that when the first image and the virtual image are viewed as a stereoscopic pair of images, the surgeon perceives a three-dimensional image.

This approach is sufficient to generate a stereoscopic view of the scene for a virtual camera view point when there are no sharp edges of fore-ground objects in the scene viewed by the monoscopic endoscope. Typically, in a scene of a surgical site, the scene is smooth with no sharp edges and so this process generates useable stereoscopic views. If there is a surgical instrument in the scene, there may be a hole in stereoscopic view behind the surgical instrument, but typically this area is not of interest to the surgeon. The stereoscopic view with the hole behind the surgical instrument provides the information needed by the surgeon and so is acceptable.

In the above examples, beam splitter 831R (831L) was configured as a balanced beam splitter. However, in another aspect, the above examples use a beam splitter 831R (831L) configured to take advantage of the fact that the illumination of a surgical site is typically accomplished with a light guide, called the illumination channel above, which is part of the endoscope. Thus, the illumination is attached to and travels with the tip of the endoscope. As a result, when the endoscope tip is close to the tissue surface, the image is much brighter than when the tissue is far away. In this aspect, coated first surface 831R (831L) is configured to reflect and transmit different portions of the received light, i.e., the first and second percentages defined above are different.

Beam splitter 831R (831L) reflects M % of the received light and passes N % of the received light, where M % is different from N %. Here, M and N are positive numbers. In one aspect, M % plus N % is equal to about one hundred percent. The equality may not be exact due to light losses and due to tolerances of the various parts of image capture unit 825R (825L). The other aspects of prism assembly 830R (830L) are the same as described above. The processing of the images captured by sensor assembly 820R (820L) is equivalent to that described above for the balanced beam splitter and so is not repeated.

In the above examples, the image capture sensors were coplanar. However, it was explained that in some aspects, the image captures sensors can be in parallel planes separated by a known distance. FIG. 9 is a schematic illustration of a part of a channel with an image capture unit that has such image capture sensors. The configuration of FIG. 9 can be used in any of the aspects and examples described herein and so each of the various aspects and examples are not repeated for this configuration.

In FIG. 9, image capture unit 925 includes a lens assembly 901 and a sensor assembly 920. Sensor assembly 920 includes a prism assembly 930, a reflective unit 940, and image capture sensors 910, 915. Lens assembly 901 includes a plurality of optical elements including an optical element that defines an optical stop 970, sometimes referred to as stop 970. Light passing through stop 970 is received by a beam splitter 931 in prism assembly 930 of image capture unit 925.

A stereoscopic apparatus would include two image capture units as illustrated in FIG. 9. However, as demonstrated above with respect to FIG. 3A, the left and right stereoscopic channels with image capture units are symmetric, and so only a single channel and image capture unit is described to avoid duplicative description. The other channel including the image capture unit is symmetric across a plane intersecting the longitudinal axis of the endoscope with the channel illustrated in FIG. 9.

Beam splitter 931 is positioned to receive light that passes through stop 970. Beam splitter 931 is configured to direct a first portion of the received light to a first image capture sensor 910, and to pass a second portion of the received light through the beam splitter to reflective unit 940. In this example, beam splitter 931 in prism assembly 930 is implemented as a coated first surface. Thus, beam splitter 931 is sometimes referred to as coated first surface 931. Coated first surface 931 separates the received light into the two portions.

Coated first surface 931 reflects the first portion of the received light to a second surface 932 that in turn directs, e.g., reflects, the light onto first image capture sensor 910. The second portion of the received light is passed through coated first surface 931 to reflective unit 940. In one aspect, the angle of incidence of the light to coated surface 931 is less than forty-five degrees.

Second surface 932 is positioned so that no light other than the light reflected by coated first surface 931 hits second surface 932. In one aspect, second surface 932 is a reflective surface that is implemented as one of a coated surface and a total internal reflection surface.

Reflective unit 940 includes a third surface 941 that reflects the light received from beam splitter 931 onto a second image capture sensor 915. In one aspect, third surface 941 is a reflective surface implemented, for example, as one of a coated surface and a total internal reflection surface.

First image capture sensor 910 has a top sensor surface in a first plane 911. Second image capture sensor 915 has a top sensor surface in second plane 914. First plane 911 is substantially parallel to second plane 914 and is separated from second plane 914 by a known distance d. Herein, about parallel or substantially parallel means that the two planes are planes within the tolerances associated with manufacturing and mounting the image captures sensors. The top sensor surface of an image capture sensor is the surface of the image capture sensor that receives light from at least one optical component in the sensor assembly.

In one aspect, a first optical path length from stop 970 to coated first surface 931 to second surface 932 to image capture sensor 910 is about equal to a second optical path length from stop 970 through coated first surface 931 to coated surface 941 to image capture sensor 915. Thus, in this aspect, image capture sensors 910 and 915 have a common optical path length through the front end optical structure in lens assembly 901 and about the same optical path length to each image capture sensor in sensor assembly 920.

In another aspect, coated surface 941 is positioned so that the first and second optical path lengths are not equal. In this aspect, image capture sensors 910 and 915 have a common optical path length through the front end optical structure in lens assembly 901 and different optical path lengths to each image capture sensor in sensor assembly 920.

In the examples described above, the implementations considered capture and processing of a single set of images in each channel. This was done for ease of description and is not intended to be limiting. Typically, central controller 260 with camera control units (CCUs) 230R, 230L controls the frequency at which sets of images in each of the channels are captured. The processing of the captured images described above is done in real time, in one aspect, so that the surgeon views a video sequence of stereoscopic images.

Similarly, the different aspects of feature differentiation, enhanced resolution, enhanced dynamic range, variable pixel vector configurations, and extended depth of field were considered separately. However, in view of this disclosure, the different aspects can be combined to achieve the various advantages in combination. The possible permutations to achieve the different combinations are not separately described to avoid repetition.

Also, the above examples, considered an image capture unit mounted at a distal end of an endoscope, either stereoscopic or monoscopic. However, the novel image capture unit configuration can be used in conventional endoscope cameras as well as in for example, stereoscopic surgical microscopes. Accordingly, the description of implementing the image capture unit in an endoscope is illustrative only is not intended to be limiting.

FIG. 10 is a schematic illustration of a distal end of a stereoscopic endoscope 1002 with an image capture unit 1025. Image capture unit 1025 includes left lens assembly 1001L, right lens assembly 1001R and a sensor assembly 1020 with coplanar right and left image capture sensors 1010R and 1010L, in this aspect. In this aspect, stereoscopic endoscope 1002, sometimes referred to as endoscope 1002, includes an illumination channel 1005. However, any of the various illuminators described herein including internal and external illuminators can be used with endoscope 1002. In this aspect, right and left image capture sensors 1010R and 1010L are included in a semiconductor substrate 1017, sometime called a semiconductor die or semiconductor chip, which is mounted on a platform 1012.

The light from tissue 1003 passes through lens assemblies 1001R and 1001L to sensor assembly 1020. The elements in lens assembly 401B (FIG. 4B) are an example of lens assembly 1001R and lens assembly 1001L. The light that passes through lens assemblies 1001R and 1001L is received by a reflective surface 1041 of a reflective unit 1040. Reflective surface 1041 directs, e.g., reflects, the received light onto a top sensor surface of first image capture sensor 1010R and onto a top sensor surface of second image capture sensor 1010L. Surface 1041 can be either a coated surface or a total internal reflection surface.

The optical path lengths to first image capture sensor 1010R and to second image capture sensor 1010L within endoscope 1002 are substantially the same length. For example, a first optical path length from lens assembly 1001R to the top sensor surface of first image capture sensor 1010R is about equal to a second optical path length from lens assembly 1001L to the top sensor surface of second image capture sensor 1010L. Thus, each stereoscopic optical channel in endoscope 1002 has about the same optical path length to an image sensor.

In this aspect, the surface of image capture sensor 1010R and the surface of image capture sensor 1010L are coplanar. Alternatively, image capture sensor 1010R has a top sensor surface in a first plane and image capture sensor 1010L has a top sensor surface in a second plane, where the first and second planes are parallel and are separated by a known distance (See FIG. 9). In this aspect, the position of the reflective surface in the reflective unit is adjusted to compensate for the known distance so that the first optical path length to the first image capture sensor is about equal to the second optical path length to the second image capture sensor. Alternatively or in addition, a lens could be used in one or both of the optical paths to create the about equal optical path lengths.

In the example of FIG. 10 as well as in the alternative arrangement of the image capture sensors, the images captured by first image capture sensor 1010R and to second image capture sensor 1010L have the same focus and depth of field and are spatially registered relative to each other. Image capture unit 1025 is small and compact and so can be used in applications that do not have sufficient space to accommodate the image capture units described above. Also note that this image capture unit is not symmetric about central axis 1090 of endoscope 1002. In certain applications where there are additional lumens for tools or instruments, this asymmetry is an advantage. This construction also affords perfect alignment of the imaging areas for the left and right eyes in the case where the image sensor comprises an imaging area for each eye on a single silicon die or in the case where the device uses a larger imaging device and one does not necessarily use some of the pixels in the region between the two imaging areas.

All examples and illustrative references are non-limiting and should not be used to limit the claims to specific implementations and embodiments described herein and their equivalents. The headings are solely for formatting and should not be used to limit the subject matter in any way, because text under one heading may cross reference or apply to text under one or more headings. Finally, in view of this disclosure, particular features described in relation to one aspect or embodiment may be applied to other disclosed aspects or embodiments of the invention, even though not specifically shown in the drawings or described in the text.

The various modules described herein can be implemented by software executing on a processor, hardware, firmware, or any combination of the three. When the modules are implemented as software executing on a processor, the software is stored in a memory as computer readable instructions and the computer readable instructions are executed on the processor. All or part of the memory can be in a different physical location than a processor so long as the processor can be coupled to the memory. Memory refers to a volatile memory, a non-volatile memory, or any combination of the two.

Also, the functions of the various modules, as described herein, may be performed by one unit, or divided up among different components, each of which may be implemented in turn by any combination of hardware, software that is executed on a processor, and firmware. When divided up among different components, the components may be centralized in one location or distributed across system 200 for distributed processing purposes. The execution of the various modules results in methods that perform the processes described above for the various modules and controller 260.

Thus, a processor is coupled to a memory containing instructions executed by the processor. This could be accomplished within a computer system, or alternatively via a connection to another computer via modems and analog lines, or digital interfaces and a digital carrier line.

Herein, a computer program product comprises a computer readable medium configured to store computer readable code needed for any part of or all of the processes described herein, or in which computer readable code for any part of or all of those processes is stored. Some examples of computer program products are CD-ROM discs, DVD discs, flash memory, ROM cards, floppy discs, magnetic tapes, computer hard drives, servers on a network and signals transmitted over a network representing computer readable program code. A non-transitory tangible computer program product comprises a tangible computer readable medium configured to store computer readable instructions for any part of or all of the processes or in which computer readable instructions for any part of or all of the processes is stored. Non-transitory tangible computer program products are CD-ROM discs, DVD discs, flash memory, ROM cards, floppy discs, magnetic tapes, computer hard drives and other physical storage mediums.

In view of this disclosure, instructions used in any part of or all of the processes described herein can be implemented in a wide variety of computer system configurations using an operating system and computer programming language of interest to the user.

Herein, first and second are used as adjectives to distinguish between elements and are not intended to indicate a number of elements. Also, top, bottom, and side are used as adjectives to aid in distinguishing between elements as viewed in the drawings, and to help visualize relative relationships between the elements. For example, top and bottom surfaces are first and second surfaces that are opposite and removed from each other. A side surface is a third surface that extends between the first and second surfaces. Top, bottom, and side are not being used to define absolute physical positions.

The above description and the accompanying drawings that illustrate aspects and embodiments of the present inventions should not be taken as limiting—the claims define the protected inventions. Various mechanical, compositional, structural, electrical, and operational changes may be made without departing from the spirit and scope of this description and the claims. In some instances, well-known circuits, structures, and techniques have not been shown or described in detail to avoid obscuring the invention.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of the device in use or operation in addition to the position and orientation shown in the figures. For example, if the device in the figures is turned over, elements described as "below" or "beneath" other elements or features would then be "above" or "over" the other elements or features. Thus, the exemplary term "below" can encompass both positions and orientations of above and below. The device may be otherwise oriented (rotated 90 degrees or at other orientations) and the spatially relative descriptors used herein interpreted accordingly. Likewise, descriptions of movement along and around various axes include various special device positions and orientations.

The singular forms "a", "an", and "the" are intended to include the plural forms as well, unless the context indicates otherwise. The terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components.

What is claimed is:

1. In a system comprising an image capture unit, a method comprising:
    separating, by a beam splitter of the image capture unit, light received from a common front end optical system into a first portion and a second portion;
    reflecting, by a surface separated from the beam splitter, the first portion of the received light in a first direction to a first image capture sensor of the image capture unit;
    directing in the first direction, by a reflective unit of the image capture unit, the second portion of the received light to a second image capture sensor of the image capture unit;
    capturing, in the first image capture sensor, a first image from the first portion of the received light; and
    capturing, in the second image capture sensor of the image capture unit, a second image from the second portion of the received light,
        wherein a first optical path length in the image capture unit to the first image capture sensor is about equal to a second optical path length in the image capture unit to the second image capture sensor,
        wherein a first image capture sensor surface of the first image capture sensor is in a first plane, a second image capture sensor surface of the second image capture sensor is in a second plane, and
        wherein the first and second planes are parallel to a longitudinal axis of image capture unit.

2. The method of claim 1, the first and second image capture sensor surfaces being coplanar so that the first and second planes are a same plane.

3. The method of claim 1, the first and second planes being separated by a known distance.

4. The method of claim 1, wherein the first portion of the received light is not equal to the second portion of the received light.

5. The method of claim 1, wherein the first portion of the received light is equal to the second portion of the received light.

6. The method of claim 5, the beam splitter and the surface being positioned to offset an image captured by the first image capture sensor from an image captured by the second image capture sensor with the first optical path length remaining about equal to the second optical path length.

7. The method of claim 1:
    the received light comprising a plurality of color components, the first portion comprising one color component of the plurality of color components; and
    the second portion comprising other color components of the plurality of color components.

8. The method of claim 7, the first and second image capture sensor surfaces being coplanar so that the first and second planes are a same plane.

9. The method of claim 7, the first and second planes being separated by a known distance.

10. The method of claim 7:
    the first image capture sensor comprising a monochrome image capture sensor; and
    the second image capture sensor comprising an image capture sensor having a color filter array for the other color components in the plurality of color components.

11. The method of claim 10,
    wherein the one color component of the plurality of color components is a green color component; and
    wherein the other color components of the plurality of color components are a red color component and a blue color component.

* * * * *

UNITED STATES PATENT AND TRADEMARK OFFICE
CERTIFICATE OF CORRECTION

PATENT NO. : 10,809,519 B2
APPLICATION NO. : 16/139288
DATED : October 20, 2020
INVENTOR(S) : Ian E. McDowall Page 1 of 1

It is certified that error appears in the above-identified patent and that said Letters Patent is hereby corrected as shown below:

On the Title Page

Replace item (73) Assignee: KITAGAWA INDUSTRIES CO., LTD., Aichi (JP)
With the following:
--(73) Assignee: Intuitive Surgical Operations, Inc., Sunnyvale, CA (US)--

Signed and Sealed this
Sixth Day of July, 2021

Drew Hirshfeld
*Performing the Functions and Duties of the*
*Under Secretary of Commerce for Intellectual Property and*
*Director of the United States Patent and Trademark Office*